US012685751B2

(12) United States Patent
Beard et al.

(10) Patent No.: US 12,685,751 B2
(45) Date of Patent: Jul. 21, 2026

(54) METHODS FOR GENE MODIFICATION OF HEMATOPOIETIC CELLS

(71) Applicants: Centro de Investigaciones Energéticas, Medioambientales y Tecnológicas, O.A., M.P., Madrid (ES); Consorcio Centro de Investigación Biomédica en Red, M.P., Madrid (ES); Fundación Instituto de Investigación Sanitaria Fundación Jiménez Díaz, Madrid (ES); Spacecraft Seven, LLC, Cranbury, NJ (US)

(72) Inventors: Brian Beard, New York, NY (US); Gaurav D. Shah, New York, NY (US); Juan Antonio Bueren Roncero, Madrid (ES); Jose Carlos Segovia Sanz, Madrid (ES); Paula Rio Galdo, Madrid (ES); Susana Navarro Ordonez, Madrid (ES); Elena Almarza Novoa, Madrid (ES); Oscar Quintana Bustamante, Madrid (ES); Cristina Mesa Nunez, Madrid (ES); Kenneth Law, New York, NY (US); Kinnari Patel, New York, NY (US)

(73) Assignees: CENTRO DE INVESTIGACIONES ENERGETICAS, MEDIOAMBIENTALES Y TECNOLOGICAS, O.A., M.P., Madrid (ES); CONSORCIO CENTRO DE INVESTIGACION BIOMEDICA EN RED, M.P., Madrid (ES); FUNDACION INSTITUTO DE INVESTIGACION SANITARIA FUNDACION JIMENEZ DIAZ, Madrid (ES); SPACECRAFT SEVEN, LLC, Cranbury, NJ (US)

( * ) Notice: Subject to any disclaimer, the term of this patent is extended or adjusted under 35 U.S.C. 154(b) by 1032 days.

(21) Appl. No.: 17/264,275

(22) PCT Filed: Jul. 30, 2019

(86) PCT No.: PCT/US2019/044237

§ 371 (c)(1),
(2) Date: Jan. 28, 2021

(87) PCT Pub. No.: WO2020/028430

PCT Pub. Date: Feb. 6, 2020

(65) Prior Publication Data

US 2021/0290685 A1 Sep. 23, 2021

Related U.S. Application Data

(60) Provisional application No. 62/712,146, filed on Jul. 30, 2018.

(51) Int. Cl.

| | |
|---|---|
| *A61K 35/28* | (2015.01) |
| *C12N 5/0789* | (2010.01) |
| *C12N 15/86* | (2006.01) |

(52) U.S. Cl.

CPC ............ *A61K 35/28* (2013.01); *C12N 5/0647* (2013.01); *C12N 15/86* (2013.01); *C12N 2500/50* (2013.01); *C12N 2740/15043* (2013.01)

(58) Field of Classification Search

CPC ...... A61K 35/28; C12N 5/0647; C12N 15/86; C12N 2500/50; C12N 2740/15043

See application file for complete search history.

(56) References Cited

U.S. PATENT DOCUMENTS

| | | | |
|---|---|---|---|
| 5,126,260 | A | 6/1992 | Tuan et al. |
| 5,278,056 | A | 1/1994 | Bank et al. |
| 5,633,156 | A | 5/1997 | Wurm et al. |
| 5,994,136 | A | 11/1999 | Naldini et al. |
| 6,013,516 | A | 1/2000 | Verma et al. |
| 6,027,721 | A | 2/2000 | Hammang et al. |
| 6,136,597 | A | 10/2000 | Hope et al. |
| 7,198,950 | B2 | 4/2007 | Trono et al. |
| 7,575,924 | B2 | 8/2009 | Trono et al. |
| 7,629,153 | B2 | 12/2009 | Trono et al. |
| 8,093,042 | B2 | 1/2012 | Charneau et al. |

(Continued)

FOREIGN PATENT DOCUMENTS

| | | | |
|---|---|---|---|
| DE | 102008063606 | A1 | 6/2010 |
| JP | 2006524051 | A | 10/2006 |

(Continued)

OTHER PUBLICATIONS

Lee, Hyun-Joo, et al. “Retronectin enhances lentivirus-mediated gene delivery into hematopoietic progenitor cells.” Biologicals 37.4 (2009): 203-209. (Year: 2009).*

(Continued)

*Primary Examiner* — Teresa E Knight
*Assistant Examiner* — Michael Angelo Riga
(74) *Attorney, Agent, or Firm* — COOLEY LLP

(57) ABSTRACT

The present invention relates generally to methods for genetic modification of hematopoietic cells. In particular, the invention relates to use of Prostaglandin E2 (PGE2), poloxamer, and protamine sulfate to enhance transduction by a recombinant retroviral vector. The compositions and methods of the present disclosure are particularly suitable for gene therapy applications, including the treatment of monogenic genetic diseases and disorders.

27 Claims, 23 Drawing Sheets

Specification includes a Sequence Listing.

(56) References Cited

U.S. PATENT DOCUMENTS

| | | | |
|---|---|---|---|
| 8,137,959 | B2 | 3/2012 | Castillo Fernandez |
| 8,329,462 | B2 | 12/2012 | Trono et al. |
| 8,597,939 | B2 | 12/2013 | Castillo Fernandez |
| 8,727,132 | B2 | 5/2014 | Miltenyi et al. |
| 8,748,169 | B2 | 6/2014 | Trono et al. |
| 8,900,858 | B2 | 12/2014 | Trono et al. |
| 9,109,012 | B2 | 8/2015 | Williams |
| 9,175,077 | B2 | 11/2015 | Gallo et al. |
| 9,340,798 | B2 | 5/2016 | Trono et al. |
| 9,737,620 | B2 | 8/2017 | Williams |
| 9,771,599 | B2 | 9/2017 | Anastasov et al. |
| 10,363,269 | B2 | 7/2019 | Tareen |
| 2002/0065236 | A1 | 5/2002 | Yew et al. |
| 2004/0053870 | A1 | 3/2004 | Yew et al. |
| 2006/0200869 | A1 | 9/2006 | Naldini et al. |
| 2006/0247214 | A1 | 11/2006 | Delong et al. |
| 2008/0248552 | A1 | 10/2008 | Castillo Fernandez |
| 2009/0088398 | A1 | 4/2009 | Gregory et al. |
| 2009/0111106 | A1 | 4/2009 | Mitrophanous et al. |
| 2010/0284990 | A1 | 11/2010 | Kaemmerer et al. |
| 2012/0071859 | A1 | 3/2012 | Morgan et al. |
| 2012/0172418 | A1 | 7/2012 | Schambach et al. |
| 2012/0283318 | A1 | 11/2012 | Mei et al. |
| 2014/0220678 | A1 | 8/2014 | Trono et al. |
| 2015/0031134 | A1 | 1/2015 | Zhang et al. |
| 2015/0203852 | A1 | 7/2015 | Arora |
| 2015/0291966 | A1 | 10/2015 | Zhang et al. |
| 2016/0108430 | A1 | 4/2016 | Carrier et al. |
| 2016/0194660 | A1 | 7/2016 | Ye |
| 2017/0051309 | A1 | 2/2017 | Lesch et al. |
| 2018/0169148 | A1 | 6/2018 | Adair et al. |
| 2018/0195048 | A1 | 7/2018 | Rao |
| 2018/0326022 | A1 | 11/2018 | Prosser et al. |
| 2018/0360992 | A1 | 12/2018 | Patel et al. |
| 2019/0038773 | A1 | 2/2019 | Esteves et al. |
| 2019/0284533 | A1 * | 9/2019 | Bonner ................ C12N 15/867 |

FOREIGN PATENT DOCUMENTS

| | | | | |
|---|---|---|---|---|
| JP | 2007054069 | A | 3/2007 | |
| RU | 2233333 | C2 | 7/2004 | |
| RU | 2280074 | C2 | 7/2006 | |
| WO | WO-9419478 | A1 | 9/1994 | |
| WO | WO-01/12596 | | 2/2001 | |
| WO | WO-03092612 | A2 | 11/2003 | |
| WO | WO-2008136670 | A2 | 11/2008 | |
| WO | WO-2014093444 | A1 | 6/2014 | |
| WO | WO-2015056014 | A1 | 4/2015 | |
| WO | WO-2015168547 | A2 | 11/2015 | |
| WO | WO-2015188191 | A1 | 12/2015 | |
| WO | WO-2016041080 | A1 | 3/2016 | |
| WO | WO-2016/118780 | A1 | 7/2016 | |
| WO | WO-2016145217 | A1 | 9/2016 | |
| WO | WO-2017127565 | A1 | 7/2017 | |
| WO | WO-2017139576 | A1 * | 8/2017 | ............. A61K 35/28 |
| WO | WO-2017184903 | A1 | 10/2017 | |
| WO | WO-2017218519 | A1 | 12/2017 | |
| WO | WO-2017218948 | A2 | 12/2017 | |
| WO | WO-2018007873 | A1 | 1/2018 | |
| WO | WO-2018/049273 | A1 | 3/2018 | |
| WO | WO-2018106807 | A1 | 6/2018 | |
| WO | WO-2018106821 | A1 | 6/2018 | |
| WO | WO-2018201065 | A1 | 11/2018 | |
| WO | WO-2019079338 | A1 | 4/2019 | |
| WO | WO-2019/200167 | A1 | 10/2019 | |
| WO | WO-2019210325 | A1 | 10/2019 | |
| WO | WO-2020/014523 | A1 | 1/2020 | |
| WO | WO-2020028430 | A1 | 2/2020 | |
| WO | WO-2020037249 | A1 | 2/2020 | |
| WO | WO-2020167996 | A1 | 8/2020 | |
| WO | WO-2020237219 | A1 | 11/2020 | |
| WO | WO-2021236981 | A2 | 11/2021 | |
| WO | WO-2022017630 | A1 | 1/2022 | |
| WO | WO-2022018171 | A1 | 1/2022 | |
| WO | WO-2022031756 | A1 | 2/2022 | |
| WO | WO-2022031760 | A1 | 2/2022 | |
| WO | WO-2022032226 | A1 | 2/2022 | |
| WO | WO-2022125489 | A1 | 6/2022 | |
| WO | WO-2023108029 | A2 | 6/2023 | |
| WO | WO-2023108129 | A1 | 6/2023 | |
| WO | WO-2023154763 | A2 | 8/2023 | |
| WO | WO-2023205767 | A2 | 10/2023 | |

OTHER PUBLICATIONS

Moritz, Thomas, et al. "Fibronectin improves transduction of reconstituting hematopoietic stem cells by retroviral vectors: evidence of direct viral binding to chymotryptic carboxy-terminal fragments." (1996): 855-862 (Year: 1996).*

Leon-Rico, Diego, et al. "Lentiviral vector-mediated correction of a mouse model of leukocyte adhesion deficiency type I." Human gene therapy 27.9 (2016): 668-678. (Year: 2016).*

Garcia-Gomez, Maria, et al. "Safe and efficient gene therapy for pyruvate kinase deficiency." Molecular Therapy 24.7 (2016): 1187-1198. (Year: 2016).*

Canu, Giulia, et al. "Red blood cell PK deficiency: an update of PK-LR gene mutation database." Blood Cells, Molecules, and Diseases 57 (2016): 100-109. (Year: 2016).*

Moscatelli, Ilana, et al. "Lentiviral gene transfer of TCIRG1 into peripheral blood CD34+ cells restores osteoclast function in infantile malignant osteopetrosis." Bone 57.1 (2013): 1-9. (Year: 2013).*

Zhang, Yi, and Zhi-Ying Wu. "Gene therapy for monogenic disorders: challenges, strategies, and perspectives." Journal of Genetics and Genomics 51.2 (2024): 133-143. (Year: 2024).*

Aiuti, A. et al. (2013). "Lentiviral hematopoietic stem cell gene therapy in patients with Wiskott-Aldrich syndrome," Science 341:1233151. 29 pages.

Albrechtsen, B. et al. (1991). "Transcriptional termination sequence at the end of the *Escherichia coli* ribosomal RNA G operon: Complex terminators and antitermination" Nucl. Acids Res. 19:1845-1852.

Almarza, E. et al. (2011). "Correction of SCID-X1 using an enhancerless Vav promoter," Hum. Gene Ther. 22:263-270.

Badri et al., "Optimization of radiation dosing schedules for proneural glioblastoma" J Math Biol. Apr. 2016; 72(5):1301-36. doi: 10.1007/s00285-015-0908-x. Epub Jun. 21, 2015.

Baylot V. et al., "TCTP Has a Crucial Role in the Different Stages of Prostate Cancer Malignant Progression" Results Probl Cell Differ. (2017) 64:255-261.

Biffi, A. et al. (2013). "Lentiviral hematopoietic stem cell gene therapy benefits metachromatic leukodystrophy," Science 341:1233158. 14 pages.

Bouchard, M.J. et al. (2004). "The Enigmatic X Gene of Hepatitis B Virus" J. Virol. 78:12725-12734.

Braun, C.J. et al. (2014). "Gene therapy for Wiskott-Aldrich syndrome-long-term efficacy and genotoxicity," Sci. Transl. Med. 6:227ra33. 15 pages.

Breda, L. et al. (2012). "Therapeutic hemoglobin levels after gene transfer in β-thalassemia mice and in hematopoietic cells of β-thalassemia and sickle cells disease patients," PLoS One 7:e32345. 16 pages.

Bueren, J. et al. (2019). "Advances in the Gene Therapy of Monogenic Blood Cell Diseases" Clin Genet., with Tables I-II, 46 total pages.

Cartier, N, et al. (2009). "Hematopoietic stem cell gene therapy with a lentiviral vector in X-linked adrenoleukodystrophy," Science 326:818-823.

Cartier, N. et al. (2012). "Lentiviral hematopoietic cell gene therapy for X-linked adrenoleukodystrophy," Methods Enzymol. 507:187-198.

Cavazzana et al., "Gene Therapy for β-Hemoglobinopathies" Mol Ther. May 3, 2017; 25(5):1142-1154. doi: 10.1016/j.ymthe.2017.03.024.

Cavazzana-Calvo, M. et al. (2010). "Transfusion independence and HMGA2 activation after gene therapy of human β-thalassaemia," Nature 467:318-322.

(56) References Cited

OTHER PUBLICATIONS

Charrier et al. (2011). "Quantification of lentiviral vector copy numbers in individual hematopoietic colony-forming cells shows vector dose-dependent effects on the frequency and level of transduction," Gene Ther. 18:479-487.
Charrier, S. et al. (2005). "A lentiviral vector encoding the human Wiskott-Aldrich syndrome protein corrects immune and cytoskeletal defects in WASP knockout mice," Gene Ther. 12:597-606.
Donello, J.E. et al. (1998). "Woodchuck hepatitis virus contains a tripartite posttranscriptional regulatory element," J. Virol. 72:5085-5092.
Ellis, J. (2005). "Silencing and variegation of gammaretrovirus and lentivirus vectors," Hum. Gene Ther. 16:1241-1246.
Extended European Search Report in EP Patent Application No. 19849869.3, mailed Apr. 19, 2022, 7 pages.
Follenzi, A. et al. (2000). "Gene transfer by lentiviral vectos is limited by nuclear translocation and rescued by HIV-1 pol sequences," Nat. Genet. 25:217-222.
Galibert, F et al., "Woodchuck hepatitis virus, complete genome," GenBank: J02442.1, publication date: Aug. 3, 1993. 2 pages.
Gerolami, R. et al. (2000). "Gene transfer to hepatocellular carcinoma: transduction efficacy and transgene expression kinetics by using retroviral and lentiviral vectors," Cancer Gene Ther. 7:1286-1292.
Ginn, S.L. et al. (2003). "Promoter interference mediated by the U3 region in early-generation HIV-1-derived lentivirus vectors can influence detection of transgene expression in a cell-type and species-specific manner," Hum. Gene Ther. 14:1127-1137.
Gonzalez-Murillo, A. et al. (2008). "Unaltered repopulation properties of mouse hematopoietic stem cells transduced with lentiviral vectors" Blood 112:3138-3147.
Hacein-Bey-Abina, S. et al. (2008). "Insertional oncogenesis in 4 patients after retrovirus-mediated gene therapy of SCID-X1," J. Clin. Invest. 118:3132-3142.
Hlavaty, J. et al. (2005). "Effect of posttranscriptional regulatory elements on transgene expression and virus production in the context of retrovirus vectors," Virology 341:1-11.
Howe, S.J. et al. (2008). "Insertional mutagenesis combined with acquired somatic mutations causes leukemogenesis following gene therapy of SCID-X1 patients," J. Clin. Invest. 118:3143-3150.
International Search Report mailed on Oct. 29, 2019, for PCT application No. PCT/US2019/046890, filed on Aug. 16, 2019, 3 pages.
Iwakuma, T. et al. (1999). "Self-inactivating lentiviral vectors with U3 and U5 modifications," Virology 261:120-132.
Jacome, A. et al. (2009). "Lentiviral-mediated genetic correction of hematopoietic and mesenchymal progenitor cells from Fanconi anemia patients" Mol. Ther. 17:1083-1092.
Kingsman, S.M. et al. (2005). "Potential oncogene activity of the Woodchuck Hepatitis post-transcriptional regulatory element (WPRE)" Gene Ther. 12:3-4.
Lofvall et al., "Regulation and function of lentiviral-mediated TCIRG1 expression in osteoclasts from infantile malignant osteopetrosis patients" Abstract P192 in Bone Abstracts (2016) vol. 5, 7 pages.
Matrai, J. et al. (2010). "Preclinical and clinical progress in hemophilia gene therapy" Curr Opin Hematol. 17:387-392.
Merten, O-W: "State-of-the-art of the production of retroviral vectors," The Journal of Gene Medicine, John Wiley & Sons, Inc., US, vol. 6, No. Suppl. 1, Feb. 1, 2004, pp. S105-S124.
Mitchell, R.S. et al. (2004). "Retroviral DNA integration: ASLV, HIV, and MLV show distinct target site preferences" PLoS Biol. 2:E234. 11 pages.
Miyoshi, H. et al. (1998). "Development of a self-inactivating lentivirus vector," J. Virol. 72:8150-8157.
Modlich, U. et al. (2009). "Insertional Transformation of Hematopoietic Cells by Self-Inactivating Lentiviral And Gammaretroviral Vectors" Mol Ther. 17:1919-1928.
Montini, E. et al. (2006). "Hematopoietic stem cell gene transfer in a tumor-prone mouse model uncovers low genotoxicity of lentiviral vector integration" Nat Biotechnol. 24:687-696.
Montini, E. et al. (2009). "The genotoxic potential of retroviral vectors is strongly modulated by vector design and integration site selection in a mouse model of HSC gene therapy" J. Clin. Invest. 119:964-975.
Morris, J.C. et al. (2004). "Induction of cytotoxic T-lymphocyte response to enhanced green and yellow fluorescent proteins after myeloablative conditioning" Blood 103:492-499.
Moscatelli et al., "Targeting NSG Mice Engrafting Cells with a Clinically Applicable Lentiviral Vector Corrects Osteoclasts in Infantile Malignant Osteopetrosis" Hum Gene Ther. Aug. 29, 2018; (8):938-949.
Moscatelli, I. et al. (2013). "Lentiviral gene transfer of TCIRG1 into peripheral blood CD34+ cells restores osteoclast function in infantile malignant osteopetrosis," Bone 57:1-9.
Mothy et al., "The Role of Plerixafor in Optimizing Peripheral Blood Stem Cell Mobilization for Autologous Stem Cell Transplantaion," Leukemia (2011) 25, 1-6.
Mulroney-Cousins et al., "Primary seronegative but molecularly evident hepadnaviral infection engages liver and induces hepatocarcinoma in the woodchuck model of hepatitis B," PLoS. Pathog. 10 (8), E1004332 (2014). 13 pages.
Naldini, L. (1998). "Lentiviruses as gene transfer agents for delivery to non-dividing cells," Curr. Opin. Biotechnol. 9:457-463.
Naldini, L. (2011). "Ex vivo gene transfer and correction for cell-based therapies" Nature Reviews Genetics 12:301-315.
Naldini, L. et al. (1996). "Efficient transfer, integration, and sustained long-term expression of the transgene in adult rat brains injected with a lentiviral vector," PNAS 93:11382-11388.
Naldini, L. et al. (1996). "In vivo gene delivery and stable transduction of nondividing cells by a lentiviral vector," Science 272:263-267.
Oh, T. et al. (2007). "Lentiviral vector design using alternative RNA export elements," Retrovirology 4:38. 10 pages.
Ott, M.G. et al. (2006). "Correction of X-linked chronic granulomatous disease by gene therapy, augmented by insertional activation of MDS1-EVI1, PRDM16 or SETBP1," Nat. Med. 12:401-409.
Paruzynski, A. et al. (2010). "Genome-wide high-throughput integrome analyses by nrLAM-PCR and next-generation sequencing," Nat. Protoc. 5:1379-1395.
Pestina, T.I. et al. (2009). "Correction of murine sickle cell disease using gamma-globin lentiviral vectors to mediate high-level expression of fetal hemoglobin," Mol. Ther. 17:245-252.
Pfeifer, A. et al. (2002). "Transgenesis by lentiviral vectors: Lack of gene silencing in mammalian embryonic stem cells and preimplementation embryos," PNAS 99:2140-2145.
Pfeifer G.P. et al., "*Homo sapiens* phosphoglycerate kinase 1 (PGK1) gene, partial cds," GenBank: M60581.1, publication date: Jul. 26, 2016. 1 page.
Powell, S.K. et al. (2015). "Viral Expression Cassette Elements to Enhance Transgene Target Specificity and Expression in Gene Therapy," Discov. Med. 19:49-57.
Salmon, P. et al. (2000). "High-level transgene expression in human hematopoietic progenitors and differentiated blood lineages after transduction with improved lentiviral vectors," Blood 96:3392-3398.
Schambach, A. et al. (2006). Overcoming promoter competition in packaging cells improves production of self-inactivating retroviral vectors, Gene Ther. 13:1524-1533.
Schambach, A. et al. (2006). "Woodchuck hepatitis virus post-transcriptional regulatory element deleted from X protein and promoter sequences enhances retroviral vector titer and expression" Gene Ther. 13:641-645.
Schambach, A. et al. (2007). "Improving transcriptional termination of self-inactivating Gamma-retroviral and lentiviral vectors" Mol Ther. 15:1167-1173.
Schambach, M.R. et al. (2010). "Synthetic design of strong promoters," PNAS 107:2538-2543.
Schroder, A.R.W. et al. (2002). "HIV-1 integration in the human genome favors active genes and local hotspots" Cell 110:521-529.
Socolovsky, M. et al. (2001). "Ineffective erythropoiesis in Stat5a(-/-)5b(-/-) mice due to decreased survival of early erythroblasts," Blood 98:3261-3273.

(56) References Cited

OTHER PUBLICATIONS

Stein, S. et al. (2010). "Genomic instability and myelodysplasia with monosomy 7 consequent to EVI1 activation after gene therapy for chronic granulomatous disease," Nat. Med. 16:198-204.
Stripecke, R. et al. (1999). "Immune response to green fluorescent protein: Implications for gene therapy" Gene Ther. 6:1305-1312.
Takeshita, F. et al. "Muscle creatine kinase/SV40 hybrid promoter for muscle-targeted long-term transgene expression." International Journal of Molecular Medicine, vol. 19.2 (2007): pp. 309-315, 7 pages.
Thudium et al., "Regulation and Function of Lentiviral Vector-Mediated TCIRG1 Expression in Osteoclasts from Patients with Infantile Malignant Osteopetrosis: Implications for Gene Therapy" Calcif Tissue Int. Dec. 2016; 99(6):638-648.
Valkama, A.J. et al. (2018). "Optimization of lentiviral vector production for scale-up in fixed-bed bioreactor," Gene Therapy 25:39-46.
Written Opinion of the International Searching Authority mailed on Oct. 29, 2019, for PCT application No. PCT/US2019/046890, filed on Aug. 16, 2019, 5 pages.
Zaiss, A-K. et al. (2002). "RNA 3' readthrough of oncoretrovirus and lentivirus: Implications for vector safety and efficacy," J. Virol. 76:7209-7219.
Zanta-Boussif, M.A. et al. (2009). "Validation of a mutated PRE sequence allowing high and sustained transgene expression while abrogating WHV-X protein synthesis: Application to the gene therapy of WAS" Gene Ther. 16:605-619.
Zaucha, J.M. et al. (2001). "Effects of extending the duration of postgrafting immunosuppression and substituting granulocyte-colony-stimulating factor-mobilized peripheral blood mononuclear cells for marrow in allogeneic engraftment in a nonmyeloablative canine transplantation model" Biol Blood Marrow Transplant. 7:513-516.
Zennou, V. et al. (2000). "HIV-1 genome nuclear import is mediated by a central DNA flap" Cell 101:173-185.
Zufferey, R. et al. (1997). "Multiply attenuated lentiviral vector achieves efficient gene delivery in vivo," Nat. Biotechnol. 15:871-875.
Zychlinski, D. et al. (2008). "Physiological promoters reduce the genetoxic risk of integrating gene vectors" Mol Ther. 16:718-725.
Cutler, C. et al., "Prostaglandin-modulated umbilical cord blood hematopoietic stem cell transplantation," 2013, Blood, vol. 122(17), pp. 3074-3081.
Delville, M. et al., "A Nontoxic Transduction Enhancer Enables Highly Efficient Lentiviral Transduction of Primary Murine T Cells and Hematopoietic Stem Cells," 2018, Mol. Ther.—Methods Clin. Dev., vol. 10, pp. 341-347.
Extended European Search Report mailed on Apr. 4, 2022, for EP Application No. 19844952.2, filed on Jul. 30, 2019, 6 pages.
Goessling et al., "Prostaglandin E2 Enhances Human Cord Blood Stem Cell Xenotransplants and Shows Long-Term Safety in Preclinical Nonhuman Primate Transplant Models," Cell Stem Cell (2011), 8: 445-458.
Mesa-Núñez, C. et al., "Preclinical safety and efficacy of lentiviral-mediated gene therapy for leukocyte adhesion deficiency type I," 2022, Molecular Therapy Methods and Clinical Development, vol. 26, pp. 459-470.
Zonari, E. et al., "Efficient Ex Vivo Engineering and Expansion of Highly Purified Human Hematopoietic Stem and Progenitor Cell Populations for Gene Therapy," Stem Cell Reports, 8(4):977-990 (2017).
Butturini A, et al. (1994). Hematologic abnormalities in Fanconi anemia: An international Fanconi anemia registry study, Blood 84:1650-1655.
Cid-Arregui, A. et al. (2003). A synthetic E7 gene of human papillomavirus type 16 that yields enhanced expression of the protein in mammalian cells and is useful for ONA immunization studies, J. Virol. 77:4928.
Craddock, C.F. et al. (1997). Antibodies to VLA4 integrin mobilize long-term repopulating cells and augment cytokine-induced mobilization in primates and mice, Blood 90:4779-4788.
Cronin, J. et al. (2005). "Altering the tropism of lentiviral vectors through pseudotyping," Curr. Gene Ther. 5:387-398.
Denning, W. et al. (2013). "Optimization of the transductional efficiency of lentiviral vectors: effect of sera and polycations," Mol Biotechnol. 53:308-314.
Dipersio, J.F. et al. (2009). "Phase III prospective randomized double-blind placebo-controlled trial of pierixafor plus granulocyte colony-stimulating factor compared with placebo plus granulocyte colony-stimulating factor for autologous stem-cell mobilization and transplantation for patients with non-Hodgkin's lymphoma," J. Clin. Oncol. 27:4767-4773.
Dull, T. et al. (1998). "A third-generation lentivirus vector with a conditional packaging system," J. Mirol. 72:8463-8471.
Garica-Gomez, M. et al. (2016). "Safe and efficient gene therapy for pyruvate kinase deficiency," Mol Ther. 24:1187-1198.
Good, N.E. et al. (1966). "Hydrogen ion buffers for biological research," Biochemistry 5:467-477.
Hauber, I. at al. (2018). "Improving lentiviral transduction of CD34+ hematopoietic stem and progenitor cells," Hum. Gene Ther. Methods 29:104-113.
Heffner, G.C. et al. (2018). "Prostaglandin $E_2$ Increases Lentiviral Vector Transduction Efficiency of Adult Human Hematopoietic Stem and Progenitor Cells," Mol Ther. 3:26:320-328.
Höfig, I et al. (2012). "Poloxamer synperonic F108 improves cellular transduction with lentiviral vectors," J. Gene Med. 14:549-560.
International Search Report mailed on Dec. 2, 2019, for PCT Application No. PCT/US2019/044237, filed on Jul. 30, 2019, 6 pages.
Jin, P. et al. (2008). Differentiation of two types of mobilized peripheral blood stem sells by microRNA and cDNA expression analysis, J. Translational Med. 6:39.
Koda, H. et al. (1984). Antibody synthesis by bone marrow cells in vitro following primary and booster tetanus toxoid immunization in humans, J. Clin. Invest. 73:1377-1384.
Kutler, D.I. et al. (2003). "A 20-year perspective on the international Fanconi anemia registry (IFAR)," Blood 101:1249-1256.
Miller, A.D. (1992). "Human gene therapy comes of age," Nature 357:455-460.
Papayannopoulou, T. et al. (1998). Anti-VLA4/VCAM-1-induced mobilization requires cooperative signaling through the kit/mkit ligand pathway, Blood 91:2231-2239.
Pelus, L.M. (2008). Peripheral blood stream cell mobilization: New regimens, new cells, where do we stand, Curr. Opin. Hematol. 15:285-292.
Sarma, N.J. et al. (2010). "Colony forming cell (CFC) assay for human hematopoietic cells," J. Vis. Exp. 18:2195.
Sevilla, J. et al. (2016). Immunomagnetic T cell depletion: An analysis of variables affecting final cell yield, Clin. Lab. 62:1243-1248.
Tricot, G. et al. (2008), Mobilization of peripheral blood stem cells in myeloma with either pegfilgrastim or filgrastim following chemotherapy, Haematologica 93:1739-1742.
Weaver, C.H. et al. (2001). Mobilization of peripheral blood stem cells following myelosuppressive chemotherapy: A randomized comparison of filgrastim, sargramostim, or sequential sargramostim and filgrastim, Bone Marrow Transplantation 27:S23-S29.
Written Opinion of the International Searching Authority mailed on Dec. 2, 2019, for PCT Application No. PCT/US2019/044237, filed on Jul. 30, 2019, 9 pages.
Zufferey, R. et al. (1999). "Woodchuck Hepatitis Virus Post-transcriptional Regulatory Element Enhances Expression of Transgenes Delivered by Retroviral Vectors," Journal of Virology 73:2886-2892.
Zufferey, R. et al. (1998). Self-inflicting lentivirus vector for safe and efficient In Vivo gene delivery, J. Virol. 72:9873-9880.
Leon-Rico et al., "Lentiviral Vector-Mediated Correction of a Mouse Model of Leukocyte Adhesion Deficiency Type I" Human Gene Therapy Sep. 2016; 27(9):668- 678.
Relander et al., "Retroviral transduction of human CD34+ cells on fibronectin fragment CH-296 is inhibited by high concentrations of vector containing medium" J Gene Med (2001) 3(2):207-218.

(56) References Cited

OTHER PUBLICATIONS

Forman et al., "Thomas' Hematopoietic Cell Transplantation: stem cell transplantation" 5th edition, pp. 82-83, publication date: Dec. 31, 2016.
Schott et al., "Enhancing Lentiviral and Alpharetroviral Transduction of Human Hematopoietic Stem Cells for Clinical Application" Mol Ther Methods Clin Dev. Jun. 7, 2019; 14:134-147.
Hunter et al., "Gene Therapy of Canine Leukocyte Adhesion Deficiency Using Lentiviral Vectors With Human CD11b and CD18 Promoters Driving Canine CD18 Expression" Molecular Therapy Jan. 2011; 19:113-121.
Back et al., "Retroviral-mediated gene transfer of the leukocyte integrin CD18 subunit" Biochem Biophys Res Commun. Sep. (1990);171(2):787-795.
Real et al., "Improvement of lentiviral transfer vectors using cis-acting regulatory elements for increased gene expression" Applied Genetics and Molecular Biotechnology Jun. (2011); 91:1581-1591.
Santilli et al., "Biochemical Correction of X-CGD by a Novel Chimeric Promoter Regulating High Levels of Transgene Expression in Myeloid Cells" Mol Ther. Jan. (2011); 19(1):122-132.
Wilson et al., "Correction of CD18-Deficient Lymphocytes by Retrovirus-Mediated Gene Transfer" Science Jun. (1990); 248(4961):1413-1416.

* cited by examiner

FIG. 18
cPPT
psi
5' LTR
RNA OUT
SV40 origin
SV40 PolyA
3' LTR (Delta-U3)
cPPT
pCCL-EFS-TCIRG1-WPRE-82-RO
7,660 bp

SEQUENCE LISTING

<160> NUMBER OF SEQ ID NOS: 11

<210> SEQ ID NO 1
<211> LENGTH: 5554
<212> TYPE: DNA
<213> ORGANISM: Artificial Sequence
<220> FEATURE:
<223> OTHER INFORMATION: pCCL-PGK-FANCAW-82-PRO vector sequence

<400> SEQUENCE: 1
ggggttgggg ttgcgccttt tccaaggcag ccctgggttt gcgcagggac gcggctgctc 60
tgggcgtggt tccgggaaac gcagcggcgc cgaccctggg tctcgcacat tcttcacgtc 120
cgttcgcagc gtcacccgga tcttcgccgc tacccttgtg ggccccccgg cgacgcttcc 180
tgctccgccc ctaagtcggg aaggttcctt gcggttcgcg gcgtgccgga cgtgacaaac 240
ggaagccgca cgtctcacta gtaccctcgc agacggacag cgccagggag caatggcagc 300
gcgccgaccg cgatgggctg tggccaatag cggctgctca gcagggcgcg ccgagagcag 360
cggccgggaa ggggcggtgc gggaggcggg gtgtggggcg gtagtgtggg ccctgttcct 420
gcccgcgcgg tgttccgcat tctgcaagcc tccggagcgc acgtcggcag tcggctccct 480
cgttgaccga atcaccgacc tctctcccca gggggatccc ccgggctgca ggaattcatg 540
tccgactcgt gggtcccgaa ctccgcctcg ggccaggacc cagggggccg ccggagggcc 600
tgggccgagc tgctggcggg aagggtcaag agggaaaaat ataatcctga aagggcacag 660
aaattaaagg aatcagctgt gcgcctcctg cgaagccatc aggacctgaa tgccctttttg 720 cttgaggtag aaggtccact gtgtaaaaaa ttgtctctca gcaaagtgat tgactgtgac 780
agttctgagg cctatgctaa tcattctagt tcatttatag gctctgcttt gcaggatcaa 840

```
gcctcaaggc tgggggttcc cgtgggtatt ctctcagccg ggatggttgc ctctagcgtg    900
ggacagatct gcacggctcc agcggagacc agtcaccctg tgctgctgac tgtggagcag    960
agaaagaagc tgtcttccct gttagagttt gctcagtatt tattggcaca cagtatgttc   1020
tcccgtcttt ccttctgtca agaattatgg aaaatacaga gttctttgtt gcttgaagcg   1080
gtgtggcatc ttcacgtaca aggcattgtg agcctgcaag agctgctgga aagccatccc   1140
gacatgcatg ctgtgggatc gtggctcttc aggaatctgt gctgcctttg tgaacagatg   1200
gaagcatcct gccagcatgc tgacgtcgcc agggccatgc tttctgattt tgttcaaatg   1260
tttgttttga ggggatttca gaaaaactca gatctgagaa gaactgtgga gcctgaaaaa   1320
atgccgcagg tcacggttga tgtactgcag agaatgctga tttttgcact tgacgctttg   1380
gctgctggag tacaggagga gtcctccact cacaagatcg tgaggtgctg gttcggagtg   1440
ttcagtggac acacgcttgg cagtgtaatt tccacagatc ctctgaagag gttcttcagt   1500
catacccctga ctcagatact cactcacagc cctgtgctga aagcatctga tgctgttcag   1560
atgcagagag agtggagctt tgcgcggaca caccctctgc tcacctcact gtaccgcagg   1620
ctctttgtga tgctgagtgc agaggagttg gttggccatt tgcaagaagt tctggaaacg   1680
caggaggttc actggcagag agtgctctcc tttgtgtctg ccctggttgt ctgctttcca   1740
gaagcgcagc agctgcttga agactgggtg gcgcgtttga tggcccaggc attcgagagc   1800
tgccagctgg acagcatggt cactgcgttc ctggttgtgc gccaggcagc actggagggc   1860
ccctctgcgt tcctgtcata tgcagactgg ttcaaggcct cctttgggag cacacgaggc   1920
taccatggct gcagcaagaa ggccctggtc ttcctgttta cgttcttgtc agaactcgtg   1980
ccttttgagt ctccccggta cctgcaggtg cacattctcc acccacccct ggttcccagc   2040
aagtaccgct ccctcctcac agactacatc tcattggcca agacacggct ggccgacctc   2100
aaggtttcta tagaaaacat gggactctac gaggatttgt catcagctgg ggacattact   2160
gagccccaca gccaagctct tcaggatgtt gaaaaggcca tcatggtgtt tgagcatacg   2220
gggaacatcc cagtcaccgt catggaggcc agcatattca ggaggcctta ctacgtgtcc   2280
cacttcctcc ccgccctgct cacacctcga gtgctcccca aagtccctga ctcccgtgtg   2340
gcgtttatag agtctctgaa gagagcagat aaaatccccc catctctgta ctccacctac   2400
tgccaggcct gctctgctgc tgaagagaag ccagaagatg cagccctggg agtgagggca   2460
gaacccaact ctgctgagga gcccctggga cagctcacag ctgcactggg agagctgaga   2520
gcctccatga cagaccccag ccagcgtgat gttatatcgg cacaggtggc agtgatttct   2580
gaaagactga gggctgtcct gggccacaat gaggatgaca gcagcgttga gatatcaaag   2640
attcagctca gcatcaacac gccgagactg gagccacggg aacacattgc tgtggacctc   2700
ctgctgacgt ctttctgtca gaacctgatg gctgcctcca gtgtcgctcc cccggagagg   2760
cagggtccct gggctgccct cttcgtgagg accatgtgtg gacgtgtgct ccctgcagtg   2820
ctcacccggc tctgccagct gctccgtcac cagggcccga gcctgagtgc cccacatgtg   2880
ctggggttgg ctgccctggc cgtgcacctg ggtgagtcca ggtctgcgct cccagaggtg   2940
gatgtgggtc ctcctgcacc tggtgctggc cttcctgtcc ctgcgctctt tgacagcctc   3000
ctgacctgta ggacgaggga ttccttgttc ttctgcctga aattttgtac agcagcaatt   3060
tcttactctc tctgcaagtt ttcttcccag tcacgagata ctttgtgcag ctgcttatct   3120
ccaggcctta ttaaaaagtt tcagttcctc atgttcagat tgttctcaga ggcccgacag   3180
```

-continued

```
cctctttctg aggaggacgt agccagcctt tcctggagac ccttgcacct tccttctgca   3240
gactggcaga gagctgccct ctctctctgg acacacagaa ccttccgaga ggtgttgaaa   3300
gaggaagatg ttcacttaac ttaccaagac tggttacacc tggagctgga aattcaacct   3360
gaagctgatg ctctttcaga tactgaacgg caggacttcc accagtgggc gatccatgag   3420
cactttctcc ctgagtcctc ggcttcaggg ggctgtgacg gagacctgca ggctgcgtgt   3480
accattcttg tcaacgcact gatggatttc caccaaagct caaggagtta tgaccactca   3540
gaaaattctg atttggtctt tggtggccgc acaggaaatg aggatattat ttccagattg   3600
caggagatgg tagctgacct ggagctgcag caagacctca tagtgcctct cggccacacc   3660
ccttcccagg agcacttcct ctttgagatt ttccgcagac ggctccaggc tctgacaagc   3720
gggtggagcg tggctgccag ccttcagaga cagagggagc tgctaatgta caaacggatc   3780
ctcctccgcc tgccttcgtc tgtcctctgc ggcagcagct tccaggcaga acagcccatc   3840
actgccagat gcgagcagtt cttccacttg gtcaactctg agatgagaaa cttctgctcc   3900
cacggaggtg ccctgacaca ggacatcact gcccacttct tcaggggcct cctgaacgcc   3960
tgtctgcgga gcagagaccc ctccctgatg gtcgacttca tactggccaa gtgccagacg   4020
aaatgcccct taattttgac ctctgctctg gtgtggtggc cgagcctgga gcctgtgctg   4080
ctctgccggt ggaggagaca ctgccagagc ccgctgcccc gggaactgca gaagctacaa   4140
gaaggccggc agtttgccag cgatttcctc tcccctgagg ctgcctcccc agcacccaac   4200
ccggactggc tctcagctgc tgcactgcac tttgcgattc aacaagtcag ggaagaaaac   4260
atcaggaagc agctaaagaa gctggactgc gagagagagg agctattggt tttcctttc    4320
ttcttctcct tgatgggcct gctgtcgtca catctgacct caaatagcac cacagacctg   4380
ccaaaggctt tccacgtttg tgcagcaatc ctcgagtgtt tagagaagag gaagatatcc   4440
tggctggcac tctttcagtt gacagagagt gacctcaggc tggggcggct cctcctccgt   4500
gtggccccgg atcagcacac caggctgctg cctttcgctt tttacagtct tctctcctac   4560
ttccatgaag acgcggccat cagggaagag gccttcctgc atgttgctgt ggacatgtac   4620
ttgaagctgg tccagctctt cgtggctggg gatacaagca cagtttcacc tccagctggc   4680
aggagcctgg agctcaaggg tcagggcaac cccgtggaac tgataacaaa agctcgtctt   4740
tttctgctgc agttaatacc tcggtgcccg aaaaagagct tctcacacgt ggcagagctg   4800
ctggctgatc gtggggactg cgacccagag gtgagcgccg ccctccagag cagacagcag   4860
gctgcccctg acgctgacct gtcccaggag cctcatctct tctgatgaga attcgatatc   4920
aagcttatcg ataccgtcga atcccccggg ctgcaggaat tcgagcatct taccgccatt   4980
tattcccata tttgttctgt ttttcttgat ttgggtatac atttaaatgt taataaaaca   5040
aaatggtggg gcaatcattt acatttttag ggatatgtaa ttactagttc aggtgtattg   5100
ccacaagaca aacatgttaa gaaactttcc cgttatttac gctctgttcc tgttaatcaa   5160
cctctggatt acaaaatttg tgaaagattg actgatattc ttaactatgt tgctcctttt   5220
acgctgtgtg gatatgctgc tttaatgcct ctgtatcatg ctattgcttc ccgtacggct   5280
ttcgttttct cctccttgta taaatcctgg ttgctgtctc tttatgagga gttgtggccc   5340
gttgtccgtc aacgtggcgt ggtgtgctct gtgtttgctg acgcaacccc cactggctgg   5400
ggcattgcca ccacctgtca actcctttct gggactttcg ctttccccct cccgatcgcc   5460
acggcagaac tcatcgccgc ctgccttgcc cgctgctgga caggggctag gttgctgggc   5520
actgataatt ccgtggtgtt gtcggggaag ggcc                               5554
```

<210> SEQ ID NO 2
<211> LENGTH: 1455
<212> TYPE: PRT
<213> ORGANISM: Homo sapiens

<400> SEQUENCE: 2

```
Met Ser Asp Ser Trp Val Pro Asn Ser Ala Ser Gly Gln Asp Pro Gly
1               5                   10                  15

Gly Arg Arg Arg Ala Trp Ala Glu Leu Leu Ala Gly Arg Val Lys Arg
            20                  25                  30

Glu Lys Tyr Asn Pro Glu Arg Ala Gln Lys Leu Lys Glu Ser Ala Val
        35                  40                  45

Arg Leu Leu Arg Ser His Gln Asp Leu Asn Ala Leu Leu Leu Glu Val
    50                  55                  60

Glu Gly Pro Leu Cys Lys Lys Leu Ser Leu Ser Lys Val Ile Asp Cys
65                  70                  75                  80

Asp Ser Ser Glu Ala Tyr Ala Asn His Ser Ser Ser Phe Ile Gly Ser
                85                  90                  95

Ala Leu Gln Asp Gln Ala Ser Arg Leu Gly Val Pro Val Gly Ile Leu
            100                 105                 110

Ser Ala Gly Met Val Ala Ser Ser Val Gly Gln Ile Cys Thr Ala Pro
        115                 120                 125

Ala Glu Thr Ser His Pro Val Leu Leu Thr Val Glu Gln Arg Lys Lys
    130                 135                 140

Leu Ser Ser Leu Leu Glu Phe Ala Gln Tyr Leu Leu Ala His Ser Met
145                 150                 155                 160

Phe Ser Arg Leu Ser Phe Cys Gln Glu Leu Trp Lys Ile Gln Ser Ser
                165                 170                 175

Leu Leu Leu Glu Ala Val Trp His Leu His Val Gln Gly Ile Val Ser
            180                 185                 190

Leu Gln Glu Leu Leu Glu Ser His Pro Asp Met His Ala Val Gly Ser
        195                 200                 205

Trp Leu Phe Arg Asn Leu Cys Cys Leu Cys Glu Gln Met Glu Ala Ser
    210                 215                 220

Cys Gln His Ala Asp Val Ala Arg Ala Met Leu Ser Asp Phe Val Gln
225                 230                 235                 240

Met Phe Val Leu Arg Gly Phe Gln Lys Asn Ser Asp Leu Arg Arg Thr
                245                 250                 255

Val Glu Pro Glu Lys Met Pro Gln Val Thr Val Asp Val Leu Gln Arg
            260                 265                 270

Met Leu Ile Phe Ala Leu Asp Ala Leu Ala Ala Gly Val Gln Glu Glu
        275                 280                 285

Ser Ser Thr His Lys Ile Val Arg Cys Trp Phe Gly Val Phe Ser Gly
    290                 295                 300

His Thr Leu Gly Ser Val Ile Ser Thr Asp Pro Leu Lys Arg Phe Phe
305                 310                 315                 320

Ser His Thr Leu Thr Gln Ile Leu Thr His Ser Pro Val Leu Lys Ala
                325                 330                 335

Ser Asp Ala Val Gln Met Gln Arg Glu Trp Ser Phe Ala Arg Thr His
            340                 345                 350

Pro Leu Leu Thr Ser Leu Tyr Arg Arg Leu Phe Val Met Leu Ser Ala
        355                 360                 365

Glu Glu Leu Val Gly His Leu Gln Glu Val Leu Glu Thr Gln Glu Val
```

-continued

```
    370                 375                 380

His Trp Gln Arg Val Leu Ser Phe Val Ser Ala Leu Val Val Cys Phe
385                 390                 395                 400

Pro Glu Ala Gln Gln Leu Leu Glu Asp Trp Val Ala Arg Leu Met Ala
                405                 410                 415

Gln Ala Phe Glu Ser Cys Gln Leu Asp Ser Met Val Thr Ala Phe Leu
            420                 425                 430

Val Val Arg Gln Ala Ala Leu Glu Gly Pro Ser Ala Phe Leu Ser Tyr
        435                 440                 445

Ala Asp Trp Phe Lys Ala Ser Phe Gly Ser Thr Arg Gly Tyr His Gly
    450                 455                 460

Cys Ser Lys Lys Ala Leu Val Phe Leu Phe Thr Phe Leu Ser Glu Leu
465                 470                 475                 480

Val Pro Phe Glu Ser Pro Arg Tyr Leu Gln Val His Ile Leu His Pro
                485                 490                 495

Pro Leu Val Pro Ser Lys Tyr Arg Ser Leu Leu Thr Asp Tyr Ile Ser
            500                 505                 510

Leu Ala Lys Thr Arg Leu Ala Asp Leu Lys Val Ser Ile Glu Asn Met
        515                 520                 525

Gly Leu Tyr Glu Asp Leu Ser Ser Ala Gly Asp Ile Thr Glu Pro His
    530                 535                 540

Ser Gln Ala Leu Gln Asp Val Glu Lys Ala Ile Met Val Phe Glu His
545                 550                 555                 560

Thr Gly Asn Ile Pro Val Thr Val Met Glu Ala Ser Ile Phe Arg Arg
                565                 570                 575

Pro Tyr Tyr Val Ser His Phe Leu Pro Ala Leu Leu Thr Pro Arg Val
            580                 585                 590

Leu Pro Lys Val Pro Asp Ser Arg Val Ala Phe Ile Glu Ser Leu Lys
        595                 600                 605

Arg Ala Asp Lys Ile Pro Pro Ser Leu Tyr Ser Thr Tyr Cys Gln Ala
    610                 615                 620

Cys Ser Ala Ala Glu Glu Lys Pro Glu Asp Ala Ala Leu Gly Val Arg
625                 630                 635                 640

Ala Glu Pro Asn Ser Ala Glu Glu Pro Leu Gly Gln Leu Thr Ala Ala
                645                 650                 655

Leu Gly Glu Leu Arg Ala Ser Met Thr Asp Pro Ser Gln Arg Asp Val
            660                 665                 670

Ile Ser Ala Gln Val Ala Val Ile Ser Glu Arg Leu Arg Ala Val Leu
        675                 680                 685

Gly His Asn Glu Asp Asp Ser Ser Val Glu Ile Ser Lys Ile Gln Leu
    690                 695                 700

Ser Ile Asn Thr Pro Arg Leu Glu Pro Arg Glu His Ile Ala Val Asp
705                 710                 715                 720

Leu Leu Leu Thr Ser Phe Cys Gln Asn Leu Met Ala Ala Ser Ser Val
                725                 730                 735

Ala Pro Pro Glu Arg Gln Gly Pro Trp Ala Ala Leu Phe Val Arg Thr
            740                 745                 750

Met Cys Gly Arg Val Leu Pro Ala Val Leu Thr Arg Leu Cys Gln Leu
        755                 760                 765

Leu Arg His Gln Gly Pro Ser Leu Ser Ala Pro His Val Leu Gly Leu
    770                 775                 780

Ala Ala Leu Ala Val His Leu Gly Glu Ser Arg Ser Ala Leu Pro Glu
785                 790                 795                 800
```

-continued

```
Val Asp Val Gly Pro Pro Ala Pro Gly Ala Gly Leu Pro Val Pro Ala
                805                 810                 815

Leu Phe Asp Ser Leu Leu Thr Cys Arg Thr Arg Asp Ser Leu Phe Phe
            820                 825                 830

Cys Leu Lys Phe Cys Thr Ala Ala Ile Ser Tyr Ser Leu Cys Lys Phe
        835                 840                 845

Ser Ser Gln Ser Arg Asp Thr Leu Cys Ser Cys Leu Ser Pro Gly Leu
    850                 855                 860

Ile Lys Lys Phe Gln Phe Leu Met Phe Arg Leu Phe Ser Glu Ala Arg
865                 870                 875                 880

Gln Pro Leu Ser Glu Glu Asp Val Ala Ser Leu Ser Trp Arg Pro Leu
                885                 890                 895

His Leu Pro Ser Ala Asp Trp Gln Arg Ala Ala Leu Ser Leu Trp Thr
            900                 905                 910

His Arg Thr Phe Arg Glu Val Leu Lys Glu Glu Asp Val His Leu Thr
        915                 920                 925

Tyr Gln Asp Trp Leu His Leu Glu Leu Glu Ile Gln Pro Glu Ala Asp
    930                 935                 940

Ala Leu Ser Asp Thr Glu Arg Gln Asp Phe His Gln Trp Ala Ile His
945                 950                 955                 960

Glu His Phe Leu Pro Glu Ser Ser Ala Ser Gly Gly Cys Asp Gly Asp
                965                 970                 975

Leu Gln Ala Ala Cys Thr Ile Leu Val Asn Ala Leu Met Asp Phe His
            980                 985                 990

Gln Ser Ser Arg Ser Tyr Asp His  Ser Glu Asn Ser Asp  Leu Val Phe
        995                 1000                1005

Gly Gly  Arg Thr Gly Asn Glu  Asp Ile Ile Ser Arg  Leu Gln Glu
    1010                 1015                 1020

Met Val  Ala Asp Leu Glu Leu  Gln Gln Asp Leu Ile  Val Pro Leu
    1025                 1030                 1035

Gly His  Thr Pro Ser Gln Glu  His Phe Leu Phe Glu  Ile Phe Arg
    1040                 1045                 1050

Arg Arg  Leu Gln Ala Leu Thr  Ser Gly Trp Ser Val  Ala Ala Ser
    1055                 1060                 1065

Leu Gln  Arg Gln Arg Glu Leu  Leu Met Tyr Lys Arg  Ile Leu Leu
    1070                 1075                 1080

Arg Leu  Pro Ser Ser Val Leu  Cys Gly Ser Ser Phe  Gln Ala Glu
    1085                 1090                 1095

Gln Pro  Ile Thr Ala Arg Cys  Glu Gln Phe Phe His  Leu Val Asn
    1100                 1105                 1110

Ser Glu  Met Arg Asn Phe Cys  Ser His Gly Gly Ala  Leu Thr Gln
    1115                 1120                 1125

Asp Ile  Thr Ala His Phe Phe  Arg Gly Leu Leu Asn  Ala Cys Leu
    1130                 1135                 1140

Arg Ser  Arg Asp Pro Ser Leu  Met Val Asp Phe Ile  Leu Ala Lys
    1145                 1150                 1155

Cys Gln  Thr Lys Cys Pro Leu  Ile Leu Thr Ser Ala  Leu Val Trp
    1160                 1165                 1170

Trp Pro  Ser Leu Glu Pro Val  Leu Leu Cys Arg Trp  Arg Arg His
    1175                 1180                 1185

Cys Gln  Ser Pro Leu Pro Arg  Glu Leu Gln Lys Leu  Gln Glu Gly
    1190                 1195                 1200
```

-continued

```
Arg Gln Phe Ala Ser Asp Phe  Leu Ser Pro Glu Ala  Ala Ser Pro
    1205             1210             1215

Ala Pro Asn Pro Asp Trp Leu  Ser Ala Ala Ala Leu  His Phe Ala
    1220             1225             1230

Ile Gln Gln Val Arg Glu Glu  Asn Ile Arg Lys Gln  Leu Lys Lys
    1235             1240             1245

Leu Asp Cys Glu Arg Glu Glu  Leu Leu Val Phe Leu  Phe Phe Phe
    1250             1255             1260

Ser Leu Met Gly Leu Leu Ser  Ser His Leu Thr Ser  Asn Ser Thr
    1265             1270             1275

Thr Asp Leu Pro Lys Ala Phe  His Val Cys Ala Ala  Ile Leu Glu
    1280             1285             1290

Cys Leu Glu Lys Arg Lys Ile  Ser Trp Leu Ala Leu  Phe Gln Leu
    1295             1300             1305

Thr Glu Ser Asp Leu Arg Leu  Gly Arg Leu Leu Leu  Arg Val Ala
    1310             1315             1320

Pro Asp Gln His Thr Arg Leu  Leu Pro Phe Ala Phe  Tyr Ser Leu
    1325             1330             1335

Leu Ser Tyr Phe His Glu Asp  Ala Ala Ile Arg Glu  Glu Ala Phe
    1340             1345             1350

Leu His Val Ala Val Asp Met  Tyr Leu Lys Leu Val  Gln Leu Phe
    1355             1360             1365

Val Ala Gly Asp Thr Ser Thr  Val Ser Pro Pro Ala  Gly Arg Ser
    1370             1375             1380

Leu Glu Leu Lys Gly Gln Gly  Asn Pro Val Glu Leu  Ile Thr Lys
    1385             1390             1395

Ala Arg Leu Phe Leu Leu Gln  Leu Ile Pro Arg Cys  Pro Lys Lys
    1400             1405             1410

Ser Phe Ser His Val Ala Glu  Leu Leu Ala Asp Arg  Gly Asp Cys
    1415             1420             1425

Asp Pro Glu Val Ser Ala Ala  Leu Gln Ser Arg Gln  Gln Ala Ala
    1430             1435             1440

Pro Asp Ala Asp Leu Ser Gln  Glu Pro His Leu Phe
    1445             1450             1455
```

```
<210> SEQ ID NO 3
<211> LENGTH: 3903
<212> TYPE: DNA
<213> ORGANISM: Artificial Sequence
<220> FEATURE:
<223> OTHER INFORMATION: pCCL-ChimhCD18W-82-RO vector sequence

<400> SEQUENCE: 3

cgcgtctgcc agctttcttg ctttgctgga gtattctgga atttgatggg ttgagggttc      60

tggacacaat gccccaagcc ccttccttgt tgtgctgggt tcctatttct gctctcggca     120

ctgacttagc agctgctcaa gagctcacca tgttggcttg gattacacgg tctcacccac     180

atctccggca gtttgtgggc aaacttcctg agcagccttg ggtgatgaaa cctttcatgg     240

tagcaggaga atgggactgt gaattctcaa tcccctgtcc ccaccccttc cttcctctct     300

cagggccttg ctgtctagga ggagggagca cagcagcaac tgactgggca gcctttcagg     360

aaaggctagc ccgggctcga tcgagaagct tgataattcc gtgaggtggg gagggctggg     420

accagggttc cctctttctc ttctgcggtg gccctggcct ggtgctagga ctgcgcgcct     480

cccctcagta cccgcggaca ccctgggctt ccctgggccc agcatctgcc tggggcctcg     540
```

-continued

```
ccctgggctc cccctcctga cccccacctt gcgccccttc ccggtgttcc cggggcgctg    600
ccgggccctg gggcctgcgg ggcgcgggcg gctcttggct gggccattct ttcccggccc    660
cctcctccct tccgtttccg tggccgtgcg gccggctaga ggctgcggcc cagcgcggag    720
caggggggct ggcaggcgtc ggggcggtcg ggccggtccc gcccgcccct tcccctccac    780
aggcccgccc cggggcctgg gccaactgaa accgcgggag gaggaagcgc ggaatcagga    840
actggccggg gtccgcaccg ggcctgagtc ggtccgaggc cgtcccagga gcagctgccc    900
gaagggcgaa ttgggggatc ccccgggcta atgccaactt tgtacaaaaa agcaggctcc    960
accatgctgg gcctgcgccc cccacttctc gccctggtgg ggctgctctc cctcgggtgc   1020
gtcctctctc aggagtgcac gaagttcaag gtcagcagct gccgggaatg catcgagtcg   1080
gggcccggct gcacctggtg ccagaagctg aacttcacag ggccgggga tcctgactcc   1140
attcgctgcg acacccggcc acagctgctc atgaggggct gtgcggctga cgacatcatg   1200
gaccccacaa gcctcgctga aacccaggaa gaccacaatg gggccagaa gcagctgtcc   1260
ccacaaaaag tgacgcttta cctgcgacca ggccaggcag cagcgttcaa cgtgaccttc   1320
cggcgggcca agggctaccc catcgacctg tactatctga tggacctctc ctactccatg   1380
cttgatgacc tcaggaatgt caagaagcta ggtggcgacc tgctccgggc cctcaacgag   1440
atcaccgagt ccggccgcat tggcttcggg tccttcgtgg acaagaccgt gctgccgttc   1500
gtgaacacgc accctgataa gctgcgaaac ccatgcccca acaaggagaa agagtgccag   1560
cccccgtttg ccttcaggca cgtgctgaag ctgaccaaca actccaacca gtttcagacc   1620
gaggtcggga agcagctgat ttccggaaac ctggatgcac ccgagggtgg gctggacgcc   1680
atgatgcagg tcgccgcctg cccggaggaa atcggctggc gcaacgtcac gcggctgctg   1740
gtgtttgcca ctgatgacgg cttccatttc gcgggcgacg ggaagctggg cgccatcctg   1800
acccccaacg acggccgctg tcacctggag gacaacttgt acaagaggag caacgaattc   1860
gactacccat cggtgggcca gctggcgcac aagctggctg aaaacaacat ccagcccatc   1920
ttcgcggtga ccagtaggat ggtgaagacc tacgagaaac tcaccgagat catccccaag   1980
tcagccgtgg gggagctgtc tgaggactcc agcaatgtgg tccatctcat taagaatgct   2040
tacaataaac tctcctccag ggtattcctg gatcacaacg ccctccccga caccctgaaa   2100
gtcacctacg actccttctg cagcaatgga gtgacgcaca ggaaccagcc cagaggtgac   2160
tgtgatggcg tgcagatcaa tgtcccgatc accttccagg tgaaggtcac ggccacagag   2220
tgcatccagg agcagtcgtt tgtcatccgg gcgctgggct tcacggacat agtgaccgtg   2280
caggtccttc cccagtgtga gtgccggtgc cgggaccaga gcagagaccg cagcctctgc   2340
catggcaagg gcttcttgga gtgcggcatc tgcaggtgtg acactggcta cattgggaaa   2400
aactgtgagt gccagacaca gggccggagc agccaggagc tggaaggaag ctgccggaag   2460
gacaacaact ccatcatctg ctcagggctg ggggactgtg tctgcgggca gtgcctgtgc   2520
cacaccagcg acgtccccgg caagctgata tacgggcagt actgcgagtg tgacaccatc   2580
aactgtgagc gctacaacgg ccaggtctgc ggcggcccgg ggagggggct ctgcttctgc   2640
gggaagtgcc gctgccaccc gggctttgag ggctcagcgt gccagtgcga gaggaccact   2700
gagggctgcc tgaacccgcg gcgtgttgag tgtagtggtc gtggccggtg ccgctgcaac   2760
gtatgcgagt gccattcagg ctaccagctg cctctgtgcc aggagtgccc cggctgcccc   2820
tcaccctgtg gcaagtacat ctcctgcgcc gagtgcctga agttcgaaaa gggccccttt   2880
gggaagaact gcagcgcggc gtgtccgggc ctgcagctgt cgaacaaccc cgtgaagggc   2940
```

-continued

```
aggacctgca aggagaggga ctcagagggc tgctgggtgg cctacacgct ggagcagcag   3000

gacgggatgg accgctacct catctatgtg gatgagagcc gagagtgtgt ggcaggcccc   3060

aacatcgccg ccatcgtcgg gggcaccgtg gcaggcatcg tgctgatcgg cattctcctg   3120

ctggtcatct ggaaggctct gatccacctg agcgacctcc gggagtacag gcgctttgag   3180

aaggagaagc tcaagtccca gtggaacaat gataatcccc ttttcaagag cgccaccacg   3240

acggtcatga accccaagtt tgctgagagt taggacccag ctttcttgta caaagttggc   3300

attaggaatt cgagcatctt accgccattt attcccatat ttgttctgtt tttcttgatt   3360

tgggtataca tttaaatgtt aataaaacaa aatggtgggg caatcattta catttttagg   3420

gatatgtaat tactagttca ggtgtattgc cacaagacaa acatgttaag aaactttccc   3480

gttatttacg ctctgttcct gttaatcaac ctctggatta caaaatttgt gaaagattga   3540

ctgatattct taactatgtt gctcctttta cgctgtgtgg atatgctgct ttaatgcctc   3600

tgtatcatgc tattgcttcc cgtacggctt tcgttttctc ctccttgtat aaatcctggt   3660

tgctgtctct ttatgaggag ttgtggcccg ttgtccgtca acgtggcgtg gtgtgctctg   3720

tgtttgctga cgcaaccccc actggctggg gcattgccac cacctgtcaa ctcctttctg   3780

ggactttcgc tttccccctc ccgatcgcca cggcagaact catcgccgcc tgccttgccc   3840

gctgctggac aggggctagg ttgctgggca ctgataattc cgtggtgttg tcggggaagg   3900

gcc                                                                 3903


<210> SEQ ID NO 4
<211> LENGTH: 769
<212> TYPE: PRT
<213> ORGANISM: Homo sapiens

<400> SEQUENCE: 4

Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
            20                  25                  30

Cys Arg Glu Cys Ile Glu Ser Gly Pro Gly Cys Thr Trp Cys Gln Lys
        35                  40                  45

Leu Asn Phe Thr Gly Pro Gly Asp Pro Asp Ser Ile Arg Cys Asp Thr
    50                  55                  60

Arg Pro Gln Leu Leu Met Arg Gly Cys Ala Ala Asp Asp Ile Met Asp
65                  70                  75                  80

Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
            100                 105                 110

Ala Ala Phe Asn Val Thr Phe Arg Arg Ala Lys Gly Tyr Pro Ile Asp
        115                 120                 125

Leu Tyr Tyr Leu Met Asp Leu Ser Tyr Ser Met Leu Asp Asp Leu Arg
    130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
            180                 185                 190
```

-continued

```
Asn Lys Glu Lys Glu Cys Gln Pro Pro Phe Ala Phe Arg His Val Leu
        195                 200                 205

Lys Leu Thr Asn Asn Ser Asn Gln Phe Gln Thr Glu Val Gly Lys Gln
    210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Arg Ser Asn Glu Phe Asp Tyr Pro Ser Val
    290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
            340                 345                 350

Val His Leu Ile Lys Asn Ala Tyr Asn Lys Leu Ser Ser Arg Val Phe
        355                 360                 365

Leu Asp His Asn Ala Leu Pro Asp Thr Leu Lys Val Thr Tyr Asp Ser
    370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
            420                 425                 430

Phe Thr Asp Ile Val Thr Val Gln Val Leu Pro Gln Cys Glu Cys Arg
        435                 440                 445

Cys Arg Asp Gln Ser Arg Asp Arg Ser Leu Cys His Gly Lys Gly Phe
    450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
            500                 505                 510

Val Cys Gly Gln Cys Leu Cys His Thr Ser Asp Val Pro Gly Lys Leu
        515                 520                 525

Ile Tyr Gly Gln Tyr Cys Glu Cys Asp Thr Ile Asn Cys Glu Arg Tyr
    530                 535                 540

Asn Gly Gln Val Cys Gly Gly Pro Gly Arg Gly Leu Cys Phe Cys Gly
545                 550                 555                 560

Lys Cys Arg Cys His Pro Gly Phe Glu Gly Ser Ala Cys Gln Cys Glu
                565                 570                 575

Arg Thr Thr Glu Gly Cys Leu Asn Pro Arg Arg Val Glu Cys Ser Gly
            580                 585                 590

Arg Gly Arg Cys Arg Cys Asn Val Cys Glu Cys His Ser Gly Tyr Gln
        595                 600                 605

Leu Pro Leu Cys Gln Glu Cys Pro Gly Cys Pro Ser Pro Cys Gly Lys
```

-continued

```
    610                 615                 620

Tyr Ile Ser Cys Ala Glu Cys Leu Lys Phe Glu Lys Gly Pro Phe Gly
625                 630                 635                 640

Lys Asn Cys Ser Ala Ala Cys Pro Gly Leu Gln Leu Ser Asn Asn Pro
                645                 650                 655

Val Lys Gly Arg Thr Cys Lys Glu Arg Asp Ser Glu Gly Cys Trp Val
            660                 665                 670

Ala Tyr Thr Leu Glu Gln Gln Asp Gly Met Asp Arg Tyr Leu Ile Tyr
        675                 680                 685

Val Asp Glu Ser Arg Glu Cys Val Ala Gly Pro Asn Ile Ala Ala Ile
    690                 695                 700

Val Gly Gly Thr Val Ala Gly Ile Val Leu Ile Gly Ile Leu Leu Leu
705                 710                 715                 720

Val Ile Trp Lys Ala Leu Ile His Leu Ser Asp Leu Arg Glu Tyr Arg
                725                 730                 735

Arg Phe Glu Lys Glu Lys Leu Lys Ser Gln Trp Asn Asn Asp Asn Pro
            740                 745                 750

Leu Phe Lys Ser Ala Thr Thr Thr Val Met Asn Pro Lys Phe Ala Glu
        755                 760                 765

Ser
```

<210> SEQ ID NO 5
<211> LENGTH: 2890
<212> TYPE: DNA
<213> ORGANISM: Artificial Sequence
<220> FEATURE:
<223> OTHER INFORMATION: pCCL-PGK-coRPKW-82-RO vector sequence

<400> SEQUENCE: 5

```
ggggttgggg ttgcgccttt tccaaggcag ccctgggttt gcgcagggac gcggctgctc     60

tgggcgtggt tccgggaaac gcagcggcgc cgaccctggg tctcgcacat tcttcacgtc    120

cgttcgcagc gtcacccgga tcttcgccgc tacccttgtg ggcccccccgg cgacgcttcc    180

tgctccgccc ctaagtcggg aaggttcctt gcggttcgcg gcgtgccgga cgtgacaaac    240

ggaagccgca cgtctcacta gtaccctcgc agacggacag cgccagggag caatggcagc    300

gcgccgaccg cgatgggctg tggccaatag cggctgctca gcagggcgcg ccgagagcag    360

cggccgggaa ggggcggtgc gggaggcggg gtgtggggcg gtagtgtggg ccctgttcct    420

gcccgcgcgg tgttccgcat tctgcaagcc tccggagcgc acgtcggcag tcggctccct    480

cgttgaccga atcaccgacc tctctcccca gggggatccg tcgacaccgg tgccaccatg    540

agcatccagg aaaatatcag ctctctgcag ctgcggtcct gggtgtccaa gagccagaga    600

gacctggcca agagcatcct gatcggagcc cctggcggac cagccggata cctgagaagg    660

gctagcgtgg cccagctgac ccaggaactg ggcaccgcct tttccagca gcagcagctg    720

ccagccgcca tggccgacac ctttctggaa cacctgtgcc tgctggacat cgactctgag    780

cccgtggccg ccagaagcac cagcatcatt gccaccatcg gccctgccag cagaagcgtg    840

gagcggctga aagagatgat caaggccggc atgaatatcg cccggctgaa cttctcccac    900

ggcagccacg agtaccacgc agagagcatt gccaacgtcc gggaggccgt ggagagcttt    960

gccggcagcc ccctgagcta cagacccgtg gccattgccc tggacaccaa gggccccgag   1020

atcagaacag gaattctgca gggagggcct gagagcgagg tggagctggt gaagggcagc   1080

caagtgctgg tgaccgtgga ccccgccttc agaaccagag gcaacgccaa cacagtgtgg   1140
```

-continued

```
gtggactacc ccaacatcgt gcgggtggtg cctgtgggcg gcagaatcta catcgacgac   1200

ggcctgatca gcctggtggt gcagaagatc ggacctgagg gcctggtgac ccaggtcgag   1260

aatggcggcg tgctgggcag cagaaagggc gtgaatctgc caggcgccca ggtggacctg   1320

cctggcctgt ctgagcagga cgtgagagac ctgagatttg gcgtggagca cggcgtggac   1380

atcgtgttcg ccagcttcgt gcggaaggcc tctgatgtgg ccgccgtgag agccgctctg   1440

ggccctgaag gccacggcat caagatcatc agcaagatcg agaaccacga gggcgtgaag   1500

cggttcgacg agatcctgga agtgtccgac ggcatcatgg tggccagagg cgacctgggc   1560

atcgagatcc ccgccgagaa ggtgttcctg gcccagaaaa tgatgatcgg acggtgcaac   1620

ctggccggca aacctgtggt gtgcgccacc cagatgctgg aaagcatgat caccaagccc   1680

agacccacca gagccgagac aagcgacgtg gccaacgccg tgctggatgg cgctgactgc   1740

atcatgctgt ccggcgagac agccaagggc aacttccccg tggaggccgt gaagatgcag   1800

cacgccattg ccagagaagc cgaggccgcc gtgtaccacc ggcagctgtt cgaggaactg   1860

cggagagccg cccctctgag cagagatccc accgaagtga ccgccatcgg agccgtggaa   1920

gccgccttca agtgctgcgc cgctgcaatc atcgtgctga ccaccacagg cagaagcgcc   1980

cagctgctgt ccagatacag acccagagcc gccgtgatcg ccgtgacaag atccgcccag   2040

gccgctagac aggtccacct gtgcagaggc gtgttccccc tgctgtaccg ggagcctccc   2100

gaggccatct gggccgacga cgtggacaga cgggtgcagt tcggcatcga gagcggcaag   2160

ctgcggggct tcctgagagt gggcgacctg gtgatcgtgg tgacaggctg gcggcctggc   2220

agcggctaca ccaacatcat gagggtgctg tccatcagct gaccgcggtc tagaggatcc   2280

cccgggctgc aggaattcga gcatcttacc gccatttatt cccatatttg ttctgttttt   2340

cttgatttgg gtatacattt aaatgttaat aaaacaaaat ggtggggcaa tcatttacat   2400

ttttagggat atgtaattac tagttcaggt gtattgccac aagacaaaca tgttaagaaa   2460

ctttcccgtt atttacgctc tgttcctgtt aatcaacctc tggattacaa aatttgtgaa   2520

agattgactg atattcttaa ctatgttgct ccttttacgc tgtgtggata tgctgcttta   2580

atgcctctgt atcatgctat tgcttcccgt acggctttcg ttttctcctc cttgtataaa   2640

tcctggttgc tgtctcttta tgaggagttg tggcccgttg tccgtcaacg tggcgtggtg   2700

tgctctgtgt ttgctgacgc aacccccact ggctggggca ttgccaccac ctgtcaactc   2760

ctttctggga ctttcgcttt ccccctcccg atcgccacgg cagaactcat cgccgcctgc   2820

cttgcccgct gctggacagg ggctaggttg ctgggcactg ataattccgt ggtgttgtcg   2880

gggaagggcc                                                          2890
```

<210> SEQ ID NO 6
<211> LENGTH: 574
<212> TYPE: PRT
<213> ORGANISM: Homo sapiens

<400> SEQUENCE: 6

```
Met Ser Ile Gln Glu Asn Ile Ser Ser Leu Gln Leu Arg Ser Trp Val
1               5                   10                  15

Ser Lys Ser Gln Arg Asp Leu Ala Lys Ser Ile Leu Ile Gly Ala Pro
            20                  25                  30

Gly Gly Pro Ala Gly Tyr Leu Arg Arg Ala Ser Val Ala Gln Leu Thr
        35                  40                  45

Gln Glu Leu Gly Thr Ala Phe Phe Gln Gln Gln Leu Pro Ala Ala
    50                  55                  60
```

-continued

```
Met Ala Asp Thr Phe Leu Glu His Leu Cys Leu Leu Asp Ile Asp Ser
65                  70                  75                  80

Glu Pro Val Ala Ala Arg Ser Thr Ser Ile Ile Ala Thr Ile Gly Pro
                85                  90                  95

Ala Ser Arg Ser Val Glu Arg Leu Lys Glu Met Ile Lys Ala Gly Met
            100                 105                 110

Asn Ile Ala Arg Leu Asn Phe Ser His Gly Ser His Glu Tyr His Ala
        115                 120                 125

Glu Ser Ile Ala Asn Val Arg Glu Ala Val Glu Ser Phe Ala Gly Ser
    130                 135                 140

Pro Leu Ser Tyr Arg Pro Val Ala Ile Ala Leu Asp Thr Lys Gly Pro
145                 150                 155                 160

Glu Ile Arg Thr Gly Ile Leu Gln Gly Gly Pro Glu Ser Glu Val Glu
                165                 170                 175

Leu Val Lys Gly Ser Gln Val Leu Val Thr Val Asp Pro Ala Phe Arg
            180                 185                 190

Thr Arg Gly Asn Ala Asn Thr Val Trp Val Asp Tyr Pro Asn Ile Val
        195                 200                 205

Arg Val Val Pro Val Gly Gly Arg Ile Tyr Ile Asp Asp Gly Leu Ile
    210                 215                 220

Ser Leu Val Val Gln Lys Ile Gly Pro Glu Gly Leu Val Thr Gln Val
225                 230                 235                 240

Glu Asn Gly Gly Val Leu Gly Ser Arg Lys Gly Val Asn Leu Pro Gly
                245                 250                 255

Ala Gln Val Asp Leu Pro Gly Leu Ser Glu Gln Asp Val Arg Asp Leu
            260                 265                 270

Arg Phe Gly Val Glu His Gly Val Asp Ile Val Phe Ala Ser Phe Val
        275                 280                 285

Arg Lys Ala Ser Asp Val Ala Ala Val Arg Ala Ala Leu Gly Pro Glu
    290                 295                 300

Gly His Gly Ile Lys Ile Ile Ser Lys Ile Glu Asn His Glu Gly Val
305                 310                 315                 320

Lys Arg Phe Asp Glu Ile Leu Glu Val Ser Asp Gly Ile Met Val Ala
                325                 330                 335

Arg Gly Asp Leu Gly Ile Glu Ile Pro Ala Glu Lys Val Phe Leu Ala
            340                 345                 350

Gln Lys Met Met Ile Gly Arg Cys Asn Leu Ala Gly Lys Pro Val Val
        355                 360                 365

Cys Ala Thr Gln Met Leu Glu Ser Met Ile Thr Lys Pro Arg Pro Thr
    370                 375                 380

Arg Ala Glu Thr Ser Asp Val Ala Asn Ala Val Leu Asp Gly Ala Asp
385                 390                 395                 400

Cys Ile Met Leu Ser Gly Glu Thr Ala Lys Gly Asn Phe Pro Val Glu
                405                 410                 415

Ala Val Lys Met Gln His Ala Ile Ala Arg Glu Ala Glu Ala Ala Val
            420                 425                 430

Tyr His Arg Gln Leu Phe Glu Glu Leu Arg Arg Ala Ala Pro Leu Ser
        435                 440                 445

Arg Asp Pro Thr Glu Val Thr Ala Ile Gly Ala Val Glu Ala Ala Phe
    450                 455                 460

Lys Cys Cys Ala Ala Ala Ile Ile Val Leu Thr Thr Thr Gly Arg Ser
465                 470                 475                 480
```

Ala Gln Leu Leu Ser Arg Tyr Arg Pro Arg Ala Ala Val Ile Ala Val
485 490 495

Thr Arg Ser Ala Gln Ala Ala Arg Gln Val His Leu Cys Arg Gly Val
500 505 510

Phe Pro Leu Leu Tyr Arg Glu Pro Pro Glu Ala Ile Trp Ala Asp Asp
515 520 525

Val Asp Arg Arg Val Gln Phe Gly Ile Glu Ser Gly Lys Leu Arg Gly
530 535 540

Phe Leu Arg Val Gly Asp Leu Val Ile Val Val Thr Gly Trp Arg Pro
545 550 555 560

Gly Ser Gly Tyr Thr Asn Ile Met Arg Val Leu Ser Ile Ser
565 570

<210> SEQ ID NO 7
<211> LENGTH: 1233
<212> TYPE: DNA
<213> ORGANISM: Artificial Sequence
<220> FEATURE:
<223> OTHER INFORMATION: PKLR polynucloetide seqeunce

<400> SEQUENCE: 7
atggtctgct tcagactgtt ccctgtccct ggatctggtc tggtgcttgt gtgcttggtg 60
ctgggtgctg tgagatccta tgcccttgag ctgaacctga ctgactcaga aaatgccact 120
tgcctgtatg ccaagtggca gatgaacttc actgtgagat atgagactac caacaagacc 180
tacaagactg tgaccatctc agaccatggc actgtcacct acaatggatc aatctgtggt 240
gatgatcaga atggcccaaa gatagcagtg cagtttgggc ccggtttttc ctggattgct 300
aacttcacca aggcagcctc cacctacagc attgactcag tcagcttcag ctacaacact 360
ggggataaca ccaccttccc tgacgcagag gacaagggaa tccttactgt ggacgaactc 420
ctggcaatca gaatccccct taacgacctg ttcagatgca actccctttc aacccttgaa 480
aagaatgatg tggtgcaaca ctattgggac gtcctggtgc aagcctttgt gcagaatggg 540
acagtgagta ccaacgagtt cctctgtgac aaggacaaga ccagcactgt ggccccccact 600 atccacacca ctgtgcccag ccctaccact acccccaccc ctaaagagaa gccagaagct 660
ggaacctact cagtcaacaa tggaaatgac acatgcctcc ttgccaccat gggactgcag 720
ctgaacatca ctcaggacaa ggtggcctca gtgattaaca tcaaccctaa caccactcat 780
agcactggga gctgcagatc acatacagct ctgctgaggc tcaactcctc caccatcaag 840
tacctggact ttgtgtttgc tgtgaagaat gagaacaggt tctacctcaa ggaagtgaac 900
atttccatgt acctggtcaa tggttcagtg ttctctattg ccaacaacaa tctgagctac 960
tgggatgcac ccctgggatc ctcctacatg tgcaacaagg agcagactgt gagtgtgtca 1020
ggtgcttttc agatcaacac ttttgacctg agggtgcagc ccttcaatgt gactcaggga 1080
aagtactcca ctgcacaaga gtgttccttg gatgatgaca ctatcctcat ccccattatt 1140
gtgggagctg gactgtcagg attgattata gtgattgtga ttgcttatgt gattggaagg 1200
agaaagagct atgctggcta ccagaccctg taa 1233

<210> SEQ ID NO 8
<211> LENGTH: 1233
<212> TYPE: DNA
<213> ORGANISM: Artificial Sequence
<220> FEATURE:
<223> OTHER INFORMATION: PKLR polynucloetide seqeunce

<400> SEQUENCE: 8

-continued

```
atggtgtgct ttagactgtt tcctgtgcct ggttcagggc tggtcctggt ctgtctggtg     60
ctgggggctg tcagaagcta tgccttggag ctgaacctca ctgatagtga aaatgccact    120
tgtctgtatg ctaagtggca gatgaacttc actgtgagat atgaaaccac caacaagact    180
tacaaaacag tgaccatctc agatcatgga actgtgacct acaacggcag catttgtgga    240
gacgaccaga acggaccaaa aatcgctgtc caatttgggc ctggattctc ctggattgcc    300
aatttcacta aagctgcctc cacatattca attgactcag tgtccttctc ctacaacact    360
ggggacaaca ctactttccc tgatgctgaa gataagggaa tcttgacagt ggatgagctg    420
ctggctatca ggatcccttt gaatgacctg tttaggtgta attcactgag cactctggag    480
aagaacgacg tggtgcagca ctactgggac gtgctggtgc aggcctttgt gcagaacggc    540
actgtgtcca ccaacgaatt cctgtgtgat aaggacaaaa cttccactgt ggcacctaca    600
attcacacta ctgtgccttc acctaccacc actccaactc caaaggaaaa gcctgaagca    660
ggaacctact ctgtgaacaa tggcaatgat acctgtctgt tggccaccat gggcctccaa    720
ctgaacatta ctcaggacaa ggtggcctca gtgattaaca ttaaccccaa cactacccac    780
tccactggca gctgtagatc acacacagcc ttgctcagac tgaatagcag caccatcaag    840
tatttggatt ttgtgtttgc agtgaagaat gaaaacaggt tctacctgaa ggaagtcaac    900
atctcaatgt acctggtgaa cggctcagtg ttcagcattg ccaacaacaa cctctcctat    960
tgggacgctc cactggggag cagctacatg tgtaacaagg aacagactgt gtcagtgtca   1020
ggagccttcc agattaacac ctttgatctg agggtccaac cctttaatgt cactcaagga   1080
aagtatagca ctgcccagga gtgctccctg gatgatgaca ccattctgat tccaatcatt   1140
gtgggtgcag gactttctgg gcttattatt gtgattgtga ttgcctatgt gattggcaga   1200
aggaaatcct atgcagggta ccaaactctg taa                                 1233
```

<210> SEQ ID NO 9
<211> LENGTH: 1233
<212> TYPE: DNA
<213> ORGANISM: Artificial Sequence
<220> FEATURE:
<223> OTHER INFORMATION: PKLR polynucloetide seqeunce

<400> SEQUENCE: 9

```
atggtctgtt ttaggctgtt ccctgtccct ggttcaggac tggtcttagt gtgtctggtg     60
cttggagctg tcagaagcta tgccctggag ctgaacctga ctgactcaga aaatgccact    120
tgcctgtatg ccaagtggca gatgaacttc actgtcagat atgaaaccac caacaagacc    180
tataagactg tgaccatctc agaccatggc actgtgactt acaatgggtc aatttgtgga    240
gatgaccaga atggccctaa gatagctgtc cagtttggtc caggattcag ctggattgcc    300
aacttcacca aggcagccag cacctacagc attgactctg tgtccttctc ctacaacaca    360
ggagacaaca ccactttccc tgatgcagag gacaaaggta tcctgactgt ggatgagttg    420
ctggcaatca ggatcccact gaacgatctg ttcaggtgca actcactgtc cactctggaa    480
aagaatgatg tggtgcagca ctattgggat gtgctagtcc aggcctttgt ccagaatggg    540
actgtgtcaa ctaatgagtt cctgtgtgac aaggacaaga caagcactgt agcccccact    600
atccatacca cagtacctag ccccaccact actccaaccc ccaaggagaa gcctgaggct    660
ggcacctact cagtgaacaa tgggaatgac acctgtttgc tggccactat gggactccaa    720
ctgaacatca cccaggacaa agtggcctct gtgatcaata tcaatcccaa caccacccac    780
```

-continued agcactgggt cctgcagaag ccacactgcc ctcctgaggc tcaactcatc aactatcaag 840
tacttggatt ttgtgtttgc agtgaagaat gagaacagat tctacctcaa agaggtcaac 900
atttcaatgt acctggtgaa tgggagtgtg ttctccattg ctaacaacaa cctgagctac 960
tgggatgccc ctctgggctc ctcatacatg tgcaacaagg aacagactgt gagtgtgtca 1020
ggggccttcc agatcaacac ttttgacctg agagtgcagc cctttaatgt gacacaggga 1080
aagtacagca ctgctcagga gtgcagcctg gatgatgaca ctatcctgat ccctatcatt 1140
gtgggggcag gcctgtctgg actcattatt gtgattgtga ttgcctatgt gatagggaga 1200
aggaagtctt atgctggata ccagaccctg taa 1233

<210> SEQ ID NO 10
<211> LENGTH: 3384
<212> TYPE: DNA
<213> ORGANISM: Artificial Sequence
<220> FEATURE:
<223> OTHER INFORMATION: pRRL.PPT.EFS.tcirg1h.wpre vector sequence

<400> SEQUENCE: 10
ggctccggtg cccgtcagtg ggcagagcgc acatcgccca cagtccccga gaagttgggg 60
ggaggggtcg gcaattgaac cggtgcctag agaaggtggc gcggggtaaa ctgggaaagt 120
gatgtcgtgt actggctccg cctttttccc gagggtgggg gagaaccgta tataagtgca 180
gtagtcgccg tgaacgttct ttttcgcaac gggtttgccg ccagaacaca ggtgtcgtga 240
cgcgggatcc gccaccatgg gctccatgtt tcggagcgag gaggtggccc tggtccagct 300
ctttctgccc acagcggctg cctacacctg cgtgagtcgg ctgggcgagc tgggcctcgt 360
ggagttcaga gacctcaacg cctcggtgag cgccttccag agacgctttg tggttgatgt 420
tcggcgctgt gaggagctgg agaagacctt caccttcctg caggaggagg tgcggcgggc 480
tgggctggtc ctgccccccgc caaaggggag gctgccggca cccccacccc gggacctgct 540
gcgcatccag gaggagacgg agcgcctggc ccaggagctg cgggatgtgc ggggcaacca 600
gcaggccctg cgggcccagc tgcaccagct gcagctccac gccgccgtgc tacgccaggg 660
ccatgaacct cagctggcag ccgcccacac agatggggcc tcagagagga cgcccctgct 720
ccaggccccc ggggggccgc accaggacct gagggtcaac tttgtggcag gtgccgtgga 780
gccccacaag gcccctgccc tagagcgcct gctctggagg gcctgcagag gcttcctcat 840
tgccagcttc agggagctgg agcagccgct ggagcacccc gtgacgggcg agccagccac 900
gtggatgacc ttcctcatct cctactgggg tgagcagatc ggacagaaga tccgcaagat 960
cacggactgc ttccactgcc acgtcttccc gtttctgcag caggaggagg cccgcctcgg 1020
ggccctgcag cagctgcaac agcagagcca ggagctgcag gaggtcctcg gggagacaga 1080
gcggttcctg agccaggtgc taggccgggt gctgcagctg ctgccgccag ggcaggtgca 1140
ggtccacaag atgaaggccg tgtacctggc cctgaaccag tgcagcgtga gcaccacgca 1200
caagtgcctc attgccgagg cctggtgctc tgtgcgagac ctgcccgccc tgcaggaggc 1260
cctgcgggac agctcgatgg aggagggagt gagtgccgtg gctcaccgca tcccctgccg 1320
ggacatgccc cccacactca tccgcaccaa ccgcttcacg gccagcttcc agggcatcgt 1380
ggatgcctac ggcgtgggcc gctaccagga ggtcaacccc gctccctaca ccatcatcac 1440
cttccccttc ctgtttgctg tgatgttcgg ggatgtgggc cacgggctgc tcatgttcct 1500
cttcgccctg gccatggtcc ttgcggagaa ccgaccggct gtgaaggccg cgcagaacga 1560
gatctggcag actttcttca ggggccgcta cctgctcctg cttatgggcc tgttctccat 1620

-continued

```
ctacaccggc ttcatctaca acgagtgctt cagtcgcgcc accagcatct tcccctcggg   1680

ctggagtgtg gccgccatgg ccaaccagtc tggctggagt gatgcattcc tggcccagca   1740

cacgatgctt accctggacc ccaacgtcac cggtgtcttc ctgggaccct accccttttgg  1800

catcgatcct atttggagcc tggctgccaa ccacttgagc ttcctcaact ccttcaagat   1860

gaagatgtcc gtcatcctgg gcgtcgtgca catggccttt ggggtggtcc tcggagtctt   1920

caaccacgtg cactttggcc agaggcaccg gctgctgctg gagacgctgc cggagctcac   1980

cttcctgctg ggactcttcg gttacctcgt gttcctagtc atctacaagt ggctgtgtgt   2040

ctgggctgcc agggccgcct cggcccccag catcctcatc cacttcatca acatgttcct   2100

cttctcccac agccccagca acaggctgct ctacccccgg caggaggtgg tccaggccac   2160

gctggtggtc ctggccttgg ccatggtgcc catcctgctg cttggcacac ccctgcacct   2220

gctgcaccgc caccgccgcc gcctgcggag gaggcccgct gaccgacagg aggaaaacaa   2280

ggccgggttg ctggacctgc ctgacgcatc tgtgaatggc tggagctccg atgaggaaaa   2340

ggcagggggc ctggatgatg aagaggaggc cgagctcgtc ccctccgagg tgctcatgca   2400

ccaggccatc cacaccatcg agttctgcct gggctgcgtc tccaacaccg cctcctacct   2460

gcgcctgtgg gccctgagcc tggcccacgc ccagctgtcc gaggttctgt gggccatggt   2520

gatgcgcata ggcctgggcc tgggccggga ggtgggcgtg gcggctgtgg tgctggtccc   2580

catctttgcc gcctttgccg tgatgaccgt ggctatcctg ctggtgatgg agggactctc   2640

agccttcctg cacgccctgc ggctgcactg ggtggaattc cagaacaagt tctactcagg   2700

cacgggctac aagctgagtc ccttcacctt cgctgccaca gatgactagt aagtcgacgg   2760

atcccccggg ctgcaggaat tcgagcatct taccgccatt tatacccata tttgttctgt   2820

ttttcttgat ttgggtatac atttaaatgt taataaaaca aaatggtggg gcaatcattt   2880

acatttttag ggatatgtaa ttactagttc aggtgtattg ccacaagaca aacatgttaa   2940

gaaactttcc cgttatttac gctctgttcc tgttaatcaa cctctggatt acaaaatttg   3000

tgaaagattg actgatattc ttaactatgt tgctcctttt acgctgtgtg gatatgctgc   3060

tttaatgcct ctgtatcatg ctattgcttc ccgtacggct ttcgttttct cctccttgta   3120

taaatcctgg ttgctgtctc tttatgagga gttgtggccc gttgtccgtc aacgtggcgt   3180

ggtgtgctct gtgtttgctg acgcaacccc cactggctgg ggcattgcca ccacctgtca   3240

actcctttct gggactttcg ctttccccct cccgatcgcc acggcagaac tcatcgccgc   3300

ctgccttgcc cgctgctgga caggggctag gttgctgggc actgataatt ccgtggtgtt   3360

gtcggggaag ctgacgtcct ttcg                                          3384
```

```
<210> SEQ ID NO 11
<211> LENGTH: 830
<212> TYPE: PRT
<213> ORGANISM: Homo sapiens

<400> SEQUENCE: 11

Met Gly Ser Met Phe Arg Ser Glu Glu Val Ala Leu Val Gln Leu Phe
1               5                   10                  15

Leu Pro Thr Ala Ala Ala Tyr Thr Cys Val Ser Arg Leu Gly Glu Leu
            20                  25                  30

Gly Leu Val Glu Phe Arg Asp Leu Asn Ala Ser Val Ser Ala Phe Gln
        35                  40                  45

Arg Arg Phe Val Val Asp Val Arg Arg Cys Glu Glu Leu Glu Lys Thr
```

```
    50                  55                  60

Phe Thr Phe Leu Gln Glu Glu Val Arg Arg Ala Gly Leu Val Leu Pro
65                  70                  75                  80

Pro Pro Lys Gly Arg Leu Pro Ala Pro Pro Pro Arg Asp Leu Leu Arg
                85                  90                  95

Ile Gln Glu Glu Thr Glu Arg Leu Ala Gln Glu Leu Arg Asp Val Arg
            100                 105                 110

Gly Asn Gln Gln Ala Leu Arg Ala Gln Leu His Gln Leu Gln Leu His
        115                 120                 125

Ala Ala Val Leu Arg Gln Gly His Glu Pro Gln Leu Ala Ala Ala His
    130                 135                 140

Thr Asp Gly Ala Ser Glu Arg Thr Pro Leu Leu Gln Ala Pro Gly Gly
145                 150                 155                 160

Pro His Gln Asp Leu Arg Val Asn Phe Val Ala Gly Ala Val Glu Pro
                165                 170                 175

His Lys Ala Pro Ala Leu Glu Arg Leu Leu Trp Arg Ala Cys Arg Gly
            180                 185                 190

Phe Leu Ile Ala Ser Phe Arg Glu Leu Glu Gln Pro Leu Glu His Pro
        195                 200                 205

Val Thr Gly Glu Pro Ala Thr Trp Met Thr Phe Leu Ile Ser Tyr Trp
    210                 215                 220

Gly Glu Gln Ile Gly Gln Lys Ile Arg Lys Ile Thr Asp Cys Phe His
225                 230                 235                 240

Cys His Val Phe Pro Phe Leu Gln Gln Glu Glu Ala Arg Leu Gly Ala
                245                 250                 255

Leu Gln Gln Leu Gln Gln Gln Ser Gln Glu Leu Gln Glu Val Leu Gly
            260                 265                 270

Glu Thr Glu Arg Phe Leu Ser Gln Val Leu Gly Arg Val Leu Gln Leu
        275                 280                 285

Leu Pro Pro Gly Gln Val Gln Val His Lys Met Lys Ala Val Tyr Leu
    290                 295                 300

Ala Leu Asn Gln Cys Ser Val Ser Thr Thr His Lys Cys Leu Ile Ala
305                 310                 315                 320

Glu Ala Trp Cys Ser Val Arg Asp Leu Pro Ala Leu Gln Glu Ala Leu
                325                 330                 335

Arg Asp Ser Ser Met Glu Glu Gly Val Ser Ala Val Ala His Arg Ile
            340                 345                 350

Pro Cys Arg Asp Met Pro Pro Thr Leu Ile Arg Thr Asn Arg Phe Thr
        355                 360                 365

Ala Ser Phe Gln Gly Ile Val Asp Ala Tyr Gly Val Gly Arg Tyr Gln
    370                 375                 380

Glu Val Asn Pro Ala Pro Tyr Thr Ile Ile Thr Phe Pro Phe Leu Phe
385                 390                 395                 400

Ala Val Met Phe Gly Asp Val Gly His Gly Leu Leu Met Phe Leu Phe
                405                 410                 415

Ala Leu Ala Met Val Leu Ala Glu Asn Arg Pro Ala Val Lys Ala Ala
            420                 425                 430

Gln Asn Glu Ile Trp Gln Thr Phe Phe Arg Gly Arg Tyr Leu Leu Leu
        435                 440                 445

Leu Met Gly Leu Phe Ser Ile Tyr Thr Gly Phe Ile Tyr Asn Glu Cys
    450                 455                 460

Phe Ser Arg Ala Thr Ser Ile Phe Pro Ser Gly Trp Ser Val Ala Ala
465                 470                 475                 480
```

-continued

| | | | | | | | | | | | | | | | |
|---|---|---|---|---|---|---|---|---|---|---|---|---|---|---|---|
| Met | Ala | Asn | Gln | Ser | Gly | Trp | Ser | Asp | Ala | Phe | Leu | Ala | Gln | His | Thr |
| | | | | 485 | | | | | 490 | | | | | 495 | |
| Met | Leu | Thr | Leu | Asp | Pro | Asn | Val | Thr | Gly | Val | Phe | Leu | Gly | Pro | Tyr |
| | | | 500 | | | | | 505 | | | | | 510 | | |
| Pro | Phe | Gly | Ile | Asp | Pro | Ile | Trp | Ser | Leu | Ala | Ala | Asn | His | Leu | Ser |
| | | 515 | | | | | 520 | | | | | 525 | | | |
| Phe | Leu | Asn | Ser | Phe | Lys | Met | Lys | Met | Ser | Val | Ile | Leu | Gly | Val | Val |
| | 530 | | | | | 535 | | | | | 540 | | | | |
| His | Met | Ala | Phe | Gly | Val | Val | Leu | Gly | Val | Phe | Asn | His | Val | His | Phe |
| 545 | | | | | 550 | | | | | 555 | | | | | 560 |
| Gly | Gln | Arg | His | Arg | Leu | Leu | Leu | Glu | Thr | Leu | Pro | Glu | Leu | Thr | Phe |
| | | | | 565 | | | | | 570 | | | | | 575 | |
| Leu | Leu | Gly | Leu | Phe | Gly | Tyr | Leu | Val | Phe | Leu | Val | Ile | Tyr | Lys | Trp |
| | | | 580 | | | | | 585 | | | | | 590 | | |
| Leu | Cys | Val | Trp | Ala | Ala | Arg | Ala | Ala | Ser | Ala | Pro | Ser | Ile | Leu | Ile |
| | | 595 | | | | | 600 | | | | | 605 | | | |
| His | Phe | Ile | Asn | Met | Phe | Leu | Phe | Ser | His | Ser | Pro | Ser | Asn | Arg | Leu |
| | 610 | | | | | 615 | | | | | 620 | | | | |
| Leu | Tyr | Pro | Arg | Gln | Glu | Val | Val | Gln | Ala | Thr | Leu | Val | Val | Leu | Ala |
| 625 | | | | | 630 | | | | | 635 | | | | | 640 |
| Leu | Ala | Met | Val | Pro | Ile | Leu | Leu | Leu | Gly | Thr | Pro | Leu | His | Leu | Leu |
| | | | | 645 | | | | | 650 | | | | | 655 | |
| His | Arg | His | Arg | Arg | Arg | Leu | Arg | Arg | Arg | Pro | Ala | Asp | Arg | Gln | Glu |
| | | | 660 | | | | | 665 | | | | | 670 | | |
| Glu | Asn | Lys | Ala | Gly | Leu | Leu | Asp | Leu | Pro | Asp | Ala | Ser | Val | Asn | Gly |
| | | 675 | | | | | 680 | | | | | 685 | | | |
| Trp | Ser | Ser | Asp | Glu | Glu | Lys | Ala | Gly | Gly | Leu | Asp | Asp | Glu | Glu | Glu |
| | 690 | | | | | 695 | | | | | 700 | | | | |
| Ala | Glu | Leu | Val | Pro | Ser | Glu | Val | Leu | Met | His | Gln | Ala | Ile | His | Thr |
| 705 | | | | | 710 | | | | | 715 | | | | | 720 |
| Ile | Glu | Phe | Cys | Leu | Gly | Cys | Val | Ser | Asn | Thr | Ala | Ser | Tyr | Leu | Arg |
| | | | | 725 | | | | | 730 | | | | | 735 | |
| Leu | Trp | Ala | Leu | Ser | Leu | Ala | His | Ala | Gln | Leu | Ser | Glu | Val | Leu | Trp |
| | | | 740 | | | | | 745 | | | | | 750 | | |
| Ala | Met | Val | Met | Arg | Ile | Gly | Leu | Gly | Leu | Gly | Arg | Glu | Val | Gly | Val |
| | | 755 | | | | | 760 | | | | | 765 | | | |
| Ala | Ala | Val | Val | Leu | Val | Pro | Ile | Phe | Ala | Ala | Phe | Ala | Val | Met | Thr |
| | 770 | | | | | 775 | | | | | 780 | | | | |
| Val | Ala | Ile | Leu | Leu | Val | Met | Glu | Gly | Leu | Ser | Ala | Phe | Leu | His | Ala |
| 785 | | | | | 790 | | | | | 795 | | | | | 800 |
| Leu | Arg | Leu | His | Trp | Val | Glu | Phe | Gln | Asn | Lys | Phe | Tyr | Ser | Gly | Thr |
| | | | | 805 | | | | | 810 | | | | | 815 | |
| Gly | Tyr | Lys | Leu | Ser | Pro | Phe | Thr | Phe | Ala | Ala | Thr | Asp | Asp | | |
| | | | 820 | | | | | 825 | | | | | 830 | | |

METHODS FOR GENE MODIFICATION OF HEMATOPOIETIC CELLS

RELATED APPLICATIONS

This application is a National Stage application under 35 U.S.C. § 371 of International Application No. PCT/US2019/044237, filed Jul. 30, 2019, which claims benefit of priority to U.S. Provisional Patent Application No. 62/712,146, filed Jul. 30, 2018, the contents of which are incorporated herein in their entirety.

SEQUENCE LISTING

This application is being filed electronically via EFS-Web and includes an electronically submitted sequence listing in .txt format. The .txt file contains a sequence listing entitled “ROPA_01001WO_SeqList_ST25.txt” created on Jul. 30, 2019 and having a size of 57 kilobytes. The sequence listing contained in this .txt file is part of the specification and is incorporated herein by reference in its entirety.

FIELD OF THE INVENTION

The present invention relates generally to methods for genetic modification of hematopoietic cells. In particular, the invention relates to use of combinations of two or more transduction enhancers selected from Prostaglandin E2 (PGE2), recombinant fibronectin fragment, poloxamer, and protamine sulfate to enhance transduction by a recombinant retroviral vector.

BACKGROUND OF THE INVENTION

Ex vivo mediated gene transfer into target cells is a clinically applied method for cell and gene therapy. Recombinant retroviral vectors (e.g., recombinant lentiviral vectors) can be used to deliver polynucleotides to cells (e.g., hematopoietic cells). Contacting target hematopoietic cells with the recombinant retroviral (e.g., lentiviral) vector results in delivery of gene(s) to the hematopoietic cells, a process known as transduction. Subsequently, the hematopoietic cells may be administered to a subject with the intention that the hematopoietic cells engraft themselves into the bone marrow of the subject.

The efficiency of retroviral (e.g., lentiviral) vector transduction is often limited, and transduction efficiency is often a primary impediment to successful gene therapy. Accordingly, there remains an unmet need for compositions and methods suitable for application to hematopoietic cells in a clinical context. The present disclosure provides such compositions and methods, and more.

SUMMARY OF THE INVENTION

The present invention relates generally to methods for genetic modification of hematopoietic cells. In particular, the invention relates to use of a combination of two or more transduction enhancers, wherein at least two of the transduction enhancers of the combination are selected from Prostaglandin E2 (PGE2), poloxamer, recombinant fibronectin fragment, and/or protamine sulfate, to enhance transduction by a recombinant retroviral vector. In certain embodiments, the combination comprises three or more transductions, including Prostaglandin E2 (PGE2), poloxamer, and protamine sulfate. In certain embodiments, the combination comprises four or more transductions, including Prostaglandin E2 (PGE2), poloxamer, recombinant fibronectin fragment, and protamine sulfate. The compositions and methods of the present disclosure are particularly suitable for gene therapy applications, including the treatment of monogenic genetic diseases and disorders. Advantageous, the methods of the disclosure result in reduced toxicity (greater survival) of the transduced cell population compared to transduction without the transductions enhancers.

In one aspect, the disclosure provides a method of genetic modification of hematopoietic cells, comprising: contacting hematopoietic cells with a poloxamer; contacting the hematopoietic cells with Prostaglandin E2 (PGE2) or a derivative thereof; and contacting the hematopoietic cells with a recombinant retroviral vector.

In one aspect, the disclosure provides a method of genetic modification of hematopoietic cells, comprising: providing hematopoietic cells; contacting the hematopoietic cells with a poloxamer; contacting the hematopoietic cells with Prostaglandin E2 (PGE2) or a derivative thereof; and contacting the hematopoietic cells with a recombinant retroviral vector.

In an embodiment, the recombinant retroviral vector is a recombinant lentiviral vector.

In an embodiment, the hematopoietic cells have been manipulated.

In an embodiment, the providing step comprises enrichment for CD34+ cells.

In an embodiment, the hematopoietic cells have been cultured on recombinant fibronectin fragment-coated vessels.

In an embodiment, the poloxamer is selected from the group consisting of poloxamer 288, poloxamer 335, poloxamer 338, and poloxamer 407.

In an embodiment, the poloxamer is poloxamer 338 (LentiBOOST).

In an embodiment, the PGE2 or derivative thereof is modified.

In an embodiment, the PGE2 or derivative thereof is 16,16-dimethyl PGE2 (dmPGE2).

In an embodiment, the PGE2 or derivative thereof is unmodified.

In an embodiment, the method further comprises contacting the hematopoietic cells with protamine sulfate and/or a recombinant fibronectin fragment. In certain embodiments, the recombinant fibronectin fragment may be present in liquid culture or coated on a culture dish. In certain embodiments, the cells may be pre-treated by culture on a dish comprising the recombinant fibronectin and/or the recombinant fibronectin fragment may be present in a liquid culture media during transduction.

In an embodiment, contacting steps are performed simultaneously or during an overlapping period of time.

In an embodiment, the concentration of the PGE2 or derivative thereof is 5-30 μg/mL.

In an embodiment, the concentration of the PGE2 or derivative thereof is about 10 μg/mL.

In an embodiment, the concentration of the poloxamer is 200-1200 μg/mL.

In an embodiment, the concentration of the poloxamer is about 1000 μg/mL.

In an embodiment, the concentration of the protamine sulfate is 4-10 μg/mL.

In an embodiment, the concentration of the protamine sulfate is about 4 μg/mL.

In an embodiment, the concentration of the recombinant fibronectin fragment, e.g., RetroNectin, is about 5 to about 50 μg/mL when used in liquid culture.

In an embodiment, the concentration of the recombinant fibronectin fragment, e.g., RetroNectin, is about 20 μg/mL when used in liquid culture.

In a second aspect, the disclosure provides method of enhancing recombinant retroviral vector-mediated genetic modification of hematopoietic cells, comprising treating or contacting the hematopoietic cells ex vivo with an effective amount of PGE2 or a derivative thereof and with an effective amount of a poloxamer; and exposing or contacting the hematopoietic cells to a recombinant retroviral vector comprising a polynucleotide comprising a gene of interest, wherein viral transduction efficacy of the recombinant retroviral vector is enhanced compared to transduction of hematopoietic cells with the recombinant retroviral vector in the absence of PGE2 and poloxamer.

In an embodiment, the method further comprises treating or contacting the hematopoietic cells ex vivo with an effective amount of protamine sulfate and/or recombinant fibronectin fragment.

In an embodiment, the gene of interest complements a defect in a gene associated with a monogenic genetic disease or disorder.

In an embodiment, the gene of interest is selected form the group consisting of RPK, ITGB2, FANCA, FANCC, FANCG, TCIRG1, CLCN7, TNFSF11, PLEKHM1, TNFRSF11A and OSTM1. In particular embodiments, the gene of interest encodes a protein encoded by any of these genes, or encodes a functional fragment or variant of any of these genes. In particular embodiments, the gene or protein is a human gene or protein.

In an embodiment, the method counteracts the clinical sequelae or ameliorates a monogenic genetic disease or disorder.

In an embodiment, the monogenetic disease or disorder is selected from the group consisting of Fanconi Anemia (including any of the complementation groups), Leukocyte Adhesion Deficiency Type I, Pyruvate Kinase Deficiency, and Infantile Malignant Osteoporosis.

In an embodiment, the hematopoietic cells are CD34-enriched cells, optionally hematopoietic cells, bone-marrow (BM)-derived cells, cord blood (CB)-derived cells, or mobilized peripheral blood (mPB) cells. In certain embodiments, the hematopoietic cells were obtained from a subject to be treated with the recombinantly modified hematopoietic cells.

In a third aspect, the disclosure provides a method for recombinant retroviral vector-mediated genetic modification of hematopoietic cells, comprising preparing CD34-enriched cells from a biological sample (optionally, peripheral blood) obtained from a subject treated with G-CSF or an analog thereof (optionally, filgrastim, sargramostim, or pegfilgrastim) and/or plerixafor; and genetically modifying the CD34-enriched cells with a recombinant retroviral vector comprising a polynucleotide encoding a Fanconi anemia complementation group (FANC) gene, ITGB2, an R-type pyruvate kinase, OSTM1, TCIRG1, CLCN7, OSTM1, or a gene encoding functional variant or fragment thereof and an eukaryotically active promoter sequence operatively linked thereto; wherein the genetically modifying step comprises contacting the CD34-enriched cells with the recombinant retroviral vector, PGE2 and poloxamer, and optionally, protamine sulfate and/or recombinant fibronectin fragment.

The disclosure provides an in vitro method for recombinant retroviral vector-mediated genetic modification of hematopoietic cells, comprising preparing CD34-enriched cells from a biological sample (optionally, peripheral blood) obtained from a subject treated with G-CSF or an analog thereof (optionally, filgrastim, sargramostim, or pegfilgrastim) and/or plerixafor; and genetically modifying the CD34-enriched cells with a recombinant retroviral vector for a disease or disorder selected from Fanconi Anemia, Leukocyte Adhesion Deficiency Type I, Pyruvate Kinase Deficiency, or Infantile Malignant Osteoporosis; wherein the recombinant retroviral vector comprises a polynucleotide encoding a Fanconi anemia complementation group (FANC) gene, ITGB2, an R-type pyruvate kinase, CLCN7, OSTM1, TCIRG1, TNFSF11, PLEKHM1, TNFRSF11A or a gene encoding functional variant or fragment thereof and an eukaryotically active promoter sequence operatively linked thereto; wherein the genetically modifying step comprises contacting the CD34-enriched cells with PGE2 and poloxamer, and optionally, protamine sulfate.

The disclosure provides a method of treating a monogenic genetic disease or disorder in a subject in need thereof, comprising providing to the subject genetically modified hematopoietic cells that express a polypeptide lacking or mutated due to the monogenic genetic disease or disorder. In particular embodiments, CD34-enriched cells obtained from a biological sample (optionally, peripheral blood) obtained from a subject after the subject are treated with G-CSF or an analog thereof (optionally, filgrastim, sargramostim, or pegfilgrastim) and/or plerixafor are genetically modified by contacting them with a recombinant retroviral vector comprising an expression cassette comprising a polynucleotide sequence encoding the polypeptide in the presence at least two transduction enhancers selected from Prostaglandin E2 (PGE2), poloxamer, recombinant fibronectin fragment, and/or protamine sulfate, and the resulting genetically modified cells are provided to the subject. In certain embodiments, disease or disorder is selected from Fanconi Anemia, Leukocyte Adhesion Deficiency Type I, Pyruvate Kinase Deficiency, or Infantile Malignant Osteoporosis; and the recombinant retroviral vector comprises a polynucleotide comprising a Fanconi anemia complementation group (FANC) gene, ITGB2, an R-type pyruvate kinase, CLCN7, OSTM1, TCIRG1, TNFSF11, PLEKHM1, TNFRSF11A or a gene encoding functional variant or fragment thereof, and an eukaryotically active promoter sequence operatively linked thereto.

In certain embodiments, the disclosure provides a method treating Fanconi Anemia in a subject in need thereof, comprising administering hematopoietic cells produced by genetically modifying the hematopoietic cells with a recombinant retroviral vector comprising a polynucleotide encoding a Fanconi anemia complementation group (FANC) gene or a gene encoding functional variant or fragment thereof according to the methods disclosed herein.

In certain embodiments, the disclosure provides a method treating Leukocyte Adhesion Deficiency Type I in a subject in need thereof, comprising administering hematopoietic cells produced by genetically modifying the hematopoietic cells with a recombinant retroviral vector comprising a polynucleotide encoding a ITGB2 gene or a gene encoding functional variant or fragment thereof according to the methods disclosed herein.

In certain embodiments, the disclosure provides a method treating Pyruvate Kinase Deficiency in a subject in need thereof, comprising administering hematopoietic cells produced by genetically modifying the hematopoietic cells with a recombinant retroviral vector comprising a polynucleotide encoding a R-type pyruvate kinase gene or a gene encoding functional variant or fragment thereof according to the methods disclosed herein.

In certain embodiments, the disclosure provides a method treating Infantile Malignant Osteoporosis in a subject in need thereof, comprising administering hematopoietic cells produced by genetically modifying the hematopoietic cells with a recombinant retroviral vector comprising a polynucleotide encoding a CLCN7, OSTM1, TCIRG1, TNFSF11, PLEKHM1, or TNFRSF11A gene or a gene encoding functional variant or fragment thereof according to the methods disclosed herein.

In a further related aspect, the disclosure provides a method of producing a population of hematopoietic cells comprising at least 80% or at least 90% genetically modified hematopoietic cells, comprising: contacting hematopoietic cells ex vivo with recombinant retroviral vector (optionally, a lentiviral vector) comprising a polynucleotide that comprises a gene of interest or encodes a polypeptide of interest, wherein the contacting occurs in the presence of a PGE2 or a derivative thereof, optionally human PGE2 or 16,16-dimethyl PGE2 (dmPGE2), and a poloxamer, optionally poloxamer 338 (LentiBOOST™). The cells may be contacted with the retroviral vector under conditions and for a time sufficient to permit transduction of the cells by the retroviral vector, e.g., in suitable culture media for at least one hour, at least two hours, at least four hours, at least eight hours, at least twelve hours, at least 16 hours, or at least 24 hours. In some embodiments, the cells are transduced either once or two consecutive times, e.g., following pre-stimulation, with each transduction cycle being between 12 and 24 hours, or between 16-18 hours. In some embodiments, the cells are contacted with the retroviral vector and the transduction enhancers during the same or an overlapping period of time. Following transduction, the cells may be formulated in a freezing mix (e.g., CryoStor CS5, BioLife Solutions, Bothell, WA, USA) and cryopreserved for later use. In certain embodiments of this and other aspects, the poloxamer is selected from the group consisting of poloxamer 288, poloxamer 335, poloxamer 338, and poloxamer 407. In particular embodiments, the poloxamer is poloxamer 338 (LentiBOOST™). Certain embodiments, the PGE2 or derivative thereof is unmodified or modified, e.g., 16,16-dimethyl PGE2 (dmPGE2). In particular embodiments, the method further comprises contacting the hematopoietic cells with protamine sulfate and/or a recombinant fibronectin fragment. In some embodiments, the concentration of the PGE2 or derivative thereof is 5-30 μg/mL, or about 10 μg/mL. In some embodiments, the concentration of the poloxamer is 200-1200 μg/mL or about 1000 μg/mL. In some embodiments, the concentration of the protamine sulfate is 4-10 μg/mL or about 4 μg/mL. In certain embodiments, the polynucleotide complements a defect in a gene associated with a monogenic genetic disease or disorder. In certain embodiments, the polypeptide of interest is selected from the group consisting of RPK, ITGB2, FANCA, FANCC, FANCG, TCIRG1, CLCN7, TNFSF11, PLEKHM1, TNFRSF11A and OSTM1. In some embodiments, the disease or disorder is a monogenic genetic disease or disorder, e.g., selected from the group consisting of Fanconi Anemia, Leukocyte Adhesion Deficiency Type I, Pyruvate Kinase Deficiency, and Infantile Malignant Osteopetrosis. In particular embodiments, the hematopoietic cells are CD34-enriched cells or CD34+ hematopoietic cells, optionally bone-marrow (BM)-derived cells, cord blood (CB)-derived cells, or mobilized peripheral blood (mPB) cells. In some embodiments, the population of hematopoietic cells has a VCN/cell of at least 1.0, at least 1.5, at least 2.0, or at least 2.5.

In a related aspect, the disclosure provides a population of hematopoietic cells comprising at least 80% or at least 90% genetically modified hematopoietic cells, wherein the population of cells was produced by a disclosed method.

In another related aspect, the disclosure provides a method of treating a genetic disease or disorder in a subject in need thereof, comprising providing to the subject a population of hematopoietic cells comprising at least 80% or at least 90% genetically modified hematopoietic cells, wherein the population of cells was produced by a disclosed method, wherein the hematopoietic cells were obtained from the subject before being contacted ex vivo with the retroviral vector, and wherein the gene of interest encodes a functional polypeptide that is mutated or lacking in the subject due to the genetic disease or disorder. In some embodiments, the polypeptide is selected from the group consisting of RPK, ITGB2, FANCA, FANCC, FANCG, TCIRG1, CLCN7, TNFSF11, PLEKHM1, TNFRSF11A and OSTM1. In some embodiments, the disease or disorder is a monogenic genetic disease or disorder, e.g., selected from the group consisting of Fanconi Anemia, Leukocyte Adhesion Deficiency Type I, Pyruvate Kinase Deficiency, and Infantile Malignant Osteopetrosis. In particular embodiments, the hematopoietic cells are CD34-enriched cells, optionally bone-marrow (BM)-derived cells, cord blood (CB)-derived cells, or mobilized peripheral blood (mPB) cells.

In various embodiments of any of the aspects and embodiments disclosed herein, cells are transduced on dishes coated with a recombinant fibronectin fragment, e.g., RetroNectin™. In various embodiments of any of the aspects and embodiments disclosed herein, cells are pre-treated by culturing on dishes coated with a recombinant fibronectin fragment, e.g., RetroNectin™ before and/or during transduction. In some embodiments, cells are transduced in liquid media comprising Retro-Nectin. In some embodiments, cells are pre-treated by culturing on dishes coated with a recombinant fibronectin fragment and also transduced in liquid culture in the presence of the recombinant fibronectin fragment and other TEs. Thus is some embodiments, cells are exposed to the recombinant fibronectin before exposure to other TEs during transduction, whereas in some embodiments, cells are exposed to the recombinant fibronectin during the same or an overlapping time period as the other TEs.

In various embodiments of any of the aspects and embodiments disclosed herein, cells are transduced in the presence of prostaglandin E2 (PGE2), poloxamer (e.g., LentiBoost™), recombinant fibronectin fragment (e.g., RetroNectin™), and protamine sulfate.

Other features and advantages of the invention will be apparent from and encompassed by the following detailed description and claims.

BRIEF DESCRIPTION OF THE DRAWINGS

FIGS. 7D and 7E show the effect of LB, PGE2 and PS on the percent of transduction (FIG. 7D) and VCN (FIG. 7E) of CFCs derived from different sources of CD34+, including cord blood (CB-CD34+) and mobilized peripheral blood (mPB-CD34+).

FIG. 9A shows results for CFC assay. FIG. 9B shows results for VCN in CFUs. Results are shown for burst forming unit-erythroid (BFU-E) cells, granulocyte-macrophage progenitors CFU-GM), and myeloid progenitors (CFU-GM). FIG. 9C shows transduction efficiency in CFCs.

DETAILED DESCRIPTION

Figure 1:
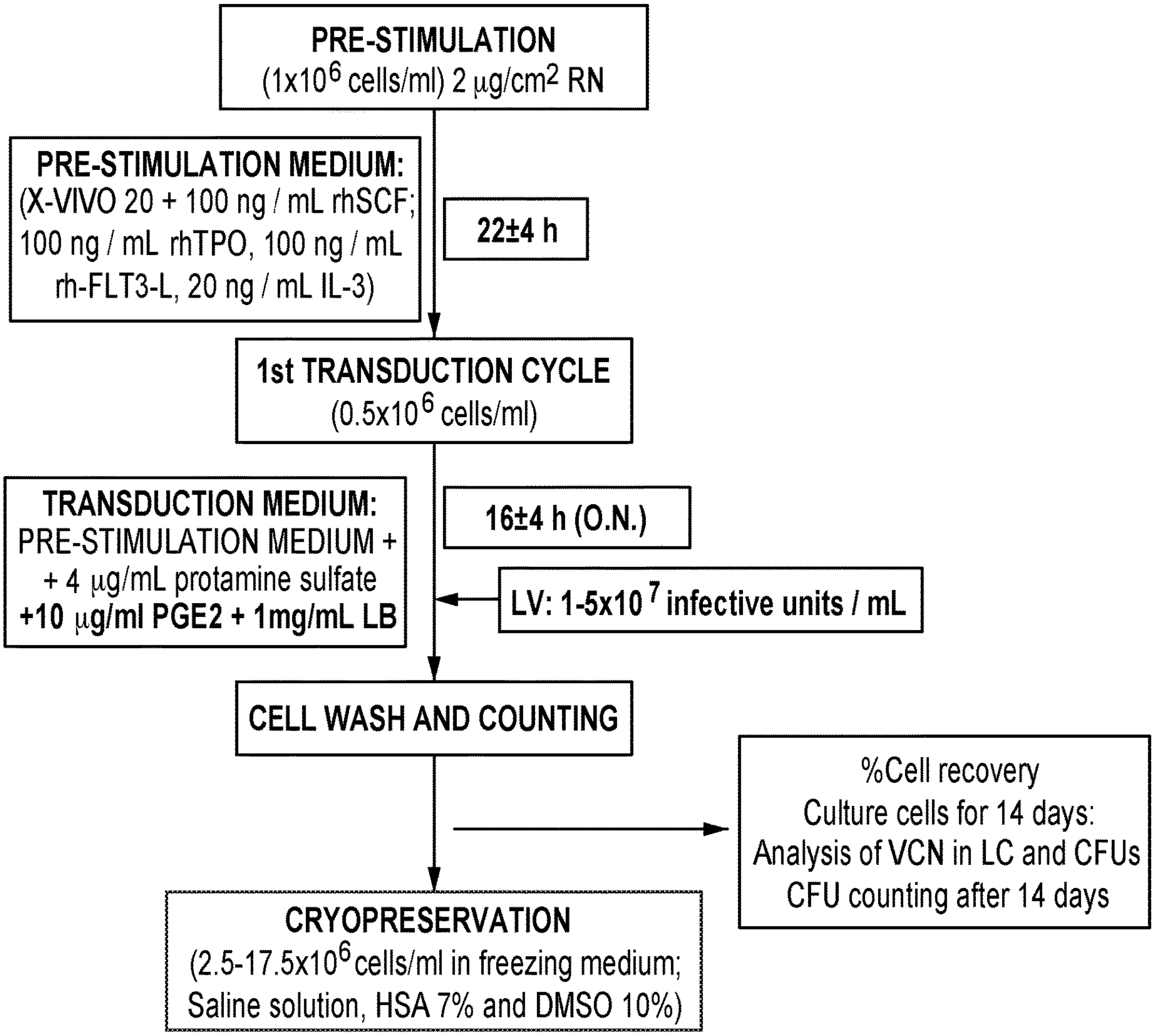
FIG. 1 shows an illustrative transduction protocol. The amounts or combinations of TEs may vary. Cryopreservation is optional. The cells may be used fresh or after frozen storage.

The present disclosure provides compositions and methods for genetic modification of hematopoietic cells. In particular, the invention relates to use of a combination of two or more of Prostaglandin E2 (PGE2), poloxamer, recombinant fibronectin fragment, and/or protamine sulfate to enhance transduction by a recombinant retroviral vector. The compositions and methods of the present disclosure are particularly suitable for gene therapy applications, including the treatment of monogenic diseases and disorders. Factors that have limited gene therapy success, including low transduction efficiency, are solved by the compositions and methods provided herein.

A. Definitions

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Various embodiments contemplated herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*, each of which is expressly incorporated by reference herein.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

"Transfection" refer to the process of introducing naked DNA into cells by non-viral methods.

"Infection" refers to the process of introducing foreign DNA into cells using a viral vector.

"Transduction" refers to the introduction of foreign DNA into a cell's genome using a viral vector.

"Vector copy number" or "VCN" refers to the number of copies of vector in a sample divided by the number of cells. Generally the number of copies of vector is determined by quantitative polymerase chain reaction (qPCR) using a probe against the Psi sequence of the integrated provirus, and the number of cells is determined by qPCR using a probe against a human housekeeping gene for which there will be two copies per cell (one per chromosome).

"Transduction efficiency" refers to the percentage of cells transduced with at least one provirus copy. For example if $1\times10^6$ cells are exposed to a virus and $0.5\times10^6$ cells are determined to have a least one copy of a virus in their genome, then the transduction efficiency is 50%. An illustrative method for determining transduction efficiency is flow cytometry.

As used herein, the term "retrovirus" or "retroviral" refers an RNA virus that reverse transcribes its genomic RNA into a linear double-stranded DNA copy and subsequently covalently integrates its genomic DNA into a host genome. Retrovirus vectors are a common tool for gene delivery (Miller, 2000, *Nature*. 357:455-460). Once the virus is integrated into the host genome, it is referred to as a "provirus." The provirus serves as a template for RNA polymerase II and directs the expression of RNA molecules encoded by the virus.

Illustrative retroviruses (family Retroviridae) include, but are not limited to: (1) genus gammaretrovirus, such as, Moloney murine leukemia virus (M-MuLV), Moloney murine sarcoma virus (MoMSV), murine mammary tumor virus (MuMTV), gibbon ape leukemia virus (GaLV), and feline leukemia virus (FLV), (2) genus spumavirus, such as, simian foamy virus, (3) genus lentivirus, such as, human immunodeficiency virus-1 and simian immunodeficiency virus.

As used herein, the term "lentiviral" or "lentivirus" refers to a group (or genus) of complex retroviruses. Illustrative lentiviruses include, but are not limited to: HIV (human immunodeficiency virus; including HIV type 1, and HIV type 2; visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV-based vector backbones (i.e., HIV cis-acting sequence elements) are preferred.

Retroviral vectors, and more particularly, lentiviral vectors, may be used in practicing the present invention. Accordingly, the term "retroviral vector," as used herein is meant to include "lentiviral vector"; and the term "retrovirus" as used herein is meant to include "lentivirus."

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication or reverse transcription in a cell, or may include sequences sufficient to allow integration into host cell DNA. Useful vectors include viral vectors. Useful viral vectors include, e.g., replication defective retroviruses and lentiviruses.

The term "viral vector" may refer either to a vector or vector particle capable of transferring a nucleic acid into a cell or to the transferred nucleic acid itself. Viral vectors contain structural and/or functional genetic elements that are primarily derived from a virus. The term "retroviral vector" refers to a viral vector containing structural and functional genetic elements, or portions thereof, that are primarily derived from a retrovirus. The term "lentiviral vector" refers to a viral vector containing structural and functional genetic elements, or portions thereof, including LTRs that are primarily derived from a lentivirus. The term "hybrid" refers to a vector, LTR or other nucleic acid containing both retroviral, e.g., lentiviral, sequences and non-lentiviral viral sequences. In one embodiment, a hybrid vector refers to a vector or transfer plasmid comprising retroviral, e.g., lentiviral, sequences for reverse transcription, replication, integration and/or packaging.

In particular embodiments, the terms "lentiviral vector" and "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the invention and are present in DNA form in the DNA plasmids of the invention.

According to certain specific embodiments, most or all of the viral vector backbone sequences are derived from a lentivirus, e.g., HIV-1. However, it is to be understood that many different sources of lentiviral sequences can be used, and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid of the present invention.

As used herein, the terms "polynucleotide" or "nucleic acid" generally refers to a biopolymer comprising nucleotide monomers covalently bonded in a chain, such as DNA and RNA. In some embodiments, polynucleotide refers to genomic DNA (gDNA), complementary DNA (cDNA), or DNA. Polynucleotides include single and double stranded polynucleotides, either recombinant, synthetic, or isolated. In some embodiments, polynucleotide refers to messenger RNA (mRNA), RNA, genomic RNA (gRNA), plus strand RNA (RNA(+)), minus strand RNA (RNA(−)). As used here, the terms "polyribonucleotide" or "ribonucleic acid" also refer to messenger RNA (mRNA), RNA, genomic RNA (gRNA), plus strand RNA (RNA(+)), minus strand RNA (RNA(−)). Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. In various illustrative embodiments, viral vector and transfer plasmid polynucleotide sequences and compositions comprising the same are contemplated. In particular embodiments, polynucleotides encoding one or more therapeutic polypeptides and/or other genes of interest are contemplated. In particular embodiments, polynucleotides encoding a therapeutic polypeptide including, but not limited to, RPK, ITGB2, FANCA, FANCC, FANCG, TCIRG1, CLCN7, TNFSF11, PLEKHM1, TNFRSF11A and OSTM1 genes. In some embodiments, the polynucleotides are codon-optimized variants of any of these genes. In some embodiments, the polynucleotides encode a human polypeptide or a functional fragment or variant thereof, such as, for example, a polypeptide encoded by any of the disclosed genes.

As used herein, a "pseudotyped" vector refers to a vector having a recombinant capsid or envelope protein that differs from the capsid or envelope protein of the native vector. For example, a VSVG-pseudotyped lentiviral vector is a vector generated by co-expression in a packaging cell line of the envelope protein of the VSVG virus with the RNA genome of the virus in a manner that permits incorporation of the VSVG envelope protein into viral particles containing the RNA genome. Pseudotyped vectors may have altered tropism and/or decreased immunogenicity, making them desirable for use in gene therapy applications. It is within the skill of those in the art to generate pseudotyped vector as well as to change the pseudotyping of a vector by generating viral particles in a different packing cell line or by co-expressing the envelope protein (or capsid protein) from a plasmid or other DNA encoding a different envelope protein (or capsid protein). Exemplary methods are provided in Cronin et al. *Curr. Gene Ther.* 5:387-398 (2005). In some embodiments, the methods of the disclosure involve the use of pseudotyped recombinant retroviral vectors (e.g. lentiviral vectors). In some embodiments, the pseudotyped recombinant retroviral vectors is VSVG-pseudotyped.

By "enhance" or "promote," or "increase" or "expand" refers generally to the ability of the compositions and/or methods contemplated herein to elicit, cause, or produce higher numbers of transduced cells compared to the number of cells transduced by either vehicle or a control molecule/composition, or to elicit, cause, or produce a higher VCN in a population of transduced cells. In one embodiment, a hematopoietic stem or progenitor cell transduced with compositions and methods contemplated herein comprises an increase in the number of transduced cells compared to existing transduction compositions and methods, or comprises an increase in VCN in a population of transduced cells. Increases in cell transduction, can be ascertained using methods known in the art, such as reporter assays, RT-PCR, and cell surface protein expression, among others. An "increased" or "enhanced" amount of transduction is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the number of cells transduced by vehicle, a control composition, or other transduction method.

By "decrease" or "lower," or "lessen," or "reduce," or "abate" refers generally to compositions or methods that result in comparably fewer transduced cells compared to cells transduced with compositions and/or methods according to the present invention. A "decrease" or "reduced" amount of transduced cells is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the number of transduced cells (reference response) produced by compositions and/or methods according to the present invention.

By "maintain," or "preserve," or "maintenance," or "no change," or "no substantial change," or "no substantial decrease" refers generally to a physiological response that is comparable to a response caused by either vehicle, a control molecule/composition, or the response in a particular cell. A comparable response is one that is not significantly different or measurable different from the reference response.

In the following description, certain specific details are set forth in order to provide a thorough understanding of various illustrative embodiments of the invention contemplated herein. However, one skilled in the art will understand that particular illustrative embodiments may be practiced without these details. In addition, it should be understood that the individual vectors, or groups of vectors, derived from the various combinations of the structures and substituents described herein, are disclosed by the present application to the same extent as if each vector or group of vectors was set forth individually. Thus, selection of particular vector structures or particular substituents is within the scope of the present disclosure.

As used herein, "X-VIVO 20" or "X-VIVO" refers to X-VIVO™ 20 Chemically Defined, Serum-free Hematopoietic Cell Medium, available from Lonza®. Other media than X-VIVO 20 may be used, and those skilled in the art are capable of selecting suitable media for cell growth and transduction.

As used herein, "rhSCF" refers to recombinant human stem-cell factor.

As used herein, "rhTPO" refers to recombinant human thrombopoeitin.

As used herein, "rh-FLT3-L" refers to recombinant human fms-related tyrosine kinase 3-ligand.

As used herein, "IL-3" or "rhIL-3" refers to recombinant human interleukin 3.

As used herein, "PGE2" refers to Prostaglandin E2 (PGE2), also known as dinoprostone.

As used herein, "poloxamer" refers to a nonionic triblock copolymers composed of a central hydrophobic chain of polyoxypropylene (poly(propylene oxide)) flanked by two hydrophilic chains of polyoxyethylene (poly(ethylene oxide)).

As used herein, "recombinant fibronectin fragment" refers to any fragment of the protein fibronectin that promotes enhances transduction efficiency. Without being bound by theory, it is believed that recombinant fibronectin fragment promotes co-localization of lentivirus or retrovirus with target cells. An example of a recombinant fibronectin fragment is the CH296 fragment of human fibronectin, tradename RetroNectin™.

The concentrations of PGE2 or a derivative thereof, poloxamer, or protamine sulfate provided in the disclosure and claims refer to the concentration of each agent in the media in which the cells are cultured.

As used herein, "LB" or "LentiBoost" refers to LentiBOOST™ transduction enhancer available from Sirion Biotech®. Synonyms include poloxamer 338, F108, and Kolliphor® P338.

As used herein, "HSA" refers to human serum albumin.

As used herein, "DMSO" refers to dimethyl sulfoxide.

As used herein, "CFC" refers to colony forming cells. The colony forming cell (CFC) assay is used to study the proliferation and differentiation pattern of hematopoietic progenitors by their ability to form colonies in a semisolid medium. The number and the morphology of the colonies formed by a fixed number of input cells provide preliminary information about the ability of progenitors to differentiate and proliferate. Exemplary assays are provided in Sarma et al. Colony forming cell (CFC) assay for human hematopoietic cells. *J Vis Exp.* 2010 Dec. 18; (46).

As used herein, "LC" refers to "liquid culture."

As used herein, "CFU" refers to colony forming units. CFU is understood to be synonymous with CFC, but is sometimes used in reference to the types of CFUs growing in semisolid media.

As used herein, "TU" refers to transducing units. TU/mL is a common measurement of the functional titer of a retroviral (lentiviral) preparation.

As used herein, "PS" refers to protamine sulfate.

As used herein, "TE" refers to one or more transduction enhancers.

As used herein, "CB fresh cells" refers to fresh cord blood cells.

As used herein, "MOI" refers to multiplicity of infection.

As used herein, "BFU-E" refers to burst forming unit-erythroid (BFU-E) cells, the earliest erythroid progenitor.

As used herein, "CFU-GM" refers to colony forming units of granulocyte-macrophage progenitors.

As used herein, "CFU-GEMM" refers to colony forming units of myeloid stem cells (granulocyte, erythrocyte, monocyte, megakaryocyte).

As used herein, "mPB" refers to mobilized peripheral blood cells.

As used herein, "SCGM" refers to CellGenix® SCGM serum-free media.

The terms "administering" or "introducing" or "providing to", as used herein, refer to delivery of a hematopoietic cell population to a subject, e.g., by infusing the cell population of the subject intraarterially or intravenously. The hematopoietic cell population may be administered in various solutions, such as saline. In some embodiments, the solution used will be isotonic to the blood of the subject and pH-buffered.

Typically, a cell is referred to as "transduced" when a viral vector or vector particle has introduced heterologous DNA (e.g., the vector or expression cassette thereof) into the genome of the cell.

The term "host cell", as used herein refers to a cell which has been transduced with a viral vector or vector particle. It will be appreciated that the term "host cell" refers to the original transduced cell and progeny thereof.

The terms "treatment", "treating" and the like are used herein to generally mean obtaining a desired pharmacologic and/or physiologic effect. The effect may be prophylactic in terms of completely or partially preventing a disease or symptom thereof, e.g., reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

B. Embodiments and Variations

Various compositions and methods are described below. Although particular compositions and methods are exemplified herein, it is understood that any of a number of alternative compositions and methods are applicable and suitable for use in practicing the compositions and methods disclosed herein. It will also be understood that an evaluation of the expression constructs and methods disclosed herein may be carried out using procedures standard in the art.

1. Transduction Using Combinations of Transduction Enhancers

The present disclosure provides advantageous methods for transducing hematopoietic cells with lentiviral vectors to produce a population of hematopoietic cells having a high percentage of cells transduced with the lentiviral vector. These methods are particularly advantageous for transducing hematopoietic cells with lentiviral gene therapy vectors to correct a genetic defect, since they achieve large numbers of cells that express a functional product of the corrected gene introduced by the lentiviral gene therapy vector.

Various transduction enhancers are known in the art, including polybrene, protamine sulfate, retronectin (recombinant fibronectin fragment), and DEAE Dextran. In some cases, polycationic agents, such as polybrene, have been employed as transduction enhancers. Denning et al. *Mol Biotechnol.* 2013 March; 53 (3): 308-314. In addition, rapamycin and cyclosporin A are used as transduction enhancers. However, the present disclosure identifies particular combinations of transduction enhancers that achieve significantly higher levels of lentiviral transduction of hematopoietic cells as compared to use of each of the transduction enhancers alone.

In one aspect, the disclosure provides a method of genetic modification of hematopoietic cells, comprising: contacting the hematopoietic cells with at least two transduction enhancers selected from: Prostaglandin E2 (PGE2) or a derivative thereof, a poloxamer, protamine sulfate, and recombinant fibronectin fragment; and contacting the hematopoietic cells with a recombinant retroviral vector. The cells may be contacted with the retroviral vector under conditions and for a time sufficient to permit transduction of the cells by the retroviral vector, e.g., in suitable culture media for at least one hour, at least two hours, at least four hours, at least eight hours, at least twelve hours, or at least 16 hours. In some embodiments, the cells are transduced either once or two consecutive times, e.g., following pre-stimulation, with each transduction cycle being between 12 and 24 hours, or between 16-18 hours. In some embodiments, the cells are contacted with the retroviral vector and the transduction enhancers during the same or an overlapping period of time. In particular embodiments, the cells are contacted with the transduction enhancers and the recombinant retroviral vector at the same time or during an overlapping time period. In certain embodiments, the two or more transduction enhancers comprise the poloxamer. In an embodiment, the poloxamer is poloxamer 338 (LentiBOOST™). In certain embodiments, the two or more transduction enhancers comprise or consist of the poloxamer and the PGE2 or derivative thereof. In an embodiment, the poloxamer is poloxamer 338 (LentiBOOST™). In certain embodiments, the two or more transduction enhancers comprise or consist of the poloxamer and the protamine sulfate. In an embodiment, the poloxamer is poloxamer 338 (LentiBOOST™). In certain embodiments, the two or more transduction enhancers comprise or consist of the poloxamer, the PGE2, and the protamine sulfate. In an embodiment, the poloxamer is poloxamer 338 (LentiBOOST™). In certain embodiments, the two or more transduction enhancers comprise or consist of prostaglandin E2 (PGE2) or a derivative thereof, a poloxamer, protamine sulfate, and recombinant fibronectin fragment. In various embodiments of any of the aspects and embodiments disclosed herein, cells are transduced on dishes coated with a recombinant fibronectin fragment, e.g., RetroNectin™. In various embodiments, cells are pre-treated by culturing on dishes coated with a recombinant fibronectin fragment, e.g., RetroNectin™ before and/or during transduction. In certain embodiments, the method comprises pre-stimulation by culturing the cells on plates coated with about 2 ug/cm$^2$ RetroNectin™ (RN). In some embodiments, cells are transduced in liquid media comprising Retro-Nectin™. In some embodiments, cells are pre-treated by culturing on dishes coated with a recombinant fibronectin fragment and also transduced in liquid culture in the presence of the recombinant fibronectin fragment and other TEs.

In one aspect, the disclosure provides a method of genetic modification of hematopoietic cells, comprising: providing hematopoietic cells; contacting the hematopoietic cells with at least two transduction enhancers selected from Prostaglandin E2 (PGE2) or a derivative thereof, a poloxamer (e.g., poloxamer 338 (LentiBOOST™), protamine sulfate, and recombinant fibronectin fragment; and contacting the hematopoietic cells with a recombinant retroviral vector. In particular embodiments, the cells are contacted with the transduction enhancers and the recombinant retroviral vector at the same time or during an overlapping time period. In certain embodiments, the two or more transduction enhancers comprise the poloxamer. In an embodiment, the poloxamer is poloxamer 338 (LentiBOOST™). In certain embodiments, the two or more transduction enhancers comprise the poloxamer and the PGE2 or derivative thereof. In an embodiment, the poloxamer is poloxamer 338 (LentiBOOST™). In certain embodiments, the two or more transduction enhancers comprise or consist of the poloxamer and the protamine sulfate. In an embodiment, the poloxamer is poloxamer 338 (LentiBOOST™). In certain embodiments, the two or more transduction enhancers comprise or consist of the poloxamer, the PGE2, and the protamine sulfate. In an embodiment, the poloxamer is poloxamer 338 (LentiBOOST™). In certain embodiments, the two or more transduction enhancers comprise or consist of prostaglandin E2 (PGE2) or a derivative thereof, a poloxamer, protamine sulfate, and recombinant fibronectin fragment. In an embodiment, the poloxamer is poloxamer 338 (LentiBOOST™). In certain embodiments, the two or more transduction enhancers comprise or consist of prostaglandin E2 (PGE2) or a derivative thereof, a poloxamer, protamine sulfate, and recombinant fibronectin fragment. In various embodiments of any of the aspects and embodiments disclosed herein, cells are transduced on dishes coated with a recombinant fibronectin fragment, e.g., RetroNectin™. In various embodiments, cells are pre-treated by culturing on dishes coated with a recombinant fibronectin fragment, e.g., RetroNectin™ before and/or during transduction. In certain embodiments, the method comprises pre-stimulation by culturing the cells on plates coated with about 2 ug/cm$^2$ RetroNectin™ (RN). In some embodiments, cells are transduced in liquid media comprising Retro-Nectin™. In some embodiments, cells are pre-treated by culturing on dishes coated with a recombinant fibronectin fragment and also transduced in liquid culture in the presence of the recombinant fibronectin fragment and other TEs.

In various embodiments of methods disclosed herein, a population of cells is cultured in the presence of a retrovirus vector, one or more agents that stimulate the prostaglandin EP receptor signaling pathway and a poloxamer having an average molecular weight of about 10,000 Daltons. In particular embodiments, the cells are contacted with the transduction enhancers and the recombinant retroviral vector at the same time or during an overlapping time period.

In various embodiments of methods disclosed herein, a population of cells is cultured in the presence of a retrovirus vector, one or more agents that stimulate the prostaglandin EP receptor signaling pathway and a poloxamer that has an average molecular weight of polypropylene subunits greater than about 2250 Daltons and comprises greater than about 40% polyethylene oxide. In particular embodiments, the cells are contacted with the transduction enhancers and the recombinant retroviral vector at the same time or during an overlapping time period.

In particular embodiments of methods disclosed herein, the cells are transduced in media comprising a combination of the three transduction enhancers: poloxamer 338 (LentiBOOST), PGE2, and protamine sulfate, e.g., in a liquid media. The cells may be adhered to a culture dish, or the cells may be not adhered to a culture dish. In particular embodiments, the cells are contacted with the transduction enhancers and the recombinant retroviral vector at the same time or during an overlapping time period. In certain embodiments, the method comprises pre-stimulation by culturing the cells on plates coated with a recombinant fibronectin fragment, e.g., RetroNectin™ (RN). In certain embodiments, cells are transduced on dishes coated with a recombinant fibronectin fragment, e.g., RetroNectin™. In various embodiments, cells are pre-treated by culturing on dishes coated with a recombinant fibronectin fragment, e.g., RetroNectin™ before and/or during transduction. In certain embodiments, the method comprises pre-stimulation by culturing the cells on plates coated with about 2 ug/cm$^2$ RetroNectin™ (RN). In some embodiments, cells are transduced in liquid media comprising Retro-Nectin™. In some embodiments, cells are pre-treated by culturing on dishes coated with a recombinant fibronectin fragment and also transduced in liquid culture in the presence of the recombinant fibronectin fragment and other TEs.

In a related aspect, the disclosure provides a method of enhancing recombinant retroviral vector-mediated genetic modification of hematopoietic cells, comprising treating or contacting the hematopoietic cells ex vivo with an effective amount of a combination of two or more transduction enhancers, wherein at least two of the transduction enhancers are selected from PGE2 or a derivative thereof, a poloxamer, protamine sulfate, and a recombinant fibronectin fragment. In an embodiment, the poloxamer is poloxamer 338 (LentiBOOST™). In some embodiments, the cells are contacted with PGE2 or a derivative thereof and an effective amount of a poloxamer; and contacted with a recombinant retroviral vector comprising a polynucleotide comprising a gene of interest, wherein viral transduction efficacy of the retroviral vector is enhanced compared to transduction of hematopoietic cells with the recombinant retroviral vector in the absence of the combination of transduction enhancers, e.g., PGE2 and poloxamer. In certain embodiments, the two or more transduction enhancers comprise the poloxamer and the PGE2 or derivative thereof. In an embodiment, the poloxamer is poloxamer 338 (LentiBOOST™). In certain embodiments, the two or more transduction enhancers comprise or consist of the poloxamer and the protamine sulfate. In an embodiment, the method further comprises treating or contacting the hematopoietic cells ex vivo with an effective amount of protamine sulfate. In certain embodiments, the two or more transduction enhancers comprise or consist of prostaglandin E2 (PGE2) or a derivative thereof, a poloxamer, protamine sulfate, and recombinant fibronectin fragment. In various embodiments of any of the aspects and embodiments disclosed herein, cells are transduced on dishes coated with a recombinant fibronectin fragment, e.g., RetroNectin™. In various embodiments, cells are pre-treated by culturing on dishes coated with a recombinant fibronectin fragment, e.g., RetroNectin™ before and/or during transduction. In certain embodiments, the method comprises pre-stimulation by culturing the cells on plates coated with about 2 ug/cm$^2$ RetroNectin™ (RN). In some embodiments, cells are transduced in liquid media comprising Retro-Nectin™. In some embodiments, cells are pre-treated by culturing on dishes coated with a recombinant fibronectin fragment and also transduced in liquid culture in the presence of the recombinant fibronectin fragment and other TEs.

In certain embodiments of any of the methods disclosed herein, the cells are contacted with a solution or culture media comprising the two or more transduction enhancers. The solution or culture media may further comprise the recombinant retroviral vector, or the recombinant retroviral vector may be added after the cells have been contacted with the solution or culture media comprising the transduction enhancers. In particular embodiments, the cells are present in a culture dish comprising the solution or culture media. In particular embodiments, the culture dish is coated with a recombinant fibronectin fragment. The cells may be contacted with the retroviral vector under conditions and for a time sufficient to permit transduction of the cells by the retroviral vector, e.g., in suitable culture media for at least one hour, at least two hours, at least four hours, at least eight hours, at least twelve hours, or at least 16 hours. In some embodiments, the cells are transduced either once or two consecutive times, e.g., following pre-stimulation, with each transduction cycle being between 12 and 24 hours, or between 16-18 hours. In some embodiments, the cells are contacted with the retroviral vector and the transduction enhancers during the same or an overlapping period of time.

In some embodiments of any of the methods disclosed herein, the cells are contacted with a poloxamer. In an embodiment, the poloxamer is selected from the group consisting of poloxamer 288, poloxamer 335, poloxamer 338, and poloxamer 407. In an embodiment, the poloxamer is poloxamer 338 (LentiBOOST™). LentiBOOST™ can be used at a final concentration of about 50 μg/mL to about 1,500 μg/mL, about 500 μg/mL to about 1,500 μg/mL, about 750 μg/mL to about 1,250 μg/mL, about 900 μg/mL, about 900 μg/mL, about 950 μg/mL, about 1000 μg/mL, about 1050 μg/mL, about 1100 μg/mL, or about 1150 μg/mL.

In some embodiments of any of the methods disclosed herein, the cells are contacted with PGE2 or a derivative thereof. In an embodiment, the PGE2 or derivative thereof is modified. In an embodiment, the PGE2 or derivative thereof is dimethylated PGE2. In an embodiment, the dimethylated PGE2 is 16,16-dimethyl Prostaglandin E2. 16,16-dimethyl Prostaglandin E2 has the following structure (represented as a "skeletal structure", also called "line-angle formula" or "shorthand formula"):

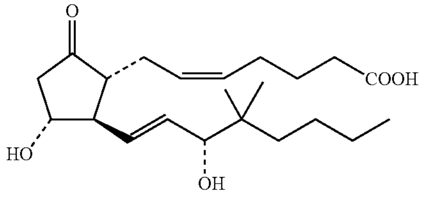 [SMILES: CCCCC(C)(C)[C@H](O)/C=C/[C@H]1[C@H](O)CC(=O)[C@@H]1C/C=C\CCCC(=O)O]

Molecular Formula: $C_{22}H_{36}O_5$

In some embodiments, the PGE2 or derivative thereof is unmodified.

In some embodiments, PGE2 or derivative thereof can be used at a final concentration of about 1 μM to about 200 μM, about 10 μM to about 20 μM, about 20 μM to about 40 μM, about 40 μM to about 60 μM, about 60 μM to about 80 μM, about 5 μM, about 10 μM, about 15 μM, about 20 μM, about 25 μM, about 30 μM, about 35 μM, or about 40 μM. PGE2 or derivative thereof can be used at a final concentration of about 0.3 μM to about 70 μg/ml, about 3 μg/ml to about 7 μg/ml, about 7 μg/ml to about 13 μg/ml, about 13 μg/ml to about 20 μg/ml, about 20 μg/ml to about 26 μg/ml, about 2 μg/ml, about 3 μg/ml, about 4 μg/ml, about 5 μg/ml, about 6 μg/ml, about 7 μg/ml, about 8 μg/ml, about 9 μg/ml, about 10 μg/ml, about 11 μg/ml, about 12 μg/ml, about 13 μg/ml, about 14 μg/ml, or about 15 μg/ml.

In some embodiments of any of the methods disclosed herein, the method comprises contacting the hematopoietic cells with protamine sulfate. Protamine sulfate can be used at a final concentration of about 4 μg/mL to about 15 μg/mL, about 5 μg/mL to about 10 μg/mL, or about 5 μg/mL, about 6 μg/mL, about 7 μg/mL, about 8 μg/mL, about 9 μg/mL, about 10 μg/mL, about 11 μg/mL, about 12 μg/mL, about 13 μg/mL, about 14 μg/mL or about 15 μg/mL or more. In certain embodiments, protamine sulfate can be used at a final concentration of about 1 μg/mL to about 5 μg/mL, about 3 μg/mL to about 5 μg/mL, or about 1 μg/mL, about 2 μg/mL, about 3 μg/mL, about 4 μg/mL, or about 5 μg/mL.

In some embodiments of any of the methods disclosed herein, the cells are contacted with a poloxamer 338 and PGE2 or a derivative thereof. In an embodiment, the poloxamer 338 and PGE2 or derivative thereof is used at final concentrations of about 900 μg/mL and about 3 μg/mL to about 7 μg/mL, respectively, or about 900 μg/mL and about 2 μg/ml, respectively, or about 900 μg/mL and about 3 μg/ml, respectively, or about 900 μg/mL and about 3 μg/ml, respectively, or about 900 μg/mL and about 4 μg/ml, respectively, or about 900 μg/mL and about 5 μg/ml, respectively, or about 900 μg/mL and about 6 μg/ml, respectively, or about 900 μg/mL and about 7 μg/ml, respectively, or about 900 μg/mL and about 8 μg/ml, respectively, or about 900 μg/mL and about 9 μg/ml, respectively. In any of the foregoing embodiments, protamine sulfate may, optionally, used at a final concentration of about 3 μg/ml to about 7 μg/ml, about 1 μg/mL to about 5 μg/mL, about 3 μg/mL to about 5 μg/mL, or about 1 μg/mL, about 2 μg/mL, about 3 μg/mL, about 4 μg/mL, about 5 μg/mL, or about 6 μg/mL.

In some embodiments, the poloxamer 338 and PGE2 or derivative thereof is used at final concentrations of about 950 μg/mL and about 3 μg/ml to about 7 μg/ml, respectively, or about 900 μg/mL and about 2 μg/ml, respectively, or about 950 μg/mL and about 3 μg/ml, respectively, or about 950 μg/mL and about 3 μg/ml, respectively, or about 950 μg/mL and about 4 μg/ml, respectively, or about 950 μg/mL and about 5 μg/ml, respectively, or about 950 μg/mL and about 6 μg/ml, respectively, or about 950 μg/mL and about 7 μg/ml, respectively, or about 950 μg/mL and about 8 μg/ml, respectively, or about 950 μg/mL and about 9 μg/ml, respectively. In any of the foregoing embodiments, protamine sulfate may, optionally, used at a final concentration of about 3 μg/ml to about 7 μg/ml, about 1 μg/mL to about 5 μg/mL, about 3 μg/mL to about 5 μg/mL, or about 1 μg/mL, about 2 μg/mL, about 3 μg/mL, about 4 μg/mL, about 5 μg/mL, or about 6 μg/mL.

In some embodiments, the poloxamer 338 and PGE2 or derivative thereof is used at final concentrations of about 1000 μg/mL and about 3 μg/ml to about 7 μg/ml, respectively, or about 1000 μg/mL and about 2 μg/ml, respectively, or about 1000 μg/mL and about 3 μg/ml, respectively, or about 1000 μg/mL and about 3 μg/ml, respectively, or about 1000 μg/mL and about 4 μg/ml, respectively, or about 1000 μg/mL and about 5 μg/ml, respectively, or about 1000 μg/mL and about 6 μg/ml, respectively, or about 1000 μg/mL and about 7 μg/ml, respectively, or about 1000 μg/mL and about 8 μg/ml, respectively, or about 1000 μg/mL and about 9 μg/ml, respectively. In any of the foregoing embodiments, protamine sulfate may, optionally, used at a final concentration of about 3 μg/ml to about 7 μg/ml, about 1 μg/mL to about 5 μg/mL, about 3 μg/mL to about 5 μg/mL, or about 1 μg/mL, about 2 μg/mL, about 3 μg/mL, about 4 μg/mL, about 5 μg/mL, or about 6 μg/mL.

In some embodiments, the poloxamer 338 and PGE2 or derivative thereof is used at final concentrations of about 1050 μg/mL and about 3 μg/ml to about 7 μg/ml, respectively, or about 1050 μg/mL and about 2 μg/ml, respectively, or about 1050 μg/mL and about 3 μg/ml, respectively, or about 1050 μg/mL and about 3 μg/ml, respectively, or about 1050 μg/mL and about 4 μg/ml, respectively, or about 1050 μg/mL and about 5 μg/ml, respectively, or about 1050 μg/mL and about 6 μg/ml, respectively, or about 1050 μg/mL and about 7 μg/ml, respectively, or about 1050 μg/mL and about 8 μg/ml, respectively, or about 1050 μg/mL and about 9 μg/ml, respectively. In any of the foregoing embodiments, protamine sulfate may, optionally, used at a final concentration of about 3 μg/ml to about 7 μg/ml, about 1 μg/mL to about 5 μg/mL, about 3 μg/mL to about 5 μg/mL, or about 1 μg/mL, about 2 μg/mL, about 3 μg/mL, about 4 μg/mL, about 5 μg/mL, or about 6 μg/mL.

In some embodiments of any of the methods disclosed herein, the cells are contacted with a poloxamer 338 and PGE2 or a derivative thereof. In an embodiment, the poloxamer 338 and PGE2 or derivative thereof is used at final concentrations of about 0.5 mg/mL and about 3 μg/mL to about 7 μg/mL, respectively, or about 0.5 mg/mL and about 2 μg/ml, respectively, or about 0.5 mg/mL and about 3 μg/ml, respectively, or about 900 μg/mL and about 3 μg/ml, respectively, or about 0.5 mg/mL and about 4 μg/ml, respectively, or about 0.5 mg/mL and about 5 μg/ml, respectively, or about 0.5 mg/mL and about 6 μg/ml, respectively, or about 0.5 mg/mL and about 7 μg/ml, respectively, or about 0.5 mg/mL and about 8 μg/ml, respectively, or about 0.5 mg/mL and about 9 μg/ml, respectively. In any of the foregoing embodiments, protamine sulfate may, optionally, used at a final concentration of about 3 μg/ml to about 7 μg/ml, about 1 μg/mL to about 5 μg/mL, about 3 μg/mL to about 5 μg/mL, or about 1 μg/mL, about 2 μg/mL, about 3 μg/mL, about 4 μg/mL, about 5 μg/mL, or about 6 μg/mL.

In some embodiments of any of the methods disclosed herein, the cells are contacted with a poloxamer 338 and PGE2 or a derivative thereof. In an embodiment, the poloxamer 338 and PGE2 or derivative thereof is used at final concentrations of about 1 mg/mL and about 3 μg/mL to about 7 μg/mL, respectively, or about 1 mg/mL and about 2 μg/ml, respectively, or about 1 mg/mL and about 3 μg/ml, respectively, or about 900 μg/mL and about 3 μg/ml, respectively, or about 1 mg/mL and about 4 μg/ml, respectively, or about 1 mg/mL and about 5 g/ml, respectively, or about 1 mg/mL and about 6 μg/ml, respectively, or about 1 mg/ml and about 7 μg/ml, respectively, or about 1 mg/mL and about 8 μg/ml, respectively, or about 1 mg/mL and about 9 μg/ml, respectively. In any of the foregoing embodiments, protamine sulfate may, optionally, used at a final concentration of about 3 μg/ml to about 7 g/ml, about 1 μg/mL to about 5 μg/mL, about 3 μg/mL to about 5 μg/mL, or about 1 μg/mL, about 2 μg/mL, about 3 μg/mL, about 4 μg/mL, about 5 μg/mL, or about 6 μg/mL.

In some embodiments of any of the methods disclosed herein, the cells are contacted with a poloxamer 338 and PGE2 or a derivative thereof. In an embodiment, the poloxamer 338 and PGE2 or derivative thereof is used at final concentrations of about 2 mg/mL and about 3 μg/mL to about 7 μg/mL, respectively, or about 2 mg/mL and about 2 μg/ml, respectively, or about 2 mg/mL and about 3 μg/ml, respectively, or about 900 μg/mL and about 3 μg/ml, respectively, or about 2 mg/mL and about 4 μg/ml, respectively, or about 2 mg/mL and about 5 μg/ml, respectively, or about 2 mg/mL and about 6 μg/ml, respectively, or about 2 mg/mL and about 7 μg/ml, respectively, or about 2 mg/mL and about 8 μg/ml, respectively, or about 2 mg/mL and about 9 μg/ml, respectively. In any of the foregoing embodiments, protamine sulfate may, optionally, used at a final concentration of about 3 μg/ml to about 7 μg/ml, about 1 μg/mL to about 5 μg/mL, about 3 μg/mL to about 5 μg/mL, or about 1 μg/mL, about 2 μg/mL, about 3 μg/mL, about 4 μg/mL, about 5 μg/mL, or about 6 μg/mL.

In some embodiments of any of the methods disclosed herein, the cells are contacted with a poloxamer 338 and PGE2 or a derivative thereof. In an embodiment, the poloxamer 338 and PGE2 or derivative thereof is used at final concentrations of about 4 mg/mL and about 3 μg/mL to about 7 μg/mL, respectively, or about 4 mg/mL and about 2 μg/ml, respectively, or about 4 mg/mL and about 3 μg/ml, respectively, or about 900 μg/mL and about 3 μg/ml, respectively, or about 4 mg/mL and about 4 μg/ml, respectively, or about 4 mg/mL and about 5 μg/ml, respectively, or about 4 mg/mL and about 6 μg/ml, respectively, or about 4 mg/mL and about 7 μg/ml, respectively, or about 4 mg/mL and about 8 μg/ml, respectively, or about 4 mg/mL and about 9 μg/ml, respectively. In any of the foregoing embodiments, protamine sulfate may, optionally, used at a final concentration of about 3 μg/ml to about 7 μg/ml, about 1 μg/mL to about 5 μg/mL, about 3 μg/mL to about 5 μg/mL, or about 1 μg/mL, about 2 μg/mL, about 3 μg/mL, about 4 μg/mL, about 5 μg/mL, or about 6 μg/mL.

In some embodiments of any of the methods disclosed herein, the cells are contacted with a poloxamer 338 and PGE2 or a derivative thereof. In an embodiment, the poloxamer 338 and PGE2 or derivative thereof is used at final concentrations of about 0.5 mg/mL to about 4 mg/mL and about 3 μg/mL to about 7 μg/mL, respectively, or about 0.5 mg/mL to about 4 mg/mL and about 2 μg/ml, respectively, or about 0.5 mg/mL to about 4 mg/mL and about 3 μg/ml, respectively, or about 900 μg/mL and about 3 μg/ml, respectively, or about 0.5 mg/ml to about 4 mg/mL and about 4 μg/ml, respectively, or about 0.5 mg/mL to about 4 mg/mL and about 5 μg/ml, respectively, or about 0.5 mg/mL to about 4 mg/mL and about 6 μg/ml, respectively, or about 0.5 mg/mL to about 4 mg/mL and about 7 μg/ml, respectively, or about 0.5 mg/mL to about 4 mg/mL and about 8 μg/ml, respectively, or about 0.5 mg/mL to about 4 mg/mL and about 9 μg/ml, respectively. In any of the foregoing embodiments, protamine sulfate may, optionally, used at a final concentration of about 3 μg/ml to about 7 μg/ml, about 1 μg/mL to about 5 μg/mL, about 3 μg/mL to about 5 μg/mL, or about 1 μg/mL, about 2 μg/mL, about 3 μg/mL, about 4 μg/mL, about 5 μg/mL, or about 6 μg/mL.

In preferred embodiments, the cells are transduced with a lentiviral vector in a medium containing poloxamer 338 at about 0.5 mg/mL to about 4 mg/mL; PGE2 at about 10 μg/mL to about 50 μg/mL; and protamine sulfate at about 1 μg/mL to about 10 μg/mL. In adherent mode, the substrate is, in some cases, coated with the CH296 fragment of human fibronectin, tradename RetroNectin™, using a RetroNectin™ solution at a concentration of about 20 μg/mL to about 100 μg/mL.

In preferred embodiments, the cells are contacted with poloxamer 338 at about 0.5 mg/mL to about 4 mg/mL; PGE2 at about 10 μg/mL to about 50 μg/mL; and protamine sulfate at about 1 μg/mL to about 10 μg/mL.

In preferred embodiments, the cells are transduced with a lentiviral vector in a medium containing poloxamer 338 at about 1 mg/mL; PGE2 at about 10 μM; and protamine sulfate at about 4 μg/mL. In adherent mode, the substrate is, in some cases, coated with the CH296 fragment of human fibronectin, tradename RetroNectin™, using a RetroNectin™ solution at a concentration of about 20 μg/mL. In certain embodiments, culture dishes are coated with 2 μg/cm$^2$ RetroNectin™. In certain embodiments, the method comprises pre-stimulation by culturing the cells on plates coated with a recombinant fibronectin fragment, e.g., RetroNectin™ (RN).

In preferred embodiments, the cells are contacted with poloxamer 338 at about 1 mg/mL; PGE2 at about 10 μM; and protamine sulfate at about 4.

Further illustrative embodiments are provided in Table 1 and Table 2. Any of the indicated combinations and concentrations of transduction enhancers may be used according to the disclosed methods, and with other types of cells. In addition, any of the indicated combinations may be used further in combination with a recombinant fibronectin, such as RetroNectin™, such as where culture dishes used for transduction are coated with RetroNectin™

TABLE 1

Combinations of CB Cells and Transduction Enhancers

| | Cells | LentiBOOST | PGE2 | Protamine Sulfate |
|---|---|---|---|---|
| 1 | CD34-enriched cord blood (CB) cells | — | 10 μg/mL | — |
| 2 | CD34-enriched cord blood (CB) cells | — | 30 μg/mL | — |
| 3 | CD34-enriched cord blood (CB) cells | — | 50 μg/mL | — |
| 4 | CD34-enriched cord blood (CB) cells | 0.5 mg/mL | 10 μg/mL | — |
| 5 | CD34-enriched cord blood (CB) cells | 0.5 mg/mL | 30 μg/mL | — |
| 6 | CD34-enriched cord blood (CB) cells | 0.5 mg/mL | 50 μg/mL | — |
| 7 | CD34-enriched cord blood (CB) cells | 1 mg/mL | 10 μg/mL | — |
| 8 | CD34-enriched cord blood (CB) cells | 1 mg/mL | 30 μg/mL | — |
| 9 | CD34-enriched cord blood (CB) cells | 1 mg/mL | 50 μg/mL | — |
| 10 | CD34-enriched cord blood (CB) cells | 2 mg/mL | 10 μg/mL | — |
| 11 | CD34-enriched cord blood (CB) cells | 2 mg/mL | 30 μg/mL | — |
| 12 | CD34-enriched cord blood (CB) cells | 2 mg/mL | 50 μg/mL | — |
| 13 | CD34-enriched cord blood (CB) cells | 4 mg/mL | 10 μg/mL | — |
| 14 | CD34-enriched cord blood (CB) cells | 4 mg/mL | 30 μg/mL | — |
| 15 | CD34-enriched cord blood (CB) cells | 4 mg/mL | 50 μg/mL | — |
| 16 | CD34-enriched cord blood (CB) cells | — | 10 μg/mL | 4 μg/mL |
| 17 | CD34-enriched cord blood (CB) cells | — | 30 μg/mL | 4 μg/mL |
| 18 | CD34-enriched cord blood (CB) cells | — | 50 μg/mL | 4 μg/mL |
| 19 | CD34-enriched cord blood (CB) cells | 0.5 mg/mL | 10 μg/mL | 4 μg/mL |
| 20 | CD34-enriched cord blood (CB) cells | 0.5 mg/mL | 30 μg/mL | 4 μg/mL |
| 21 | CD34-enriched cord blood (CB) cells | 0.5 mg/mL | 50 μg/mL | 4 μg/mL |
| 22 | CD34-enriched cord blood (CB) cells | 1 mg/mL | 10 μg/mL | 4 μg/mL |
| 23 | CD34-enriched cord blood (CB) cells | 1 mg/mL | 30 μg/mL | 4 μg/mL |
| 24 | CD34-enriched cord blood (CB) cells | 1 mg/mL | 50 μg/mL | 4 μg/mL |
| 25 | CD34-enriched cord blood (CB) cells | 2 mg/mL | 10 μg/mL | 4 μg/mL |
| 26 | CD34-enriched cord blood (CB) cells | 2 mg/mL | 30 μg/mL | 4 μg/mL |
| 27 | CD34-enriched cord blood (CB) cells | 2 mg/mL | 50 μg/mL | 4 μg/mL |
| 28 | CD34-enriched cord blood (CB) cells | 4 mg/mL | 10 μg/mL | 4 μg/mL |
| 29 | CD34-enriched cord blood (CB) cells | 4 mg/mL | 30 μg/mL | 4 μg/mL |
| 30 | CD34-enriched cord blood (CB) cells | 4 mg/mL | 50 μg/mL | 4 μg/mL |

TABLE 2

Combinations of mPB Cells and Transduction Enhancers

| | Cells | LentiBOOST | PGE2 | Protamine Sulfate |
|---|---|---|---|---|
| 1 | Mobilized peripheral blood mononuclear cells, CD34-enriched | — | 10 μg/mL | — |
| 2 | Mobilized peripheral blood mononuclear cells, CD34-enriched | — | 30 μg/mL | — |
| 3 | Mobilized peripheral blood mononuclear cells, CD34-enriched | — | 50 μg/mL | — |

TABLE 2-continued

| | Combinations of mPB Cells and Transduction Enhancers | | | |
|---|---|---|---|---|
| | Cells | LentiBOOST | PGE2 | Protamine Sulfate |
| 4 | Mobilized peripheral blood mononuclear cells, CD34-enriched | 0.5 mg/mL | 10 μg/mL | — |
| 5 | Mobilized peripheral blood mononuclear cells, CD34-enriched | 0.5 mg/mL | 30 μg/mL | — |
| 6 | Mobilized peripheral blood mononuclear cells, CD34-enriched | 0.5 mg/mL | 50 μg/mL | — |
| 7 | Mobilized peripheral blood mononuclear cells, CD34-enriched | 1 mg/mL | 10 μg/mL | — |
| 8 | Mobilized peripheral blood mononuclear cells, CD34-enriched | 1 mg/mL | 30 μg/mL | — |
| 9 | Mobilized peripheral blood mononuclear cells, CD34-enriched | 1 mg/mL | 50 μg/mL | — |
| 10 | Mobilized peripheral blood mononuclear cells, CD34-enriched | 2 mg/mL | 10 g/mL | — |
| 11 | Mobilized peripheral blood mononuclear cells, CD34-enriched | 2 mg/mL | 30 μg/mL | — |
| 12 | Mobilized peripheral blood mononuclear cells, CD34-enriched | 2 mg/mL | 50 μg/mL | — |
| 13 | Mobilized peripheral blood mononuclear cells, CD34-enriched | 4 mg/mL | 10 μg/mL | — |
| 14 | Mobilized peripheral blood mononuclear cells, CD34-enriched | 4 mg/mL | 30 μg/mL | — |
| 15 | Mobilized peripheral blood mononuclear cells, CD34-enriched | 4 mg/mL | 50 μg/mL | — |
| 16 | Mobilized peripheral blood mononuclear cells, CD34-enriched | — | 10 μg/mL | 4 μg/mL |
| 17 | Mobilized peripheral blood mononuclear cells, CD34-enriched | — | 30 μg/mL | 4 μg/mL |
| 18 | Mobilized peripheral blood mononuclear cells, CD34-enriched | — | 50 g/mL | 4 μg/mL |
| 19 | Mobilized peripheral blood mononuclear cells, CD34-enriched | 0.5 mg/mL | 10 μg/mL | 4 μg/mL |
| 20 | Mobilized peripheral blood mononuclear cells, CD34-enriched | 0.5 mg/mL | 30 g/mL | 4 μg/mL |
| 21 | Mobilized peripheral blood mononuclear cells, CD34-enriched | 0.5 mg/mL | 50 μg/mL | 4 μg/mL |
| 22 | Mobilized peripheral blood mononuclear cells, CD34-enriched | 1 mg/mL | 10 μg/mL | 4 μg/mL |
| 23 | Mobilized peripheral blood mononuclear cells, CD34-enriched | 1 mg/mL | 30 μg/mL | 4 μg/mL |
| 24 | Mobilized peripheral blood mononuclear cells, CD34-enriched | 1 mg/mL | 50 μg/mL | 4 μg/mL |
| 25 | Mobilized peripheral blood mononuclear cells, CD34-enriched | 2 mg/mL | 10 μg/mL | 4 μg/mL |
| 26 | Mobilized peripheral blood mononuclear cells, CD34-enriched | 2 mg/mL | 30 μg/mL | 4 μg/mL |
| 27 | Mobilized peripheral blood mononuclear cells, CD34-enriched | 2 mg/mL | 50 μg/mL | 4 μg/mL |
| 28 | Mobilized peripheral blood mononuclear cells, CD34-enriched | 4 mg/mL | 10 μg/mL | 4 μg/mL |
| 29 | Mobilized peripheral blood mononuclear cells, CD34-enriched | 4 mg/mL | 30 μg/mL | 4 μg/mL |
| 30 | Mobilized peripheral blood mononuclear cells, CD34-enriched | 4 mg/mL | 50 μg/mL | 4 μg/mL |

In some embodiments, contacting steps are performed simultaneously or during an overlapping time period.

In some embodiments, the concentration of the PGE2 or derivative thereof is 5-30 μg/mL.

In some embodiments, the concentration of the PGE2 or derivative thereof is about 10 μg/mL.

In some embodiments, the concentration of the poloxamer is 200-1200 μg/mL.

In some embodiments, the concentration of the poloxamer is about 1000 μg/mL.

In some embodiments, the concentration of the protamine sulfate is 4-10 μg/mL.

In some embodiments, the concentration of the protamine sulfate is about 4 μg/mL.

In some embodiments, the hematopoietic cells have been or are cultured on vessels coated with recombinant fibronectin or a fragment thereof that enhances transduction efficiency. Recombinant fibronectin fragment (e.g., the CH296 fragment of human fibronectin, tradename RetroNectin™) promotes co-localization of lentivirus or retrovirus with target cells and enhances transduction efficiency.

In some embodiments, the method comprises contacting the hematopoietic cells with recombinant fibronectin fragment, poloxamer, and PGE2.

In some embodiments, the method comprises contacting the hematopoietic cells with recombinant fibronectin fragment, poloxamer, and protamine sulfate. In some embodiments, the method comprises contacting the hematopoietic cells with recombinant fibronectin fragment, poloxamer, PGE2, and protamine sulfate.

In some embodiments, the method comprises contacting the hematopoietic cells with recombinant fibronectin fragment, PGE2, and protamine sulfate.

In certain embodiments of any of the methods disclosed herein, the cells are contacted with the transduction enhancers during the same or an overlapping time period. In certain embodiments, the cells are also contacted with a recombinant retroviral vector, e.g., during the same or an overlapping time period as when the cells are contacted with the transduction enhancers. In certain embodiments, the cells are present in vessels comprising a solution or culture media, wherein the transduction enhancers are present in the vessels and/or culture media.

Prostaglandins

Prostaglandins relate generally to hormone-like molecules that are derived from fatty acids containing 20 carbon atoms, including a 5-carbon ring, as described herein and known in the art. Prostaglandin E2 (PGE2), also known as dinoprostone, is a naturally occurring prostaglandin which is used as a medication. PGE2 has the following structure (represented as a "skeletal structure", also called "line-angle formula" or "shorthand formula"):

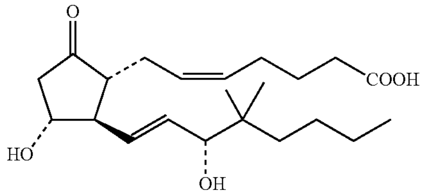 [SMILES: CCCCC(C)(C)[C@H](O)/C=C/[C@H]1[C@H](O)CC(=O)[C@@H]1C/C=C\CCCC(=O)O]

PGE2 Molecular Formula: $C_{22}H_{36}O_5$

Prostaglandin E2 (PGE2) has been shown to increase the level of lentiviral transgene delivery in ex vivo culture of CD34+ cells. Heffner et al. *Mol Ther.* 2018 Jan. 3; 26 (1): 320-328.

Illustrative examples of PGE2 "analogs" or "derivatives" include, but are not limited to, 16,16-dimethyl $PGE_2$ ($dmPGE_2$), 16-16 dimethyl $PGE_2$ p-(p-acetamidobenzamido) phenyl ester, 11-deoxy-16,16-dimethyl $PGE_2$, 9-deoxy-9-methylene-16,16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15 (S)-15-methyl $PGE_2$, 15(R)-15-methyl $PGE_2$, 8-iso-15-keto $PGE_2$, 8-iso $PGE_2$ isopropyl ester, 20-hydroxy $PGE_2$, nocloprost, sulprostone, butaprost, 15-keto $PGE_2$, and 19 (R) hydroxy $PGE_2$.

Also contemplated herein are prostaglandin analogs or derivatives having a similar structure to $PGE_2$ that are substituted with halogen at the 9-position (see, e.g., WO 2001/12596, herein incorporated by reference in its entirety), as well as 2-decarboxy-2-phosphinico prostaglandin derivatives, such as those described in U.S. Publication No. 2006/0247214, herein incorporated by reference in its entirety.

Poloxamers

Poloxamers are nonionic triblock copolymers composed of a central hydrophobic chain of polyoxypropylene (poly (propylene oxide)) flanked by two hydrophilic chains of polyoxyethylene (poly(ethylene oxide)). Poloxamers are also known by the trade names Synperonics,® Pluronics® and Kolliphor®. Because the lengths of the polymer blocks can be customized, many different poloxamers exist. Poloxamers are commonly named with the letter P (for poloxamer) followed by three digits: the first two digits multiplied by 100 give the approximate molecular mass of the polyoxypropylene core, and the last digit multiplied by 10 gives the percentage polyoxyethylene content (e.g., P407=poloxamer with a polyoxypropylene molecular mass of 4000 g/mol and a 70% polyoxyethylene content).

In particular embodiments, the poloxamer has an average molecular weight of polypropylene subunits of at least about 2750 Daltons. In particular embodiments, the poloxamer has an average molecular weight of polypropylene subunits of at least about 3250 Daltons. In particular embodiments, the poloxamer has an average molecular weight of polypropylene subunits of at least about 4000 Daltons or at least about 10,000 Daltons.

In particular embodiments, the poloxamer comprises at least about 50% polyethylene oxide. In particular embodiments, the poloxamer comprises at least about 60% polyethylene oxide. In particular embodiments, the poloxamer comprises at least about 70% polyethylene oxide. In particular embodiments, the poloxamer comprises at least about 80% polyethylene oxide.

In particular embodiments, the poloxamer has an average molecular weight of polypropylene subunits of at least about 2750 Daltons and the poloxamer comprises at least about 40% polyethylene oxide. In particular embodiments, the poloxamer has an average molecular weight of polypropylene subunits of at least about 2750 Daltons and the poloxamer comprises at least about 50% polyethylene oxide. In particular embodiments, the poloxamer has an average molecular weight of polypropylene subunits of at least about 3250 Daltons and the poloxamer comprises at least about 50% polyethylene oxide.

In certain embodiments, the poloxamer is selected from the group consisting of: poloxamer 288, poloxamer 335, poloxamer 338, and poloxamer 407. In one embodiment, the poloxamer is poloxamer 288. In one embodiment, the poloxamer is poloxamer 335. In one embodiment, the poloxamer is poloxamer 338. In one embodiment, the poloxamer is poloxamer 407. In an embodiment, the recombinant retroviral vector is a recombinant lentiviral vector.

Recently, the poloxamer F108 has been shown to improve transduction of hematopoietic cells. Hoefig et al. *J Gene Med.* 2012 August; 14 (8): 549-60; U.S. Pat. No. 9,771,599. Inclusion of poloxamer in a standard hematopoietic stem cell (HSC) transduction protocol yields high transduction efficiencies, while preserving the ability of the transduced HSC to differentiate into various hematopoietic lineages. Hauber at al. *Hum Gene Ther Methods.* 2018 April; 29 (2): 104-113.

Recombinant Fibronectin Fragment

A recombinant fibronectin fragment may be any fragment of the protein fibronectin, e.g., human fibronectin, that promotes enhances transduction efficiency. Without being bound by theory, it is believed that recombinant fibronectin fragment promotes co-localization of lentivirus or retrovirus with target cells. An example of a recombinant fibronectin fragment is the CH296 fragment of human fibronectin, tradename RetroNectin™.

Hematopoietic Cells

Hematopoietic cells that may be transduced according to the methods disclosed herein include any hematopoietic cells or population thereof. In certain embodiments, the hematopoietic cells are mammalian, e.g., human, hematopoietic cells obtained from a mammal. In certain embodiments, the cells are obtained from a human who is to be treated with the hematopoietic cells after they have been transduced according to a method disclosed herein. In an embodiment, the hematopoietic cells have been enriched for CD34+ cells. In certain embodiments, the hematopoietic cells are CD34-enriched cell populations obtained from a biological sample obtained from a subject. In one embodiment, the biological sample is a bone marrow sample. In another embodiment, the biological sample is peripheral blood. In another embodiment, the biological sample is cord blood.

In particular embodiments, the biological sample, e.g., peripheral blood, is obtained from the subject following mobilization of hematopoietic stem cells (HSCs). In one embodiment, HSCs and/or progenitor cells are mobilized by treating the subject with G-CSF or an analog thereof. HSCs and progenitor cells (HSPC) in peripheral blood may be mobilized prior to collection of the biological sample. Peripheral blood HSCs and HSPC can be mobilized by any method known in the art. Peripheral blood HSCs and HSPC can be mobilized by treating the subject with any agent(s), described herein or known in the art, that increase the number of HSPC circulating in the peripheral blood of the subject. For example, in particular embodiments, peripheral blood is mobilized by treating the subject with one or more cytokines or growth factors (e.g., G-CSF, kit ligand (KL), IL-I, IL-7, IL-8, IL-11, Flt3 ligand, SCF, thrombopoietin, or GM-CSF (such as sargramostim)). Different types of G-CSF that can be used in the methods for mobilization of peripheral blood include filgrastim and longer acting G-CSF: pegfilgrastim. In particular embodiments, peripheral blood is mobilized by treating the subject with one or more chemokines (e.g., macrophage inflammatory protein-1a (MIP1a/CCL3)), chemokine receptor ligands (e.g., chemokine receptor 2 ligands GRO13 and GR013M), chemokine receptor analogs (e.g., stromal cell derived factor-1a (SDF-1a) protein analogs such as CTCE-0021, CTCE-0214, or SDF-1a such as Met-SDF-113), or chemokine receptor antagonists (e.g., chemokine (C—X—C motif) receptor 4 (CXCR4) antagonists such as AMD3100). In particular embodiments, peripheral blood is mobilized by treating the subject with one or more anti-integrin signaling agents (e.g., function blocking anti-very late antigen 4 (VLA-4) antibody, or anti-vascular cell adhesion molecule 1 (VCAM-1)). In particular embodiments, peripheral blood is mobilized by treating the subject with one or more cytotoxic drugs such as cyclophosphamide, etoposide or paclitaxel. In particular embodiments, peripheral blood can be mobilized by administering to a subject one or more of the agents listed above for a certain period of time. For example, the subject can be treated with one or more agents (e.g., G-CSF) via injection (e.g., subcutaneous, intravenous or intraperitoneal), once daily or twice daily, for 1, 2, 3, 4, 5, 6, 7, 8, 9, 10, 11, 12, 13 or 14 days prior to collection of HSPC. In specific embodiments, HSPC are collected within 1, 2, 3, 4, 5, 6,7, 8, 12, 14, 16, 18, 20 or 24 hours after the last dose of an agent used for mobilization of HSPC into peripheral blood. In particular embodiments, HSCs and HSPC are mobilized by treating the subject with two or more different types of agents described above or known in the art, such as a growth factor (e.g., G-CSF) and a chemokine receptor antagonist (e.g., CXCR4 receptor antagonist such as AMD3100), or a growth factor (e.g., G-CSF or KL) and an anti-integrin agent (e.g., function blocking VLA-4 antibody). In one embodiment, HSCs and/or progenitor cells are mobilized by treating the subject with G-CSF or an analog thereof. In one embodiment, the G-CSF is filgrastim. In one embodiment, HSCs and/or progenitor cells are mobilized by treating the subject with plerixafor. In a certain embodiment, HSCs and/or progenitor cells are mobilized using a combination of filgrastim and plerixafor, by filgrastim alone, or by plerixafor alone. In particular embodiments, different types of mobilizing agents are administered concurrently or sequentially. For additional information regarding methods of mobilization of peripheral blood see, e.g., Craddock et al., 1997, Blood 90 (12): 4779-4788; Jin et al., 2008, Journal of Translational Medicine 6:39; Pelus, 2008, Curr. Opin. Hematol. 15 (4): 285-292; Papayannopoulou et al., 1998, Blood 91 (7): 2231-2239; Tricot et al., 2008, Haematologica 93 (11): 1739-1742; and Weaver et al., 2001, Bone Marrow Transplantation 27 (2): S23-S29).

In certain embodiments, peripheral blood is obtained through a syringe or catheter inserted into a subject's vein. For example, the peripheral blood can be collected using an apheresis machine. Blood flows from the vein through the catheter into an apheresis machine, which separates the white blood cells, including HSPC from the rest of the blood and then returns the remainder of the blood to the subject's body. Apheresis can be performed for several hours over successive days (e.g., 1 to 5 days) until enough HSPC have been collected.

In certain embodiments, bone marrow is obtained from the posterior iliac crest of the subject by needle aspiration (see, e.g., Koda et al., 1984, J. Clin Invest. 73:1377-1384).

In certain embodiments, a hematocrit level of the biological sample may be determined. The hematocrit level may be determined by centrifuging the sample within a treatment chamber to separate RBCs of a sample into a layer such that the packed cell volume may be determined. It should be appreciated that the sample may be combined with an anticoagulant in order to assist with determining the hematocrit level and that such an anticoagulant may be added to the treatment chamber prior to or during centrifugation. Alternatively, the hematocrit level may be determined by measuring optical properties of the sample. For example, a spectrometer may be used to analyze the sample. It should be appreciated that any type of known spectroscopic methods of determining hematocrit level may be used such as, for example, Raman spectroscopy and/or light scattering techniques.

In certain embodiments, the biological sample is depleted of erythrocytes, e.g., before preparing the one or more cell populations enriched for CD34+ cells from the biological sample. In some embodiments, the cells remaining after depletion techniques are washed. In another embodiment, non-specific IgG is added to the washed cells. In some embodiments, the non-specific IgG is flebogamma.

In some cases, two or more biological samples are mixed together before CD34+ selection, including, e.g. bone marrow samples acquired at different times, such as 1, 2, 3, 4 or more days apart, or 1, 2, or 3 weeks apart, or 1, 2, or 3 months apart, or years apart, inclusive of other time increments.

Enrichment of Hematopoietic Cells for CD34+ Cells

In some embodiments, the hematopoietic cells are CD34-positive hematopoietic cells. Typically CD34+ cells are prepared by high stringency enrichment for CD34. Alternatively or in addition to high-stringency enrichment, low-stringency enrichment for CD34 may be performed.

As used herein, "high stringency" or "high stringency conditions" refers to a method of enriching for a cell population intended to result in substantial enrichment of cells for cells expressing a particular biological marker, e.g. CD34. For example, "high stringency" CD34 enrichment used clinically results in mean: 61.6% and median: 65.7% yield of $CD34^+$ cells and mean: 88.5% and median: 95.9% relative purity (N=166) (Clin Lab. 2016 Jul. 1; 62 (7): 1243-1248 (PMID: 28164638)). "High stringency" refers to a process with the goal of substantial enrichment of a relatively rare cell type, CD34+, which usually comprises between 0.2-2% of the cell product in a mobilized leukopheresis or bone marrow collection. High-stringency enrichment of CD34+ cells from a mobilized leukopheresis or bone marrow collection targets final CD34+ percentages that have increased from 0.2-2% to >80%. To accomplish this, following initial application of a biological sample to a capture matrix, repeated buffer exchanges, termed herein "washes," are carried out with the goal of removing cells weakly or non-specifically bound to the capture matrix. Generally, cells are removed from the capture matrix and reapplied for every wash cycle. Removal and reapplication can be accomplished manually by pipetting from tubes or automated using a pump and tubing system. For example, using Quad Technologies MagCloudz® coupled with Dynabeads® magnetic cell separation system, cell-magnetic particle complexes are separated in tubes on a magnetic stand and washes are done manually. Using the Miltenyi Biotec CliniMACS® System, a pre-set automated program applies the cell-magnetic particle complexes to a magnetic column in a tubing set and washes/reapplications are done using a valve pump system. In certain embodiments, selection under high stringency conditions may be performed on various instruments, including without limitation the Miltenyi Biotec MACSQuant Tyto®, Quad Technologies MagCloudz®, GE Sepax® Cell Separation System, Terumo Elutra® Cell Separation System, COBE Spectra® Cell Separator, SynGen LAB® or WASH® Systems, Fresenius-Kabi Lovo®, Miltenyi Biotec CliniMACS® System or CliniMACS Prodigy® System. Selection may be performed in a laboratory or at point-of-care. Detailed methods for preparation and enrichment of cells and cell populations, including exemplary methods for selection of CD34+ cells under high stringency conditions, are described, e.g., in Int'l Patent Pub. No. WO 2016/118780. Illustrative selection method useful for high-stringency selection are provided by U.S. Pat. No. 8,727,132. Further illustrative selection methods are provided in International Patent Application No. PCT/US2019/027083, particularly Example 1.

In a high-stringency enrichment protocol, a biological sample comprising CD34+ cells is labeled with a CD34 labelling reagent, e.g. directly-conjugated immunomagnetic beads. The biological sample may be suspended in any suitable fluid, such as, without limitation, phosphate buffered saline (PBS) with, optionally, ethylenediaminetetraacetic acid (EDTA) at a buffer pH and isotonicity compatible with cell viability. In some cases, the fluid used also contain human serum albumin at a suitable concentration, such as about 2.5%. Using a magnetic activated cell sorting (MACS) technology, the biological sample, after having been labeled, is applied to a column, the column containing magnetically susceptible or ferromagnetic material. Using the MACS system, the magnetically susceptible or ferromagnetic material of the column retains the target cells without affecting the ability of non-target cells to flow through and exit the column. Such magnetically susceptible or ferromagnetic materials include iron, steel, cobalt nickel, and other ferromagnetic rare earth metals of alloys thereof. It will be appreciated by those skilled in the art that such materials may be readily magnetized and demagnetized. In some embodiments, the biological sample is recirculated over the magnetically susceptible or ferromagnetic material one or more times. Following column loading, bound cells are washed, eluted and/or re-loaded onto the column at slow speed to increase purity of the enriched fraction. Suitable wash buffers include PBS with (optionally) EDTA and (optionally) human serum albumin. Any component of the labeled biological sample which is removed during the wash steps is collected in the waste or "non-target" bag. After suitable wash steps, high-stringency enriched cells are eluted into the target cell bag.

In a low-stringency enrichment protocol, a biological sample comprising CD34+ cells is labeled with a CD34 labelling reagent, e.g. directly-conjugated immunomagnetic beads. Using a magnetic activated cell sorting (MACS) technology, the biological sample, after having been labeled, is applied a column containing magnetically susceptible or ferromagnetic material at a lower flow rate than under high-stringency enrichment. As with high-stringency enrichment, the magnetically susceptible or ferromagnetic material retains the target cells without affecting the ability of non-target cells to flow through and exit the column. In some embodiments, the biological sample is recirculated over the magnetically susceptible or ferromagnetic material one or more times. Following column loading, for low-stringency enrichment, bound cells are washed at lower stringency. Bound cells are then eluted into a collection bag.

In an exemplary embodiment, low-stringency enrichment is performed by modifying the standard operating procedure of the MACS system so that a "depletion-mode" software program intended to achieve high-stringency depletion (i.e. removal of target cells) instead results in low-stringency enrichment. Operation of a MACS system in depletion mode causes target cells in the biological sample to be bound to the magnetically susceptible or ferromagnetic material in the column using slow column loading and lower stringency wash steps than operation in enrichment mode. Non-target cells are flushed by the MACS system into the wash or so-called "target" bag. The depletion-mode program then switches the output valve to direct fluid into the so-called "non-target" bag and then demagnetizes the column. Continued application of fluid over the demagnetized column results in elution of a CD34+ enriched cell population, which has been enriched under low-stringency conditions, into the so-called "non-target" bag, which using this method collects the target cells.

Those of skill in the art will recognize that this low-stringency enrichment method can be performed on various instruments, including without limitation the Miltenyi Biotec MACSQuant Tyto®, Quad Technologies MagCloudz®, GE Sepax® Cell Separation System, Terumo Elutra® Cell Separation System, COBE Spectra® Cell Separator, SynGen LAB® or WASH® Systems, Fresenius-Kabi Lovo®, Miltenyi Biotec CliniMACS® System or CliniMACS Prodigy® System. Those of skill in the art will be able, without undue experimentation, to re-program the software of such a MACs system such that the output valve directs the flow-through of the initial binding step to the waste or "non-target" bag (rather than the target bag) and directs the eluted low-stringency CD34-enriched population to the "target" bag. In effect, low-stringency enrichment is then performed in separation mode without the usual wash steps of conventional MACs programs.

As used herein, "low stringency" or "low-stringency conditions" refers to a method of enriching for a cell population intended to result in enrichment of cells for cells expressing a particular biological marker, e.g. CD34, in a manner that preserves a higher yield of the enriched cell population than achieved by high stringency selection at the expense of enrichment of the cells expressing the biological marker compared to other cells in the biological sample, i.e., reduced enrichment. By definition, the fold enrichment under high-stringency conditions is greater than the fold enrichment under low-stringency conditions. The fold-enrichment of cells, e.g., CD34+ cells, in the high-stringency (CD34 or other marker)-enriched cell population is, in some cases, 2, 2.25, 2.5, 2.75, 3, 3.25, 3.5, 3.75, or 4-fold the fold-enrichment of CD34+ cells in the low-stringency (CD34 or other marker)-enriched cell population. In one embodiment, the fold-enrichment of cells, e.g. CD34+ cells, in the high-stringency (CD34 or other marker)-enriched cell population is 2 to 4-fold the fold-enrichment of CD34+ cells in the low-stringency (CD34 or other marker)-enriched cell population. In certain embodiments, selection under low stringency conditions may be performed on various instruments, including without limitation the Miltenyi Biotec MACSQuant Tyto®, Quad Technologies MagCloudz®, GE Sepax® Cell Separation System, Terumo Elutra® Cell Separation System, COBE Spectra® Cell Separator, SynGen LAB® or WASH® Systems, Fresenius-Kabi Lovo®, Miltenyi Biotec CliniMACS® System or CliniMACS Prodigy® System. Selection may be performed in a laboratory or at point-of-care. Exemplary methods for enrichment of cells under low stringency conditions are provided in in International Patent Application No. PCT/US2019/027083, which is incorporated by reference herein in its entirety.

Populations of cells enriched for CD34+ cells may be produced by selecting for CD34+ cells under high-stringency conditions and/or under low stringency conditions, thereby producing a high-stringency CD34-enriched cell population and/or a low-stringency CD34-enriched cell population. Selection methods for CD34+ cells may be positive selection, negative selection, or a combination thereof. In certain embodiments, the biological sample obtained from the subject is divided into two samples, where one sample is used to prepare the high-stringency CD34-enriched cell population, and the other sample is used to prepare the low-stringency CD34-enriched cell population. In other embodiments, the biological sample obtained from the subject is first subjected to a low-stringency CD34+ selection to prepare a low-stringency CD34-enriched cell population, and then a portion of the low-stringency CD34-enriched population is subjected to a high-stringency CD34+ selection to prepare a high-stringency CD34-enriched cell population. Selection may be applied sequentially, e.g., a selection for CD34-enriched cells under low stringency conditions may be applied first followed by selection from the resulting population of further CD34-enriched cells under high stringency conditions. In other cases, selection for CD34-enriched cells under high stringency conditions may be applied first followed by selection from the residual population of CD34-enriched cells under low stringency conditions. In some cases, the cell populations may be split such that a low stringency or a high stringency selection is applied to a fraction of the cells subjected to high stringency or low stringency selection previously. In some cases, one biological sample is split into two or more samples before selection of CD34-enriched cells under low or high stringency conditions.

In every case, high-stringency or low-stringency selection preceding or following mixing or splitting biological samples or enriched cell populations is contemplated, in all possible permutations. In certain embodiments, the method comprises preparing a high-stringency CD34-enriched cell population from a first biological sample obtained from the subject by selecting for $CD34^+$ cells under high stringency conditions; and preparing a low-stringency CD34-enriched cell population from a second biological sample obtained from the subject by selecting for $CD34^+$ cells under low stringency conditions.

Transduced Hematopoietic Cells

As described in further detail in the Examples, populations of hematopoietic cells transduced in the presence of a combination of transduction enhancers disclosed herein, e.g., protamine sulfate, PGE2 or a derivative thereof, and a poloxamer (e.g. LentiBOOST), exhibit superior properties as compared to hematopoietic cells transduced without the combination of transduction enhancers. In certain embodiments, the cells were also transduced in the presence of a recombinant fibronectin fragment, e.g., RetroNectin™. In particular embodiments, the transduced hematopoietic cells or population thereof has one or more of: increased VCN, increased VCN/cell, increased percent gene-modified CFU, and increased percent gene-modified CFC. In some embodiments, rescue of a gene of interest is enhanced. In particular embodiments for patients with LAD-1, percent (%) of $CD18^+$ cells is increased after transduction with a lentivirus vector comprising a CD18 gene compared to transduction without PGE2 or poloxamer, or compared to transduction with none or only one transduction enhancer.

In some embodiments of the disclosed methods, the percentage of hematopoietic cells genetically modified by the method is increased at least 1.5-fold, at least 2-fold, at least 2.5-fold, at least 3-fold, at least 3.5-fold, at least 4-fold, at least 5-fold, at least 6-fold, at least 7-fold, or at least 8-fold as compared to the percentage of hematopoietic cells genetically modified by the same viral vector without treatment of the cells with PGE2 or poloxamer, or compared to the percentage of hematopoietic cells genetically modified by the same viral vector with treatment of the cells with only one transduction enhancer.

In some embodiments, the method of transducing the hematopoietic cells with the retroviral (e.g., lentiviral) vector results in a population of hematopoietic cells having a VCN/cell of at least 1.0, at least 1.5, at least 2.0, or at least 2.5. In some embodiments, the method of treating a subject comprises providing to the subject a population of transduced hematopoietic cells having a VCN/cell of at least 1.0, at least 1.5, at least 2.0, or at least 2.5.

In some embodiments, the method of transducing the hematopoietic cells with the retroviral vector results in a population of hematopoietic cells having a transduction efficiency of at least 50%, at least 60%, at least 70%, at least 80%, at least 90% or at least 100%. In some embodiments, the method of treating a subject comprises providing to the subject a population of transduced hematopoietic cells having a transduction efficiency of at least 50%, at least 60%, at least 70%, at least 80%, at least 90% or at least 100%.

In some embodiments, the method of transducing the hematopoietic cells with the retroviral vector results in a population of hematopoietic cells having a percentage of transduced colony forming cells of at least 50%, at least 60%, at least 70%, at least 80%, at least 90% or at least 100%. In some embodiments, the method of treating a subject comprises providing to the subject a population of transduced hematopoietic cells having a percentage of transduced colony forming cells of at least 50%, at least 60%, at least 70%, at least 80%, at least 90% or at least 100%.

In some embodiments, the disclosure provides a population of hematopoietic cells transduced by a recombinant retroviral vector (e.g., a lentiviral vector) having a VCN/cell of at least 1.0, at least 1.5, at least 2.0, or at least 2.5. In some embodiments, the disclosure provides a population of hematopoietic cells transduced by a recombinant retroviral vector (e.g., a lentiviral vector) having a transduction efficiency of at least 50%, at least 60%, at least 70%, at least 80%, at least 90% or at least 100%.

In some embodiments, the disclosure provides a method of producing a population of hematopoietic cells comprising at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, or at least 95% genetically modified hematopoietic cells, comprising: contacting hematopoietic cells ex vivo with recombinant retroviral vector (optionally, a lentiviral vector) comprising a polynucleotide that comprises a gene of interest or encodes a polypeptide of interest, wherein the contacting occurs in the presence of a PGE2 or a derivative thereof, optionally human PGE2 or 16,16-dimethyl PGE2 (dmPGE2), and a poloxamer, optionally poloxamer 338 (LentiBOOST™). The cells may be contacted with the retroviral vector under conditions and for a time sufficient to permit transduction of the cells by the retroviral vector, e.g., in suitable culture media for at least one hour, at least two hours, at least four hours, at least eight hours, or at least twelve hours. In some embodiments, the cells are contacted with the retroviral vector and the transduction enhancers during the same or an overlapping period of time.

Advantageous, the methods of the disclosure result in reduced toxicity (greater survival) of the transduced cell population compared to transduction without the transductions enhancers. In some embodiments, the disclosure provides a method of producing a population of hematopoietic cells wherein toxicity, compared to transduction without the transduction enhancer, is reduced at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, or at least 35%.

Vectors and Expression Cassettes

Any convenient recombinant retroviral vector that finds use delivering polynucleotide sequences to mammalian cells is encompassed by the recombinant retroviral vectors of the present disclosure. For example, the vector may comprise single or double stranded nucleic acid, e.g., single stranded or double stranded DNA. For example, the recombinant retroviral vector may be DNA. The vector may comprise single-stranded or double-stranded RNA, including modified forms of RNA. In another example, the recombinant retroviral vector may be an RNA, e.g., an mRNA or modified mRNA.

In particular embodiments, the recombinant retroviral vector may be a viral vector derived from a virus, e.g., an adenovirus, an adeno-associated virus, a lentivirus (LV), a herpes virus, an alphavirus or a retrovirus, e.g., Moloney murine leukemia virus (M-MuL V), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) or Rous Sarcoma Virus (RSV). While embodiments encompassing the use of LV are described in greater detail below, it is expected that the ordinarily skilled artisan will appreciate that similar knowledge and skill in the art can be brought to bear on non-LV recombinant retroviral vectors as well. In some embodiments, the recombinant retroviral vector is a self-limiting LV.

In particular embodiments, the viral vector is a lentiviral vector. In some embodiments, it is a pseudotyped lentiviral vector, e.g., a VSVG-pseudotyped lentiviral vector.

In particular, certain methods disclosed herein relate to transducing two populations of stem cells or progenitor cells, e.g., hematopoietic stem cells (HSCs) or hematopoietic progenitor cells (also referred to herein as "hematopoietic progenitors") with a recombinant retroviral vector encoding and/or expressing a therapeutic polypeptide, e.g., FANCA, where one population is prepared by selection under high-stringency conditions and the other population is prepared by selection under low-stringency conditions. In one embodiment, the cell populations are enriched for CD34+ cells. In one embodiment, the HSCs or hematopoietic progenitors are from a subject with diminished or no protein activity from one or more FANCA encoded proteins. In one embodiment, the subject has FA-A. In one embodiment, the endogenous FANCA gene of the HSCs is deleted and/or mutated.

In one embodiment, transducing a cell with a recombinant retroviral vector results in the integration into the cell genome of an expression cassette comprising a promoter operably linked to a polynucleotide sequence encoding a therapeutic agent within the recombinant retroviral vector. In some embodiments, transducing a cell with a recombinant retroviral vector results in the expression of the therapeutic agent, e.g., a biologically active FANCA protein.

For example, a biologically active FANCA protein forms part of the FA core complex. In certain embodiments, a FANCA gene is delivered via a viral vector. In one embodiment, a FANCA gene is delivered via a lentiviral vector. In certain embodiments, the lentiviral vector is PGK-FANCA.WPRE*LV. It is contemplated that after transduction of bone marrow (BM) cells or stem cells or progenitor cells from FA-A patients with a FANCA lentiviral vector (LV), the therapeutic vector is integrated in the genome of the cells. Once integrated, the therapeutic protein (e.g., human FANCA protein) is expressed by the cells. Transduced FA cells are genetically corrected, and thus able to activate the FA pathway by the mono-ubiquitination of FANCD2 and FANCI. These proteins will be then able to migrate to areas of DNA damage, and in cooperation with other DNA repair proteins, will promote the repair of the DNA in these cells, as occurs in healthy cells.

As discussed herein, the subject methods and compositions find use in expressing a transgene, e.g., FANCA, in cells of an animal. For example, the subject compositions may be used in research, e.g., to determine the effect that the gene has on cell viability and/or function. As another example, the subject compositions may be used in medicine, e.g., to treat a disorder such as FA.

In some embodiments, the subject methods result in a therapeutic benefit, e.g., preventing the development of a disorder, halting the progression of a disorder, reversing the progression of a disorder, etc. For example, in one embodiment, the disorder is Fanconi Anemia (FA). In another embodiment, the disease or disorder is bone marrow failure (BMF). In one embodiment, the disorder is thrombocytopenia. In another embodiment, the disorder is leukopenia. In one embodiment, the disorder is pancytopenia. In one embodiment, the disorder is neutropenia. In another embodiment, the disorder is anemia. In some embodiments, the subject method comprises the step of detecting that a therapeutic benefit has been achieved. The ordinarily skilled artisan will appreciate that such measures of therapeutic efficacy will be applicable to the particular disease being modified, and will recognize the appropriate detection methods to use to measure therapeutic efficacy.

Accordingly, the present invention provides methods for treatment of FA, or one or more of the hematological manifestations of FA. In one embodiment, the hematological manifestation of FA is selected from one or more of bone marrow failure (BMF), thrombocytopenia, leukopenia, pancytopenia, neutropenia, and anemia. In a particular embodiment, the hematological manifestation is BMF, which appears in pediatric ages in most FA patients. In one embodiment, the hematological manifestation is thrombocytopenia. In another embodiment, the hematological manifestation is leukopenia. In one embodiment, the hematological manifestation is pancytopenia. In one embodiment, the hematological manifestation is neutropenia. In another embodiment, the hematological manifestation is anemia. In one embodiment, the hematological manifestation is a combination of two or more of BMF, thrombocytopenia, leukopenia, pancytopenia, neutropenia, and anemia.

Additional LV vectors that may be used according to the methods disclosed herein include but are not limited to those prepared using the transfer vectors disclosed below.

2. Use of Transduced Hematopoietic Cells

In some embodiments, hematopoietic cells transduced according to a method disclosed herein are used for gene therapy. In particular embodiments, the hematopoietic cells are transduced with a vector comprising a gene of interest. The transduced cells may be provided to a subject in need thereof, e.g., in order to treat a genetic disease or disorder in the subject. In particular embodiments, the gene of interest complements a defect in a gene associated with a monogenic genetic disease or disorder. In some embodiments, the subject comprises a mutation in the endogenous gene of interest. In some embodiments, the gene of interest provide to the subject is codon-optimized, e.g., to enhance expression in mammalian cells.

In an embodiment, the gene of interest is selected form the group consisting of Fanconi Anemia complementation group-A (FANCA), complementation group-C (FANCC), and complementation group-G (FANCG). In an embodiment, the gene of interest is Red-cell type Pyruvate Kinase (RPK). In an embodiment, the gene of interest is Integrin beta 2 (ITGB2), and/or the gene of interest encodes a protein encoded by any of the genes disclosed herein, or a functional fragment or variant thereof.

In an embodiment, the method prevents or ameliorates a monogenic genetic disease or disorder.

In an embodiment, the monogenetic disease or disorder is selected from the group consisting of Fanconi Anemia, Leukocyte Adhesion Deficiency Type I, Pyruvate Kinase Deficiency, and Infantile Malignant Osteoporosis.

Thus, the disclosure provides methods for treatment of monogenic genetic diseases or disorders, including, but not limited to Fanconi Anemia, Leukocyte Adhesion Deficiency Type I, Pyruvate Kinase Deficiency, and Infantile Malignant Osteopetrosis. In particular embodiments, the method comprises providing to a subject in need thereof hematopoietic cells transduced with a retroviral vector comprising a polynucleotide comprising a sequence encoding a therapeutic protein operably linked to a promoter sequence, wherein the cells were transduced according to a method disclosed herein, e.g., in the presence of two or more transduction enhancers disclosed herein.

In certain embodiments, the present invention includes a cell comprising a gene expression cassette, gene transfer cassette, or recombinant retroviral vector, e.g., any disclosed herein. In related embodiments, the cell was transduced with a recombinant retroviral vector comprising an expression cassette or has an expression cassette integrated into the cell's genome, wherein transduction was performed according to a method disclosed herein. In certain embodiments, the cell is a cell used to produce a recombinant retroviral vector, e.g., a packaging cell.

In certain embodiments, the cell is a cell to be delivered to a subject in order to provide to the subject the gene product encoded by the expression cassette. Thus, in certain embodiments, the cell is autologous to the subject to be treated or was obtained from the subject to be treated. In other embodiments, the cell is allogeneic to the subject to be treated or was obtained from a donor other than the subject to be treated. In particular embodiments, the cell is a mammalian cell, e.g., a human cell. In certain embodiments, the cell is a blood cell, an erythrocyte, a hematopoietic progenitor cell, a bone marrow cell, e.g., a lineage depleted bone marrow cell, a hematopoietic stem cell (e.g., CD34+) or a committed hematopoietic erythroid progenitor cell. In particular embodiments, the cell is a CD34+ cell obtained from a subject to be treated with the cell after it is transduced by a recombinant retroviral vector disclosed herein. In particular embodiment, the cell is a CD34+FA cell obtained from a subject diagnosed with FA. The present disclosure further includes populations of hematopoietic cells (optionally CD34-enriched cells) transduced according to a method disclosed herein.

In some embodiments, the methods disclosed herein result in a therapeutic benefit, e.g., preventing the development of a disorder, halting the progression of a disorder, reversing the progression of a disorder, etc. For example, in one embodiment, the disorder is BMF. In one embodiment, the disorder is thrombocytopenia. In another embodiment, the disorder is leukopenia. In one embodiment, the disorder is pancytopenia. In one embodiment, the disorder is neutropenia. In another embodiment, the disorder is anemia. In some embodiments, the subject method comprises the step of detecting that a therapeutic benefit has been achieved. The ordinarily skilled artisan will appreciate that such measures of therapeutic efficacy will be applicable to the particular disease being modified, and will recognize the appropriate detection methods to use to measure therapeutic efficacy.

Expression of the transgene using the subject transgene is expected to be robust. Accordingly, in some instances, the expression of the transgene, e.g. as detected by measuring levels of gene product, by measuring therapeutic efficacy, etc. may be observed two months or less after administration, e.g. 4, 3 or 2 weeks or less after administration, for example, 1 week after administration of the subject composition. Expression of the transgene is also expected to persist over time. Accordingly, in some instances, the expression of the transgene, e.g. as detected by measuring levels of gene product, by measuring therapeutic efficacy, etc., may be observed 2 months or more after administration of the subject composition, e.g., 4, 6, 8, or 10 months or more, in some instances 1 year or more, for example 2, 3, 4, or 5 years, in certain instances, more than 5 years.

In certain embodiments, the method comprises the step of detecting expression of the transgene in the cells or in the subject, wherein expression is enhanced relative to expression from a polynucleotide cassette not comprising the one or more improved elements of the present disclosure. Typically, expression will be enhanced 2-fold or more relative to the expression from a reference, i.e. a control polynucleotide cassette, e.g. as known in the art, for example 3-fold, 4-fold, or 5-fold or more, in some instances 10-fold, 20-fold or 50-fold or more, e.g. 100-fold, as evidenced by, e.g. earlier detection, higher levels of gene product, a stronger functional impact on the cells, etc.

In some embodiments, the dose of cells patients receive by infusion will be that which is obtained from the transduction process. In various preferred embodiments, at least about $1\times10^1$, $1\times10^2$, $1\times10^3$, $1\times10^4$, $1\times10^5$, $1\times10^6$, $1\times10^7$, $1\times10^8$, or more high-stringency CD34-enriched cells/KG of patient weight are infused into the patient. In various preferred embodiments, at least at least about $1\times10^1$, $1\times10^2$, $1\times10^3$, $1\times10^4$, $1\times10^5$, $1\times10^6$, $1\times10^7$, $1\times10^8$, or more low-stringency CD34-enriched cells/KG of patient weight are infused into the patient. In some embodiments, between $1\times10^6$ and $4\times10^6$ high-stringency CD34-enriched cells/Kg of patient weight are infused into the patient. In other embodiments, $3\times10^5$ and $4\times10^6$ high-stringency CD34-enriched cells/Kg of patient weight are infused into the patient. In some embodiments, between $1\times10^6$ and $4\times10^6$ high-stringency CD34-enriched cells/Kg of patient weight are infused into the patient. In other embodiments, $3\times10^5$ and $4\times10^6$ high-stringency CD34-enriched cells/Kg of patient weight are infused into the patient. In some embodiments, cells will be infused into the patient a single dose. In other embodiments, cells will be infused into the patient in multiple doses (e.g, the high-stringency and low-stringency CD34-enriched cell populations are administered sequentially once or multiple times). Transduced cells may be infused immediately after the transduction process is completed. In particular embodiments, the transduced cells are stored or frozen before use, whereas in certain embodiments, they are provided to the subject immediately or shortly after they are transduced, e.g., within one hour, two hours, four hours, or eight hours.

Once integrated, the therapeutic protein (e.g., human FANCA protein) is expressed by the cells. Transduced FA cells are genetically corrected, and thus able to activate the FA pathway by the mono-ubiquitination of FANCD2 and FANCI. These proteins migrate to areas of DNA damage, and in cooperation with other DNA repair proteins, promote the repair of the DNA in these cells, as occurs in healthy cells.

As described in further detail in the Examples, preclinical in vitro data with BM samples from human FA patients has already shown the efficacy of an FANCA LV to correct the phenotype of these cells.

In one embodiment, at least $1\times10^5$ to $4\times10^5$ $CD34^+$ corrected cells (e.g., FANCA transduced HSCs) per kilogram of patient weight are administered to restore hematopoiesis in a non-conditioned FA patient. In some embodiments, the transduced cells are infused or administered into the patient immediately after transduction. In other embodiments, the transduced cells are frozen prior to infusing or administering into the patient with or without conditioning.

The genetic correction of HSCs from FA patients, followed by the autologous transplantation of these cells (hematopoietic gene therapy), is a good alternative for FA patients, particularly those lacking an HLA-identical sibling for allogeneic transplantation. In one embodiment, hematopoietic gene therapy is the preferred treatment regimen for a patient lacking an HLA-identical sibling. In another embodiment, hematopoietic gene therapy is the preferred treatment regimen for a patient that has an HLA-identical sibling.

Fanconi Anemia (FA) is an autosomal recessive disease (except for complementation group FA-B, which is X-linked), and the median survival of patients is around 24 years (Butturini A, et al. (1994) *Blood* 84:1650-1655; Kutler D I, et al. (2003) *Blood* 101:1249-1256). At birth, the blood count of these patients is generally normal. Macrocytosis is often the first hematological abnormality detected in these patients. This usually evolves with thrombocytopenia, anemia and pancytopenia. Bone marrow failure (BMF) is usually observed in these patients after 5-10 years, with an average age of hematologic disease onset of 7 years. About 80% of patients with FA will develop evidence of BMF in the first decade of life. Based on epidemiological studies to date, if malignant episodes do not appear before aplasia, virtually all patients with FA will develop BMF by 40 years of age, this being the leading cause of mortality in these patients. Due to the complex clinical manifestations of FA, management of these patients is mainly focused on improving the following clinical manifestations: bone marrow failure (BMF), myeloid leukemia, and solid tumors.

In certain embodiments, the disclosure provides a method treating Fanconi Anemia (FA) in a subject in need thereof, comprising administering hematopoietic cells transduced with a recombinant retroviral vector comprising a polynucleotide encoding a Fanconi anemia complementation group (FANC) gene or a gene encoding functional variant or fragment thereof according to the methods disclosed herein. In some embodiments, the gene encodes FANCA.

Figure 15:
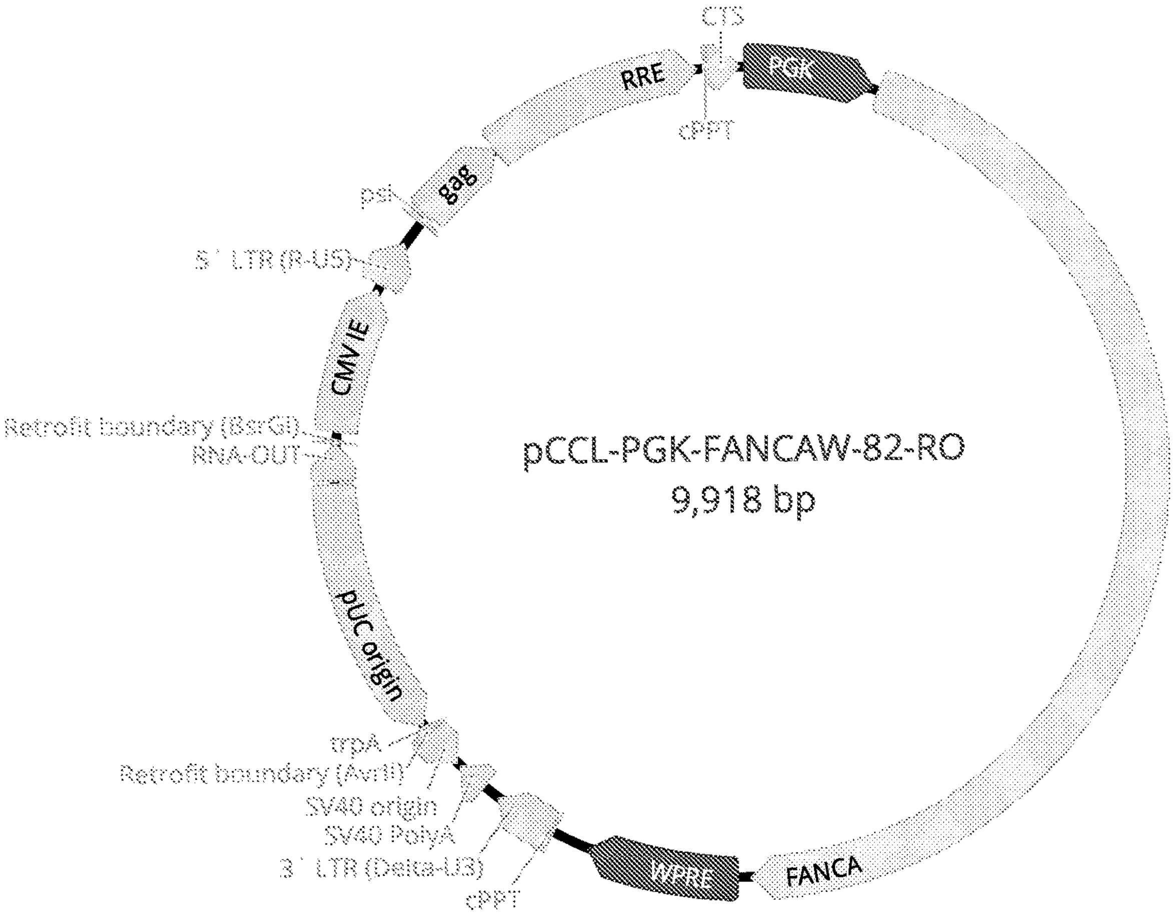
FIG. 15 is a schematic map of the pCCL-PGK-FANCAW-82-PRO transfer vector.

In some embodiments, methods disclosed herein are used to transduce hematopoietic cells with a lentiviral vector produced using the pCCL-PGK-FANCAW-82-PRO transfer vector, e.g., to generate a cell population for treatment of FA. pCCL-PGK-FANCAW-82-PRO is a lentiviral vector based on the pCCL transfer plasmid used in third-generation lentiviral vector systems. The pCCL transfer plasmid is a lentiviral vector containing chimeric CMV-HIV 5' LTRs and vector backbones in which the simian virus 40 polyadenylation and (enhancerless) origin of replication sequences are included downstream of the HIV 3' LTR, replacing most of the human sequence remaining from the HIV integration site. In pCCL, the enhancer and promoter (nucleotides −673 to −1 relative to the transcriptional start site; GenBank accession no. K03104) of CMV were joined to the R region of HIV-1. The vector uses a PGK promoter linked to the codon-optimized FANCA gene with upstream RRE and cPPT/CTS elements and a downstream wPRE element (FIG. 15).

The resulting lentiviral vector is used to transduce autologous CD34+ hematopoietic stem cells ("HSCs"), thus complementing the genetic defect. Briefly, HSC are mobilized by treating the patient with G-CSF, plerifaxor, or a combination of G-CSF and plerifaxor. The HSCs are then collected from peripheral blood of the patient by apheresis. CD34+ cells are enriched using magnetic capture (e.g. on the Miltenyi Biotec CliniMACs system) and the CD34+ enriched cells are transduced ex vivo according to methods disclosed herein with lentiviral particles previously generated by transient transfection of a third-generation lentiviral vector system that includes the pCCL-PGK-FANCAW-82-RO transfer plasmid. In certain embodiments, the cells are transduced in the presence of PGE2 and a poloxamer. In an embodiment, the poloxamer is poloxamer 338 (LentiBOOST™). Transduced HSCs are then transplanted into the patient by infusion and re-populate the HSC niche with FANCA-expressing cells.

The sequence of the FANCA expression cassette sequence in pCCL-PGK-FANCAW-82-PRO (5'-3') is as follows. The coding sequence for FANCA is indicated by bolded, capital letters. The WPRE sequence is underlined.

(SEQ ID NO: 1)

ggggttggggttgcgccttttccaaggcagccctgggtttgcgcagggacgcggctgctctgggcgtggttccgg gaaacgcagcggcgccgaccctgggtctcgcacattcttcacgtccgttcgcagcgtcacccggatcttcgccgc tacccttgtgggccccccggcgacgcttcctgctccgcccctaagtcgggaaggttccttgcggttcgcggcgtg -continued ccggacgtgacaaacggaagccgcacgtctcactagtaccctcgcagacggacagcgccagggagcaatggcagc gcgccgaccgcgatgggctgtggccaatagcggctgctcagcagggcgcgccgagagcagcggccgggaaggggc ggtgcgggaggcggggtgtggggcggtagtgtgggccctgttcctgcccgcgcggtgttccgcattctgcaagcc tccggagcgcacgtcggcagtcggctccctcgttgaccgaatcaccgacctctctccccaggggggatcccccggg ctgcaggaattcATGTCCGACTCGTGGGTCCCGAACTCCGCCTCGGGCCAGGACCCAGGGGGCCGCCGGAGGGCC

TGGGCCGAGCTGCTGGCGGGAAGGGTCAAGAGGGAAAAATATAATCCTGAAAGGGCACAGAAATTAAAGGAATCA

GCTGTGCGCCTCCTGCGAAGCCATCAGGACCTGAATGCCCTTTTGCTTGAGGTAGAAGGTCCACTGTGTAAAAAA

TTGTCTCTCAGCAAAGTGATTGACTGTGACAGTTCTGAGGCCTATGCTAATCATTCTAGTTCATTTATAGGCTCT

GCTTTGCAGGATCAAGCCTCAAGGCTGGGGGTTCCCGTGGGTATTCTCTCAGCCGGGATGGTTGCCTCTAGCGTG

GGACAGATCTGCACGGCTCCAGCGGAGACCAGTCACCCTGTGCTGCTGACTGTGGAGCAGAGAAAGAAGCTGTCT

TCCCTGTTAGAGTTTGCTCAGTATTTATTGGCACACAGTATGTTCTCCCGTCTTTCCTTCTGTCAAGAATTATGG

AAAATACAGAGTTCTTTGTTGCTTGAAGCGGTGTGGCATCTTCACGTACAAGGCATTGTGAGCCTGCAAGAGCTG

CTGGAAAGCCATCCCGACATGCATGCTGTGGGATCGTGGCTCTTCAGGAATCTGTGCTGCCTTTGTGAACAGATG

GAAGCATCCTGCCAGCATGCTGACGTCGCCAGGGCCATGCTTTCTGATTTTGTTCAAATGTTTGTTTTGAGGGGA

TTTCAGAAAAACTCAGATCTGAGAAGAACTGTGGAGCCTGAAAAAATGCCGCAGGTCACGGTTGATGTACTGCAG

AGAATGCTGATTTTTGCACTTGACGCTTTGGCTGCTGGAGTACAGGAGGAGTCCTCCACTCACAAGATCGTGAGG

TGCTGGTTCGGAGTGTTCAGTGGACACACGCTTGGCAGTGTAATTTCCACAGATCCTCTGAAGAGGTTCTTCAGT

CATACCCTGACTCAGATACTCACTCACAGCCCTGTGCTGAAAGCATCTGATGCTGTTCAGATGCAGAGAGAGTGG

AGCTTTGCGCGGACACACCCTCTGCTCACCTCACTGTACCGCAGGCTCTTTGTGATGCTGAGTGCAGAGGAGTTG

GTTGGCCATTTGCAAGAAGTTCTGGAAACGCAGGAGGTTCACTGGCAGAGAGTGCTCTCCTTTGTGTCTGCCCTG

GTTGTCTGCTTTCCAGAAGCGCAGCAGCTGCTTGAAGACTGGGTGGCGCGTTTGATGGCCCAGGCATTCGAGAGC

TGCCAGCTGGACAGCATGGTCACTGCGTTCCTGGTTGTGCGCCAGGCAGCACTGGAGGGCCCCTCTGCGTTCCTG

TCATATGCAGACTGGTTCAAGGCCTCCTTTGGGAGCACACGAGGCTACCATGGCTGCAGCAAGAAGGCCCTGGTC

TTCCTGTTTACGTTCTTGTCAGAACTCGTGCCTTTTGAGTCTCCCCGGTACCTGCAGGTGCACATTCTCCACCCA

CCCCTGGTTCCCAGCAAGTACCGCTCCCTCCTCACAGACTACATCTCATTGGCCAAGACACGGCTGGCCGACCTC

AAGGTTTCTATAGAAAACATGGGACTCTACGAGGATTTGTCATCAGCTGGGGACATTACTGAGCCCCACAGCCAA

GCTCTTCAGGATGTTGAAAAGGCCATCATGGTGTTTGAGCATACGGGGAACATCCCAGTCACCGTCATGGAGGCC

AGCATATTCAGGAGGCCTTACTACGTGTCCCACTTCCTCCCCGCCCTGCTCACACCTCGAGTGCTCCCCAAAGTC

CCTGACTCCCGTGTGGCGTTTATAGAGTCTCTGAAGAGAGCAGATAAAATCCCCCCATCTCTGTACTCCACCTAC

TGCCAGGCCTGCTCTGCTGCTGAAGAGAAGCCAGAAGATGCAGCCCTGGGAGTGAGGGCAGAACCCAACTCTGCT

GAGGAGCCCCTGGGACAGCTCACAGCTGCACTGGGAGAGCTGAGAGCCTCCATGACAGACCCCAGCCAGCGTGAT

GTTATATCGGCACAGGTGGCAGTGATTTCTGAAAGACTGAGGGCTGTCCTGGGCCACAATGAGGATGACAGCAGC

GTTGAGATATCAAAGATTCAGCTCAGCATCAACACGCCGAGACTGGAGCCACGGGAACACATTGCTGTGGACCTC

CTGCTGACGTCTTTCTGTCAGAACCTGATGGCTGCCTCCAGTGTCGCTCCCCCGGAGAGGCAGGGTCCCTGGGCT

GCCCTCTTCGTGAGGACCATGTGTGGACGTGTGCTCCCTGCAGTGCTCACCCGGCTCTGCCAGCTGCTCCGTCAC

CAGGGCCCGAGCCTGAGTGCCCCACATGTGCTGGGGTTGGCTGCCCTGGCCGTGCACCTGGGTGAGTCCAGGTCT

GCGCTCCCAGAGGTGGATGTGGGTCCTCCTGCACCTGGTGCTGGCCTTCCTGTCCCTGCGCTCTTTGACAGCCTC

CTGACCTGTAGGACGAGGGATTCCTTGTTCTTCTGCCTGAAATTTTGTACAGCAGCAATTTCTTACTCTCTCTGC

AAGTTTTCTTCCCAGTCACGAGATACTTTGTGCAGCTGCTTATCTCCAGGCCTTATTAAAAAGTTTCAGTTCCTC

ATGTTCAGATTGTTCTCAGAGGCCCGACAGCCTCTTTCTGAGGAGGACGTAGCCAGCCTTTCCTGGAGACCCTTG

CACCTTCCTTCTGCAGACTGGCAGAGAGCTGCCCTCTCTCTCTGGACACACAGAACCTTCCGAGAGGTGTTGXAA

-continued

AGAGGAAGATGTTCACTTAACTTACCAAGACTGGTTACACCTGGAGCTGGAAATTCAACCTGAAGCTGATGCTCT

TTCAGATACTGAACGGCAGGACTTCCACCAGTGGGCGATCCATGAGCACTTTCTCCCTGAGTCCTCGGCTTCAGG

GGGCTGTGACGGAGACCTGCAGGCTGCGTGTACCATTCTTGTCAACGCACTGATGGATTTCCACCAAAGCTCAAG

GAGTTATGACCACTCAGAAAATTCTGATTTGGTCTTTGGTGGCCGCACAGGAAATGAGGATATTATTTCCAGATT

GCAGGAGATGGTAGCTGACCTGGAGCTGCAGCAAGACCTCATAGTGCCTCTCGGCCACACCCCTTCCCAGGAGCA

CTTCCTCTTTGAGATTTTCCGCAGACGGCTCCAGGCTCTGACAAGCGGGTGGAGCGTGGCTGCCAGCCTTCAGAG

ACAGAGGGAGCTGCTAATGTACAAACGGATCCTCCTCCGCCTGCCTTCGTCTGTCCTCTGCGGCAGCAGCTTCCA

GGCAGAACAGCCCATCACTGCCAGATGCGAGCAGTTCTTCCACTTGGTCAACTCTGAGATGAGAAACTTCTGCTC

CCACGGAGGTGCCCTGACACAGGACATCACTGCCCACTTCTTCAGGGGCCTCCTGAACGCCTGTCTGCGGAGCAG

AGACCCCTCCCTGATGGTCGACTTCATACTGGCCAAGTGCCAGACGAAATGCCCCTTAATTTTGACCTCTGCTCT

GGTGTGGTGGCCGAGCCTGGAGCCTGTGCTGCTCTGCCGGTGGAGGAGACACTGCCAGAGCCCGCTGCCCCGGGA

ACTGCAGAAGCTACAAGAAGGCCGGCAGTTTGCCAGCGATTTCCTCTCCCCTGAGGCTGCCTCCCCAGCACCCAA

CCCGGACTGGCTCTCAGCTGCTGCACTGCACTTTGCGATTCAACAAGTCAGGGAAGAAAACATCAGGAAGCAGCT

AAAGAAGCTGGACTGCGAGAGAGAGGAGCTATTGGTTTTCCTTTTCTTCTTCTCCTTGATGGGCCTGCTGTCGTC

ACATCTGACCTCAAATAGCACCACAGACCTGCCAAAGGCTTTCCACGTTTGTGCAGCAATCCTCGAGTGTTTAGA

GAAGAGGAAGATATCCTGGCTGGCACTCTTTCAGTTGACAGAGAGTGACCTCAGGCTGGGGCGGCTCCTCCTCCG

TGTGGCCCCGGATCAGCACACCAGGCTGCTGCCTTTCGCTTTTTACAGTCTTCTCTCCTACTTCCATGAAGACGC

GGCCATCAGGGAAGAGGCCTTCCTGCATGTTGCTGTGGACATGTACTTGAAGCTGGTCCAGCTCTTCGTGGCTGG

GGATACAAGCACAGTTTCACCTCCAGCTGGCAGGAGCCTGGAGCTCAAGGGTCAGGGCAACCCCGTGGAACTGAT

AACAAAAGCTCGTCTTTTTCTGCTGCAGTTAATACCTCGGTGCCCGAAAAAGAGCTTCTCACACGTGGCAGAGCT

GCTGGCTGATCGTGGGGACTGCGACCCAGAGGTGAGCGCCGCCCTCCAGAGCAGACAGCAGGCTGCCCCTGACGC

TGACCTGTCCCAGGAGCCTCATCTCTTCTGATGAgaattcgatatcaagcttatcgataccgtcgaatcccccgg gctgcaggaattcgagcatcttaccgccatttattcccatatttgttctgtttttcttgatttgggtatacattt aaatgttaataaaacaaaatggtggggcaatcatttacatttttagggatatgtaattactagttcaggtgtatt gccacaagacaaacatgttaagaaactttcccgttatttacgctctgttcctgttaatcaacctctggattacaa aatttgtgaaagattgactgatattcttaactatgttgctccttttacgctgtgtggatatgctgctttaatgcc tctgtatcatgctattgcttcccgtacggctttcgttttctcctccttgtataaatcctggttgctgtctcttta tgaggagttgtggcccgttgtccgtcaacgtggcgtggtgtgctctgtgtttgctgacgcaacccccactggctg gggcattgccaccacctgtcaactcctttctgggactttcgctttccccctcccgatcgccacggcagaactcat cgccgcctgccttgcccgctgctggacaggggctaggttgctgggcactgataattccgtggtgttgtcggggaa gggcc.

The FANCA protein sequence encoded by this polypeptide is provided as SEQ ID NO: 2. Vectors for expression of FANCA useful in the present invention include, without limitation, those disclosed in International Patent Application Publication No. WO 2018/049273, the disclosure of which is incorporated herein in its entirety.

Leukocyte adhesion deficiency-1 (LAD-1), is a rare autosomal recessive disease caused by mutations in the ITGB2 gene, which encodes CD18, a protein present in several cell surface receptor complexes found on white blood cells, including lymphocyte function-associated antigen 1 (LFA-1), complement receptor 3 (CR-3), and complement receptor 4 (CR-4). The deficiency of LFA-1 causes neutrophils to be unable to adhere to and migrate out of blood vessels, so their counts can be high. It also impairs immune cell interaction, immune recognition, and cell-killing lymphocyte functions.

In certain embodiments, the disclosure provides a method treating Leukocyte Adhesion Deficiency Type I (LAD-1) in a subject in need thereof, comprising administering hematopoietic cells transduced with a recombinant retroviral vector comprising a polynucleotide encoding a ITGB2 gene or a gene encoding functional variant or fragment thereof according to the methods disclosed herein.

Figure 16:
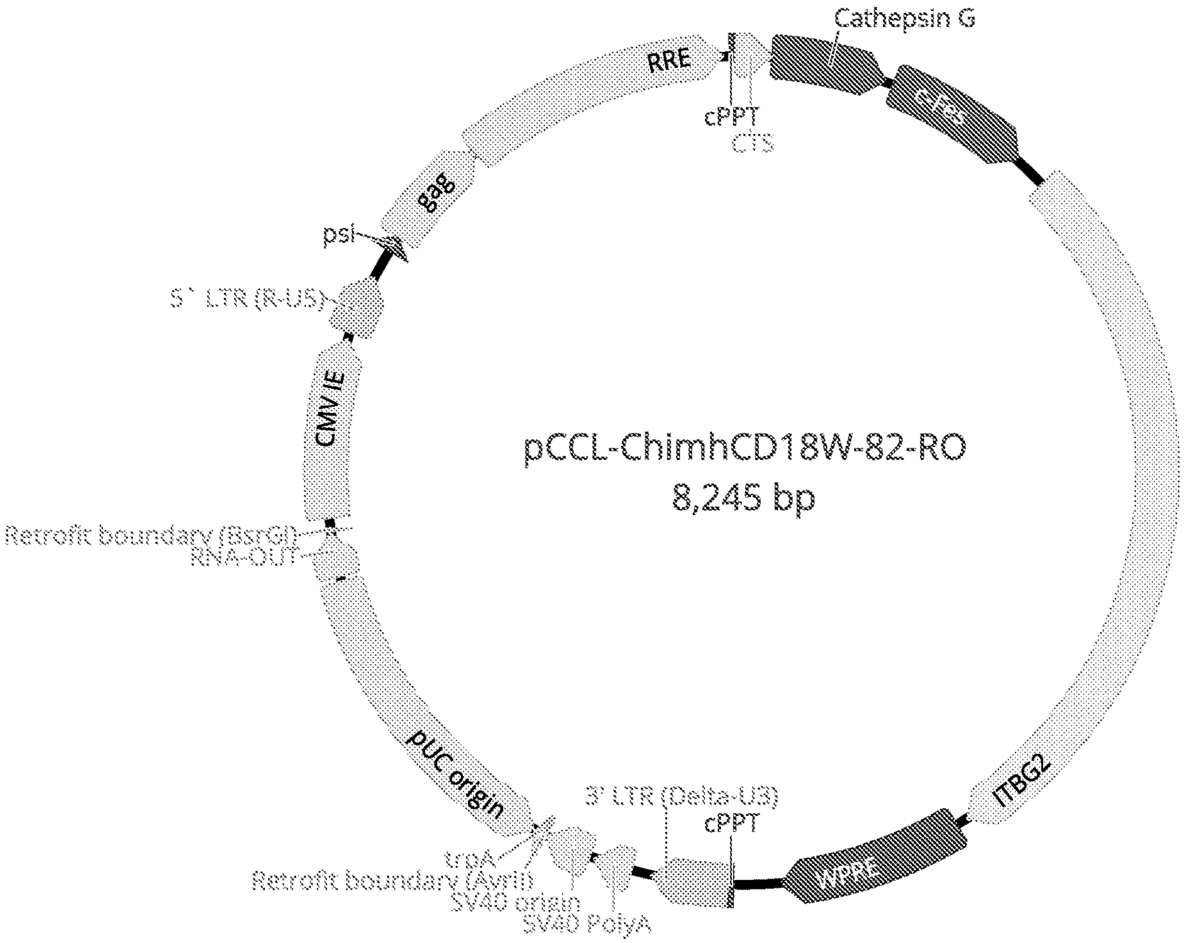
FIG. 16 is a schematic map of the pCCL-ChimhCD18W-82-RO transfer vector.

In some embodiments, methods disclosed herein are used to transduce hematopoietic cells with a lentiviral vector produced using the pCCL-ChimhCD18W-82-RO transfer vector, e.g., to generate a cell population for treatment of LAD-1. pCCL-ChimhCD18W-82-RO is a lentiviral transfer vector based on the pCCL transfer plasmid used in third-generation lentiviral vector systems. The pCCL transfer plasmid is a lentiviral vector containing chimeric CMV-HIV 5' LTRs and vector backbones in which the simian virus 40 polyadenylation and (enhancerless) origin of replication sequences are included downstream of the HIV 3' LTR, replacing most of the human sequence remaining from the HIV integration site. In pCCL, the enhancer and promoter (nucleotides −673 to −1 relative to the transcriptional start site; GenBank accession no. K03104) of CMV were joined to the R region of HIV-1. The vector uses a Chim promoter linked to the codon-optimized ITGB2 gene with upstream RRE and cPPT/CTS elements and a downstream wPRE element (FIG. 16). The Chim promoter is a fusion of the c-Fes promoter and the CTSG minimal 5'-flanking regions (where the TATA box of the CTSG promoter is mutated in order to limit transcriptional initiation to the c-Fes minimal promoter only).

Lentiviral particles are generated by transient transfection of a third-generation lentiviral vector system that includes the LAD-1 Transfer Plasmid. The lentiviral particles are used to transduce autologous CD34+ hematopoietic stem cells (HSCs), thus complementing the genetic defect. Briefly, HSC are mobilized by treating the patient with G-CSF, plerifaxor, or a combination of G-CSF and plerifaxor. The HSCs are then collected from peripheral blood of the patient by apheresis. CD34+ cells are enriched using magnetic capture (e.g., on the Miltenyi Biotec CliniMACs system), and the CD34+ enriched cells are transduced ex vivo with the lentiviral particles. The transduction process incorporates the use of transductions enhancers, notably polyoxamers (Rocket has licensed LentiBOOST from Sirion Biotech GmbH for both clinical and commercial use) and PGE2 (commercially available from LGM Pharma). The transduced HSCs are then transplanted into the patient by infusion where they repopulate the HSC niche with LAD-1-expressing cells.

The resulting lentiviral vector is used to transduce autologous CD34+ hematopoietic stem cells ("HSCs"), complementing the genetic defect. Briefly, HSC are mobilized by treating the patient with G-CSF, plerifaxor, or a combination of G-CSF and plerifaxor. The HSCs are then collected from peripheral blood of the patient by apheresis. CD34+ cells maybe enriched using magnetic capture (e.g. on the Miltenyi Biotec CliniMACs system) and the CD34+ enriched cells are transduced ex vivo according to methods disclosed herein with lentiviral particles previously generated by transient transfection of a third-generation lentiviral vector system that includes the pCCL-ChimhCD18W-82-RO transfer plasmid. In certain embodiments, the cells are transduced in the presence of PGE2 and a poloxamer. In an embodiment, the poloxamer is poloxamer 338 (LentiBOOST™). Transduced HSCs are then transplanted into the patient by infusion and re-populate the HSC niche with ITGB2-expressing cells.

The sequence of the ITGB2 expression cassette sequence in pCCL-ChimhCD18W-82-RO (5'-3') is as follows. The coding sequence for ITGB, also known as CD18, is indicated by bolded, capital letters. The WPRE sequence is underlined.

(SEQ ID NO: 3)

cgcgtctgccagctttcttgctttgctggagtattctggaatttgatgggttgagggttctggacacaatgccc caagccccttccttgttgtgctgggttcctatttctgctctcggcactgacttagcagctgctcaagagctcac catgttggcttggattacacggtctcacccacatctccggcagtttgtgggcaaacttcctgagcagccttggg tgatgaaacctttcatggtagcaggagaatgggactgtgaattctcaatcccctgtccccaccccttccttcct ctctcagggccttgctgtctaggaggagggagcacagcagcaactgactgggcagcctttcaggaaaggctagc ccgggctcgatcgagaagcttgataattccgtgaggtggggagggctgggaccagggttccctctttctcttct gcggtggccctggcctggtgctaggactgcgcgcctcccctcagtacccgcggacaccctgggcttccctgggc ccagcatctgcctggggcctcgccctgggctcccccctcctgacccccaccttgcgccccttcccggtgttcccg gggcgctgccgggccctggggcctgcggggcgcgggcggctcttggctgggccattctttcccggccccctcct cccttccgtttccgtggccgtgcggccggctagaggctgcggcccagcgcggagcagggggggctggcaggcgtc ggggcggtcgggccggtcccgcccgccccttcccctccacaggcccgccccggggcctgggccaactgaaaccg cgggaggaggaagcgcggaatcaggaactggccggggtccgcaccgggcctgagtcggtccgaggccgtcccag gagcagctgcccgaagggcgaattgggggatcccccgggctaatgccaactttgtacaaaaaagcaggctccac cATGCTGGGCCTGCGCCCCCCACTTCTCGCCCTGGTGGGGCTGCTCTCCCTCGGGTGCGTCCTCTCTCAGGAGT

GCACGAAGTTCAAGGTCAGCAGCTGCCGGGAATGCATCGAGTCGGGGCCCGGCTGCACCTGGTGCCAGAAGCTG

AACTTCACAGGGCCGGGGGATCCTGACTCCATTCGCTGCGACACCCGGCCACAGCTGCTCATGAGGGGCTGTGC

GGCTGACGACATCATGGACCCCACAAGCCTCGCTGAAACCCAGGAAGACCACAATGGGGGCCAGAAGCAGCTGT

CCCCACAAAAAGTGACGCTTTACCTGCGACCAGGCCAGGCAGCAGCGTTCAACGTGACCTTCCGGCGGGCCAAG

GGCTACCCCATCGACCTGTACTATCTGATGGACCTCTCCTACTCCATGCTTGATGACCTCAGGAATGTCAAGAA

GCTAGGTGGCGACCTGCTCCGGGCCCTCAACGAGATCACCGAGTCCGGCCGCATTGGCTTCGGGTCCTTCGTGG

ACAAGACCGTGCTGCCGTTCGTGAACACGCACCCTGATAAGCTGCGAAACCCATGCCCCAACAAGGAGAAAGAG

-continued

TGCCAGCCCCCGTTTGCCTTCAGGCACGTGCTGAAGCTGACCAACAACTCCAACCAGTTTCAGACCGAGGTCGG

GAAGCAGCTGATTTCCGGAAACCTGGATGCACCCGAGGGTGGGCTGGACGCCATGATGCAGGTCGCCGCCTGCC

CGGAGGAAATCGGCTGGCGCAACGTCACGCGGCTGCTGGTGTTTGCCACTGATGACGGCTTCCATTTCGCGGGC

GACGGGAAGCTGGGCGCCATCCTGACCCCCAACGACGGCCGCTGTCACCTGGAGGACAACTTGTACAAGAGGAG

CAACGAATTCGACTACCCATCGGTGGGCCAGCTGGCGCACAAGCTGGCTGAAAACAACATCCAGCCCATCTTCG

CGGTGACCAGTAGGATGGTGAAGACCTACGAGAAACTCACCGAGATCATCCCCAAGTCAGCCGTGGGGGAGCTG

TCTGAGGACTCCAGCAATGTGGTCCATCTCATTAAGAATGCTTACAATAAACTCTCCTCCAGGGTATTCCTGGA

TCACAACGCCCTCCCCGACACCCTGAAAGTCACCTACGACTCCTTCTGCAGCAATGGAGTGACGCACAGGAACC

AGCCCAGAGGTGACTGTGATGGCGTGCAGATCAATGTCCCGATCACCTTCCAGGTGAAGGTCACGGCCACAGAG

TGCATCCAGGAGCAGTCGTTTGTCATCCGGGCGCTGGGCTTCACGGACATAGTGACCGTGCAGGTCCTTCCCCA

GTGTGAGTGCCGGTGCCGGGACCAGAGCAGAGACCGCAGCCTCTGCCATGGCAAGGGCTTCTTGGAGTGCGGCA

TCTGCAGGTGTGACACTGGCTACATTGGGAAAAACTGTGAGTGCCAGACACAGGGCCGGAGCAGCCAGGAGCTG

GAAGGAAGCTGCCGGAAGGACAACAACTCCATCATCTGCTCAGGGCTGGGGGACTGTGTCTGCGGGCAGTGCCT

GTGCCACACCAGCGACGTCCCCGGCAAGCTGATATACGGGCAGTACTGCGAGTGTGACACCATCAACTGTGAGC

GCTACAACGGCCAGGTCTGCGGCGGCCCGGGGAGGGGGCTCTGCTTCTGCGGGAAGTGCCGCTGCCACCCGGGC

TTTGAGGGCTCAGCGTGCCAGTGCGAGAGGACCACTGAGGGCTGCCTGAACCCGCGGCGTGTTGAGTGTAGTGG

TCGTGGCCGGTGCCGCTGCAACGTATGCGAGTGCCATTCAGGCTACCAGCTGCCTCTGTGCCAGGAGTGCCCCG

GCTGCCCCTCACCCTGTGGCAAGTACATCTCCTGCGCCGAGTGCCTGAAGTTCGAAAAGGGCCCCTTTGGGAAG

AACTGCAGCGCGGCGTGTCCGGGCCTGCAGCTGTCGAACAACCCCGTGAAGGGCAGGACCTGCAAGGAGAGGGA

CTCAGAGGGCTGCTGGGTGGCCTACACGCTGGAGCAGCAGGACGGGATGGACCGCTACCTCATCTATGTGGATG

AGAGCCGAGAGTGTGTGGCAGGCCCCAACATCGCCGCCATCGTCGGGGGCACCGTGGCAGGCATCGTGCTGATC

GGCATTCTCCTGCTGGTCATCTGGAAGGCTCTGATCCACCTGAGCGACCTCCGGGAGTACAGGCGCTTTGAGAA

GGAGAAGCTCAAGTCCCAGTGGAACAATGATAATCCCCTTTTCAAGAGCGCCACCACGACGGTCATGAACCCCA

AGTTTGCTGAGAGTTAGgacccagctttcttgtacaaagttggcattaggaattcgagcatcttaccgccattt attcccatatttgttctgtttttcttgatttgggtatacatttaaatgttaataaaacaaaatggtggggcaat catttacatttttagggatatgtaattactagttcaggtgtattgccacaagacaaacatgttaagaaactttc ccgttatttacgctctgttcctgttaatcaacctctggattacaaaatttgtgaaagattgactgatattctta actatgttgctccttttacgctgtgtggatatgctgctttaatgcctctgtatcatgctattgcttcccgtacg gctttcgttttctcctccttgtataaatcctggttgctgtctctttatgaggagttgtggcccgttgtccgtca acgtggcgtggtgtgctctgtgtttgctgacgcaacccccactggctggggcattgccaccacctgtcaactcc tttctgggactttcgctttccccctcccgatcgccacggcagaactcatcgccgcctgccttgcccgctgctgg acaggggctaggttgctgggcactgataattccgtggtgttgtcggggaaggcc.

The human ITGB2 protein sequence is provided as SEQ ID NO: 4.

Pyruvate kinase deficiency (PKD) is a monogenic metabolic disease caused by mutations in the PKLR gene that impair energetic balance in erythrocytes, thus causing hemolytic anemia in a very variable range, and which can be fatal during the neonatal period.

In certain embodiments, the disclosure provides a method treating Pyruvate Kinase Deficiency in a subject in need thereof, comprising administering hematopoietic cells transduced with a recombinant retroviral vector comprising a polynucleotide encoding a R-type pyruvate kinase gene or a gene encoding functional variant or fragment thereof according to the methods disclosed herein.

Figure 17:
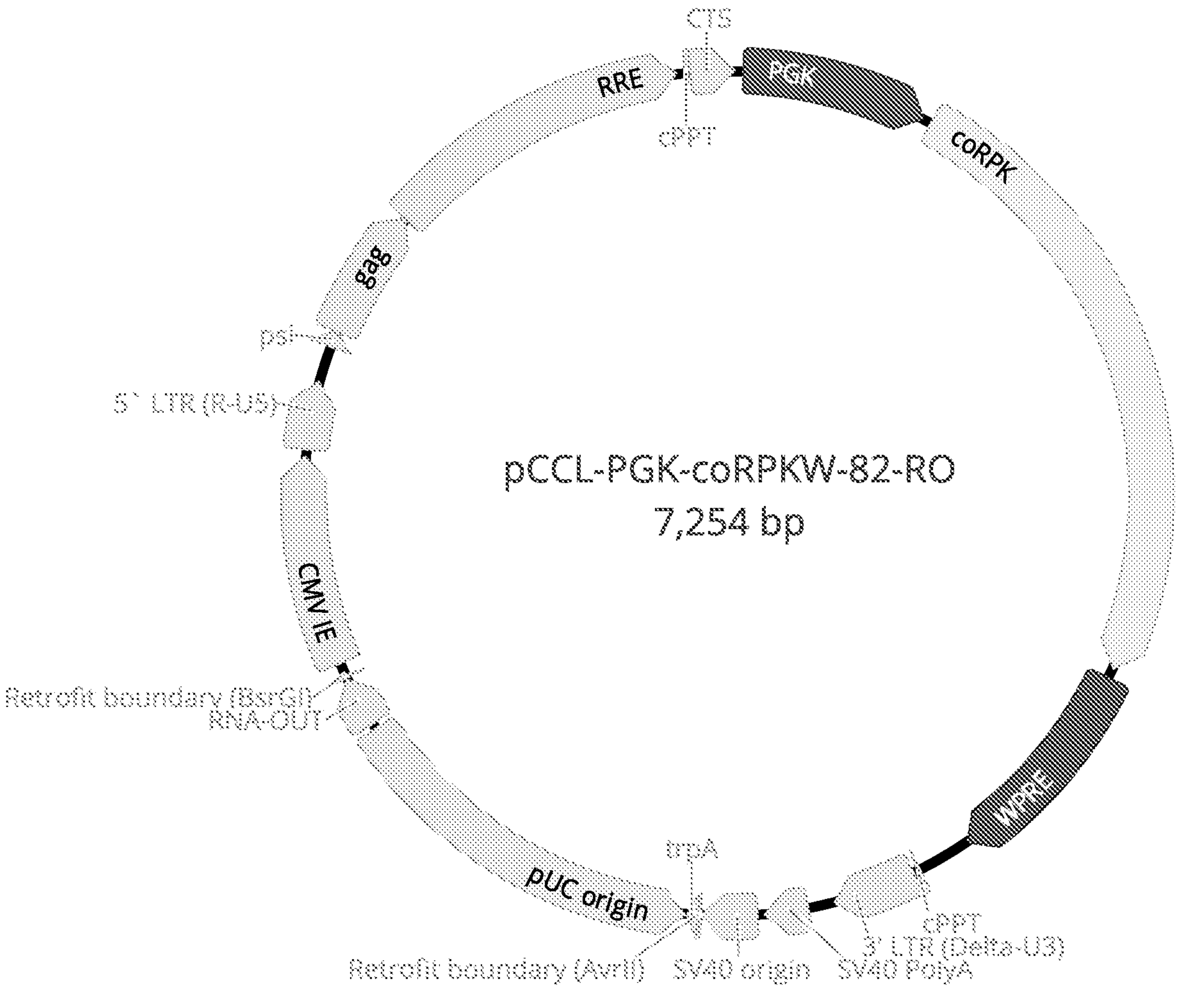
FIG. 17 is a schematic map of the pCCL-PGK-coRPKW-82-RO transfer vector.

In some embodiments, methods disclosed herein are used to transduce hematopoietic cells with a lentiviral vector produced using the pCCL-PGK-coRPKW-82-RO transfer vector, e.g., to generate a cell population for treatment of IMO. pCCL-PGK-coRPKW-82-RO ((PKD plasmid) is based on the pCCL transfer plasmid used in third-generation lentiviral vector systems. The pCCL transfer plasmid is a lentiviral vector containing chimeric CMV-HIV 5' LTRs and vector backbones in which the simian virus 40 polyadenylation and (enhancerless) origin of replication sequences are included downstream of the HIV 3' LTR, replacing most of the human sequence remaining from the HIV integration site. In pCCL, the enhancer and promoter (nucleotides−673 to −1 relative to the transcriptional start site; GenBank accession no. K03104) of CMV were joined to the R region of HIV-1. The PKD plasmid includes a PGK promoter linked to a codon-optimized PKLR gene with upstream RRE and cPPT/CTS elements and a downstream wPRE element (FIG. 1). Lentiviral vector particles are generated by transient transfection of a third-generation lentiviral vector system that includes the PKD plasmid (FIG. 17).

The lentiviral vector particles may then used to transduce autologous CD34+ hematopoietic stem cells ("HSCs"), thus complementing the genetic defect. Briefly, HSC are mobilized by treating the patient with G-CSF, plerifaxor, or a combination of G-CSF and plerifaxor. The HSCs are then collected from peripheral blood of the patient by apheresis. CD34+ cells may be enriched using magnetic capture (e.g. on the Miltenyi Biotec CliniMACs system), and the CD34+ enriched cells are transduced ex vivo with the lentiviral vector particles according to methods disclosed herein. In certain embodiments, the cells are transduced in the presence of PGE2 and a poloxamer. In an embodiment, the poloxamer is poloxamer 338 (LentiBOOST™). Transduced HSCs are then transplanted into the patient by infusion and re-populate the HSC niche with PKLR-expressing cells.

The sequence of the PKLR expression cassette sequence in pCCL-PGK-coRPKW-82-RO (5'-3') is as follows. The coding sequence for PKLR is indicated by bolded, capital letters. The PGK promoter is italicized and the WPRE sequence is underlined.

(SEQ ID NO: 5)

*ggggttggggttgcgccttttccaaggcagccctgggtttgcgcagggacgcggctgctctgggcgtggttccgg*

*gaaacgcagcggcgccgaccctgggtctcgcacattcttcacgtccgttcgcagcgtcacccggatcttcgccgc*

*tacccttgtgggccccccggcgacgcttcctgctccgcccctaagtcgggaaggttccttgcggttcgcggcgtg*

*ccggacgtgacaaacggaagccgcacgtctcactagtaccctcgcagacggacagcgccagggagcaatggcagc*

*gcgccgaccgcgatgggctgtggccaatagcggctgctcagcagggcgcgccgagagcagcggccgggaaggggc*

*ggtgcgggaggcggggtgtggggcggtagtgtgggccctgttcctgcccgcgcggtgttccgcattctgcaagcc*

*tccggagcgcacgtcggcagtcggctccctcgttgaccgaatcaccgacctctctccccag*gggatccgtcgac accggtgccaccATGAGCATCCAGGAAAATATCAGCTCTCTGCAGCTGCGGTCCTGGGTGTCCAAGAGCCAGAGA

GACCTGGCCAAGAGCATCCTGATCGGAGCCCCTGGCGGACCAGCCGGATACCTGAGAAGGGCTAGCGTGGCCCAG

CTGACCCAGGAACTGGGCACCGCCTTTTTCCAGCAGCAGCAGCTGCCAGCCGCCATGGCCGACACCTTTCTGGAA

CACCTGTGCCTGCTGGACATCGACTCTGAGCCCGTGGCCGCCAGAAGCACCAGCATCATTGCCACCATCGGCCCT

GCCAGCAGAAGCGTGGAGCGGCTGAAAGAGATGATCAAGGCCGGCATGAATATCGCCCGGCTGAACTTCTCCCAC

GGCAGCCACGAGTACCACGCAGAGAGCATTGCCAACGTCCGGGAGGCCGTGGAGAGCTTTGCCGGCAGCCCCCTG

AGCTACAGACCCGTGGCCATTGCCCTGGACACCAAGGGCCCCGAGATCAGAACAGGAATTCTGCAGGGAGGGCCT

GAGAGCGAGGTGGAGCTGGTGAAGGGCAGCCAAGTGCTGGTGACCGTGGACCCCGCCTTCAGAACCAGAGGCAAC

GCCAACACAGTGTGGGTGGACTACCCCAACATCGTGCGGGTGGTGCCTGTGGGCGGCAGAATCTACATCGACGAC

GGCCTGATCAGCCTGGTGGTGCAGAAGATCGGACCTGAGGGCCTGGTGACCCAGGTCGAGAATGGCGGCGTGCTG

GGCAGCAGAAAGGGCGTGAATCTGCCAGGCGCCCAGGTGGACCTGCCTGGCCTGTCTGAGCAGGACGTGAGAGAC

CTGAGATTTGGCGTGGAGCACGGCGTGGACATCGTGTTCGCCAGCTTCGTGCGGAAGGCCTCTGATGTGGCCGCC

GTGAGAGCCGCTCTGGGCCCTGAAGGCCACGGCATCAAGATCATCAGCAAGATCGAGAACCACGAGGGCGTGAAG

CGGTTCGACGAGATCCTGGAAGTGTCCGACGGCATCATGGTGGCCAGAGGCGACCTGGGCATCGAGATCCCCGCC

GAGAAGGTGTTCCTGGCCCAGAAAATGATGATCGGACGGTGCAACCTGGCCGGCAAACCTGTGGTGTGCGCCACC

CAGATGCTGGAAAGCATGATCACCAAGCCCAGACCCACCAGAGCCGAGACAAGCGACGTGGCCAACGCCGTGCTG

GATGGCGCTGACTGCATCATGCTGTCCGGCGAGACAGCCAAGGGCAACTTCCCCGTGGAGGCCGTGAAGATGCAG

CACGCCATTGCCAGAGAAGCCGAGGCCGCCGTGTACCACCGGCAGCTGTTCGAGGAACTGCGGAGAGCCGCCCCT

CTGAGCAGAGATCCCACCGAAGTGACCGCCATCGGAGCCGTGGAAGCCGCCTTCAAGTGCTGCGCCGCTGCAATC

ATCGTGCTGACCACCACAGGCAGAAGCGCCCAGCTGCTGTCCAGATACAGACCCAGAGCCGCCGTGATCGCCGTG

ACAAGATCCGCCCAGGCCGCTAGACAGGTCCACCTGTGCAGAGGCGTGTTCCCCCTGCTGTACCGGGAGCCTCCC

GAGGCCATCTGGGCCGACGACGTGGACAGACGGGTGCAGTTCGGCATCGAGAGCGGCAAGCTGCGGGGCTTCCTG

AGAGTGGGCGACCTGGTGATCGTGGTGACAGGCTGGCGGCCTGGCAGCGGCTACACCAACATCATGAGGGTGCTG

TCCATCAGCTGAccgcggtctagaggatcccccgggctgcaggaattcgagcatcttaccgccatttattcccat

-continued atttgttctgtttttcttgatttgggtatacatttaaatgttaataaaacaaaatggtggggcaatcatttacat ttttagggatatgtaattactagttcaggtgtattgccacaagacaaacatgttaagaaactttcccgttattta cgctctgttcctgttaatcaacctctggattacaaaatttgtgaaagattgactgatattcttaactatgttgct ccttttacgctgtgtggatatgctgctttaatgcctctgtatcatgctattgcttcccgtacggctttcgttttc tcctccttgtataaatcctggttgctgtctctttatgaggagttgtggcccgttgtccgtcaacgtggcgtggtg tgctctgtgtttgctgacgcaacccccactggctggggcattgccaccacctgtcaactcctttctgggactttc gctttccccctcccgatcgccacggcagaactcatcgccgcctgccttgcccgctgctggacaggggctaggttg ctgggcactgataattccgtggtgttgtcggggaagggcc.

The PKLR protein sequence encoded by this polypeptide is provided as SEQ ID NO: 6. Further PKLR polynucleotide sequences useful in the present invention include SEQ ID NOs: 7-9. Vectors for expression of PKLR useful in the present invention include, without limitation, those disclosed in International Patent Application No. PCT/US2019/041465, the disclosure of which is incorporated herein in its entirety.

Infantile malignant osteopetrosis (IMO) is a rare, recessive disorder characterized by increased bone mass caused by dysfunctional osteoclasts. The disease is most often caused by mutations in the TCIRG1 gene encoding a subunit of the V-ATPase involved in the osteoclasts capacity to resorb bone. Richter et al. have shown that osteoclast function can be restored by lentiviral vector-mediated expression of TCIRG1, but the exact threshold for restoration of resorption as well as the cellular response to vector-mediated TCIRG1 expression is unknown.

In certain embodiments, the disclosure provides a method treating Infantile Malignant Osteoporosis in a subject in need thereof, comprising administering hematopoietic cells transduced with a recombinant retroviral vector comprising a polynucleotide encoding CLCN7, OSTM1, T cell immune regulator 1, ATPase H+ transporting V0 subunit a3 (TCIRG1), TNFSF11, PLEKHM1, or TNFRSF11A gene or a gene encoding functional variant or fragment thereof according to the methods disclosed herein.

Figure 18:
FIG. 18 is a schematic map of the pRRL.PPT.EFS.tcirg1h.wpre transfer vector.

In some embodiments, methods disclosed herein are used to transduce hematopoietic cells with a lentiviral vector produced using the pCCL.PPT.EFS.tcirg1h.wpre transfer vector, e.g., to generate a cell population for treatment of IMO. pCCL.PPT.EFS.tcirg1h.wpre is a lentiviral transfer vector based on the pCCL transfer plasmid used in third-generation lentiviral vector systems. The pCCL transfer plasmid is a lentiviral vector containing chimeric CMV-HIV 5' LTRs and vector backbones in which the simian virus 40 polyadenylation and (enhancerless) origin of replication sequences are included downstream of the HIV 3' LTR, replacing most of the human sequence remaining from the HIV integration site. In pCCL, the enhancer and promoter (nucleotides −673 to −1 relative to the transcriptional start site; GenBank accession no. K03104) of CMV were joined to the R region of HIV-1. The vector uses a EFS promoter (a short, intron-less form of the EF1alpha promoter) linked to a codon-optimized TCIRG1 gene with upstream RRE and cPPT/CTS elements and a downstream wPRE element (FIG. 18).

The resulting lentiviral vector is used to transduce autologous CD34+ hematopoietic stem cells ("HSCs"), thus complementing the genetic defect. In some embodiments, HSC are mobilized by treating the patient with G-CSF, plerifaxor, or a combination of G-CSF and plerifaxor. The HSCs are then collected from peripheral blood of the patient by apheresis. CD34+ cells may be enriched using magnetic capture (e.g. on the Miltenyi Biotec CliniMACs system) and the CD34+ enriched cells may be transduced ex vivo according to the methods disclosed herein with the lentiviral particles previously generated by transient transfection of a lentiviral vector system that includes the pCCLL.PPT.EFS.tcirg1h.wpre transfer plasmid. In certain embodiments, the cells are transduced in the presence of PGE2 and a poloxamer. In an embodiment, the poloxamer is poloxamer 338 (LentiBOOST™). Transduced HSCs are then transplanted into the patient by infusion and generate TCIRG1-expressing osteoclasts.

The sequence of the TCIRG1 expression cassette sequence in pCCL.PPT.EFS.tcirg1h.wpre (5'-3') is as follows. The coding sequence for TCIRG1, also known as CD18, is indicated by bolded, capital letters. The WPRE sequence is underlined.

(SEQ ID NO: 10)

ggctccggtgcccgtcagtgggcagagcgcacatcgcccacagtccccgagaagttggggggaggggtcggcaat tgaaccggtgcctagagaaggtggcgcggggtaaactgggaaagtgatgtcgtgtactggctccgcctttttccc gagggtgggggagaaccgtatataagtgcagtagtcgccgtgaacgttctttttcgcaacgggtttgccgccaga acacaggtgtcgtgacgcgggatccgccaccATGGGCTCCATGTTTCGGAGCGAGGAGGTGGCCCTGGTCCAGCT

CTTTCTGCCCACAGCGGCTGCCTACACCTGCGTGAGTCGGCTGGGCGAGCTGGGCCTCGTGGAGTTCAGAGACCT

CAACGCCTCGGTGAGCGCCTTCCAGAGACGCTTTGTGGTTGATGTTCGGCGCTGTGAGGAGCTGGAGAAGACCTT

CACCTTCCTGCAGGAGGAGGTGCGGCGGGCTGGGCTGGTCCTGCCCCCGCCAAAGGGGAGGCTGCCGGCACCCCC

ACCCCGGGACCTGCTGCGCATCCAGGAGGAGACGGAGCGCCTGGCCCAGGAGCTGCGGGATGTGCGGGGCAACCA

GCAGGCCCTGCGGGCCCAGCTGCACCAGCTGCAGCTCCACGCCGCCGTGCTACGCCAGGGCCATGAACCTCAGCT

-continued

GGCAGCCGCCCACACAGATGGGGCCTCAGAGAGGACGCCCCTGCTCCAGGCCCCCGGGGGGCCGCACCAGGACCT

GAGGGTCAACTTTGTGGCAGGTGCCGTGGAGCCCCACAAGGCCCCTGCCCTAGAGCGCCTGCTCTGGAGGGCCTG

CAGAGGCTTCCTCATTGCCAGCTTCAGGGAGCTGGAGCAGCCGCTGGAGCACCCCGTGACGGGCGAGCCAGCCAC

GTGGATGACCTTCCTCATCTCCTACTGGGGTGAGCAGATCGGACAGAAGATCCGCAAGATCACGGACTGCTTCCA

CTGCCACGTCTTCCCGTTTCTGCAGCAGGAGGAGGCCCGCCTCGGGGCCCTGCAGCAGCTGCAACAGCAGAGCCA

GGAGCTGCAGGAGGTCCTCGGGGAGACAGAGCGGTTCCTGAGCCAGGTGCTAGGCCGGGTGCTGCAGCTGCTGCC

GCCAGGGCAGGTGCAGGTCCACAAGATGAAGGCCGTGTACCTGGCCCTGAACCAGTGCAGCGTGAGCACCACGCA

CAAGTGCCTCATTGCCGAGGCCTGGTGCTCTGTGCGAGACCTGCCCGCCCTGCAGGAGGCCCTGCGGGACAGCTC

GATGGAGGAGGGAGTGAGTGCCGTGGCTCACCGCATCCCCTGCCGGGACATGCCCCCCACACTCATCCGCACCAA

CCGCTTCACGGCCAGCTTCCAGGGCATCGTGGATGCCTACGGCGTGGGCCGCTACCAGGAGGTCAACCCCGCTCC

CTACACCATCATCACCTTCCCCTTCCTGTTTGCTGTGATGTTCGGGGATGTGGGCCACGGGCTGCTCATGTTCCT

CTTCGCCCTGGCCATGGTCCTTGCGGAGAACCGACCGGCTGTGAAGGCCGCGCAGAACGAGATCTGGCAGACTTT

CTTCAGGGGCCGCTACCTGCTCCTGCTTATGGGCCTGTTCTCCATCTACACCGGCTTCATCTACAACGAGTGCTT

CAGTCGCGCCACCAGCATCTTCCCCTCGGGCTGGAGTGTGGCCGCCATGGCCAACCAGTCTGGCTGGAGTGATGC

ATTCCTGGCCCAGCACACGATGCTTACCCTGGACCCCAACGTCACCGGTGTCTTCCTGGGACCCTACCCCTTTGG

CATCGATCCTATTTGGAGCCTGGCTGCCAACCACTTGAGCTTCCTCAACTCCTTCAAGATGAAGATGTCCGTCAT

CCTGGGCGTCGTGCACATGGCCTTTGGGGTGGTCCTCGGAGTCTTCAACCACGTGCACTTTGGCCAGAGGCACCG

GCTGCTGCTGGAGACGCTGCCGGAGCTCACCTTCCTGCTGGGACTCTTCGGTTACCTCGTGTTCCTAGTCATCTA

CAAGTGGCTGTGTGTCTGGGCTGCCAGGGCCGCCTCGGCCCCCAGCATCCTCATCCACTTCATCAACATGTTCCT

CTTCTCCCACAGCCCCAGCAACAGGCTGCTCTACCCCCGGCAGGAGGTGGTCCAGGCCACGCTGGTGGTCCTGGC

CTTGGCCATGGTGCCCATCCTGCTGCTTGGCACACCCCTGCACCTGCTGCACCGCCACCGCCGCCGCCTGCGGAG

GAGGCCCGCTGACCGACAGGAGGAAAACAAGGCCGGGTTGCTGGACCTGCCTGACGCATCTGTGAATGGCTGGAG

CTCCGATGAGGAAAAGGCAGGGGGCCTGGATGATGAAGAGGAGGCCGAGCTCGTCCCCTCCGAGGTGCTCATGCA

CCAGGCCATCCACACCATCGAGTTCTGCCTGGGCTGCGTCTCCAACACCGCCTCCTACCTGCGCCTGTGGGCCCT

GAGCCTGGCCCACGCCCAGCTGTCCGAGGTTCTGTGGGCCATGGTGATGCGCATAGGCCTGGGCCTGGGCCGGGA

GGTGGGCGTGGCGGCTGTGGTGCTGGTCCCCATCTTTGCCGCCTTTGCCGTGATGACCGTGGCTATCCTGCTGGT

GATGGAGGGACTCTCAGCCTTCCTGCACGCCCTGCGGCTGCACTGGGTGGAATTCCAGAACAAGTTCTACTCAGG

CACGGGCTACAAGCTGAGTCCCTTCACCTTCGCTGCCACAGATGACTAGtaagtcgacggatcccccgggctgca ggaattcgagcatcttaccgccatttatacccatatttgttctgtttttcttgatttgggtatacatttaaatgt taataaaacaaaatggtggggcaatcatttacatttttagggatatgtaattactagttcaggtgtattgccaca agacaaacatgttaagaaactttcccgttatttacgctctgttcctgttaatcaacctctggattacaaaatttg tgaaagattgactgatattcttaactatgttgctccttttacgctgtgtggatatgctgctttaatgcctctgta tcatgctattgcttcccgtacggctttcgttttctcctccttgtataaatcctggttgctgtctctttatgagga gttgtggcccgttgtccgtcaacgtggcgtggtgtgctctgtgtttgctgacgcaacccccactggctggggcat tgccaccacctgtcaactcctttctgggactttcgctttccccctcccgatcgccacggcagaactcatcgccgc ctgccttgcccgctgctggacaggggctaggttgctgggcactgataattccgtggtgttgtcggggaagctgac gtcctttcg.

The TCIRG1 protein sequence encoded by this polypeptide is provided as SEQ ID NO: 11.

In some cases, the recombinant retroviral vector provides a transgene for, or repairs, a gene other than a gene associated with a disease or disorder. For example, without limitation, the recombinant retroviral vector may up or down regulate immune effector genes, may alter cell surface markers, may provide alternate MHC molecules or may encode immunoglobulin genes. It is particularly contemplated that in some cases the recombinant retroviral vector or vectors provide for use of allogenic or unmatched donor transplant, such as by altering immune markers (e.g., HLA or MHC genes) or causing expression of immune effector genes.

The coding sequence to be expressed in the cells can be any polynucleotide sequence, e.g. gene or cDNA that encodes a gene product, e.g., a polypeptide or RNA-based therapeutic (siRNA, antisense, ribozyme, shRNA, etc.). The coding sequence may be heterologous to the promoter sequence to which it is operably linked, i.e. not naturally operably associated with it. Alternatively, the coding sequence may be endogenous to the promoter sequence to which it is operably linked, i.e., is associated in nature with that promoter. The gene product may act intrinsically in the mammalian cell, or it may act extrinsically, e.g., it may be secreted. For example, when the transgene is a therapeutic gene, the coding sequence may be any gene that encodes a desired gene product or functional fragment or variant thereof that can be used as a therapeutic for treating a disease or disorder. In various embodiments, the transgene encodes human FANCA.

In some embodiments, the transgene coding sequence is modified, or "codon optimized" to enhance expression by replacing infrequently represented codons with more frequently represented codons. The coding sequence is the portion of the mRNA sequence that encodes the amino acids for translation. During translation, each of 61 trinucleotide codons are translated to one of 20 amino acids, leading to a degeneracy, or redundancy, in the genetic code. However, different cell types, and different animal species, utilize tRNAs (each bearing an anticodon) coding for the same amino acids at different frequencies. When a gene sequence contains codons that are infrequently represented by the corresponding tRNA, the ribosome translation machinery may slow, impeding efficient translation. Expression can be improved via "codon optimization" for a particular species, where the coding sequence is altered to encode the same protein sequence, but utilizing codons that are highly represented, and/or utilized by highly expressed human proteins (Cid-Arregui et al., 2003; J. Virol. 77:4928). In one aspect of the present invention, the coding sequence of the transgene is modified to replace codons infrequently expressed in mammal or in primates with codons frequently expressed in primates. For example, in some embodiments, the coding sequence encoded by the transgene encodes a polypeptide having at least 85% sequence identity to a polypeptide encoded by a sequence disclosed above or herein, for example at least 90% sequence identity, e.g. at least 95% sequence identity, at least 98% identity, at least 99% identity, wherein at least one codon of the coding sequence has a higher tRNA frequency in humans than the corresponding codon in the sequence disclosed above or herein.

In additional embodiments, the transgene coding sequence is modified to enhance expression by termination or removal of open reading frames (ORFs) that do not encode the desired transgene. An open reading frame (ORF) is the nucleic acid sequence that follows a start codon and does not contain a stop codon. ORFs may be in the forward or reverse orientation, and may be "in frame" or "out of frame" compared with the gene of interest. Such open reading frames have the potential to be expressed in an expression cassette alongside the gene of interest, and could lead to undesired adverse effects. In one aspect of the present invention, the coding sequence of the transgene has been modified to remove open reading frames by further altering codon usage. This may be done by eliminating start codons (ATG) and introducing stop codons (TAG, TAA, or TGA) in reverse orientation or out-of-frame ORFs, while preserving the amino acid sequence and maintaining highly utilized codons in the gene of interest (i.e., avoiding codons with frequency <20%). In the present disclosure, the transgene coding sequence may be optimized by either of codon optimization and removal of non-transgene ORFs or using both techniques. As will be apparent to one of ordinary skill in the art, it is preferable to remove or minimize non-transgene ORFs after codon optimization in order to remove ORFs introduced during codon optimization.

Additionally, as will be recognized by one of ordinary skill in the art, the expression cassettes and recombinant retroviral vectors may optionally contain other elements including, but not limited to restriction sites to facilitate cloning and regulatory elements for a particular recombinant retroviral vector.

In some aspects of the present invention, the subject polynucleotide cassettes are used to deliver a gene to cells, e.g. to determine the effect that the gene has on cell viability and/or function, to treat a cell disorder, etc. In various embodiments, delivery of a viral vector to cells by transduction may occur in vivo, ex vivo, or in vitro. Accordingly, in some aspects of the invention, the composition that provides for the expression of a transgene in mammalian cells is a recombinant retroviral vector, wherein the recombinant retroviral vector comprises a polynucleotide cassette, e.g., a gene transfer cassette, of the present disclosure.

Recombinant retroviral vectors encapsulating the polynucleotide cassettes of the present disclosure may be produced using standard methodology.

For example, in the case of LV virions, an LV expression vector according to the invention may be introduced into a producer cell, followed by introduction of an LV helper construct, where the helper construct includes LV coding regions capable of being expressed in the producer cell and which complement LV helper functions absent in the LV vector. This is followed by introduction of helper virus and/or additional vectors into the producer cell, wherein the helper virus and/or additional vectors provide accessory functions capable of supporting efficient LV production. The producer cells are then cultured to produce LV. These steps are carried out using standard methodology. In particular embodiments, the plasmids depicted in FIGS. 15-18 are used to produce the recombinant retroviral vectors.

Methods for Producing Viral Vectors

Recombinant retroviral vectors encapsulating the polynucleotide cassettes of the present disclosure may be produced using standard methodology.

For example, in the case of LV virions, an LV expression vector according to the invention may be introduced into a producer cell, followed by introduction of an LV helper construct, where the helper construct includes LV coding regions capable of being expressed in the producer cell and which complement LV helper functions absent in the LV vector. This is followed by introduction of helper virus and/or additional vectors into the producer cell, wherein the helper virus and/or additional vectors provide accessory functions capable of supporting efficient LV production. The producer cells are then cultured to produce LV. These steps are carried out using standard methodology. In particular embodiments, the plasmids depicted in FIGS. 15-18 are used to produce the recombinant retroviral vectors.

Any suitable method for producing viral vectors for delivery of the subject polynucleotide cassettes can be used, including but not limited to those described in the examples that follow. Any concentration of infective viral vector suitable to effectively transduce mammalian cells can be prepared for contacting mammalian cells in vitro or in vivo. For example, the viral particles may be formulated at a concentration of $10^8$ infectious units per ml or more, for example, $1\times10^8$ infectious units per mL; $5\times10^8$ infectious units per mL; $10^9$ infectious units per mL; $5\times10^9$ infectious units per mL, $10^{10}$ infectious units per mL, $5\times10^{10}$ infectious units per mL; $10^{11}$ infectious units per mL; $5\times10^{11}$ infectious units per mL; $10^{12}$ infectious units per mL; $5\times10^{12}$ infectious units per mL; $10^{13}$ infectious units per mL; $1.5\times10^{13}$ infectious units per mL; $3\times10^{13}$ infectious units per mL; $5\times10^{13}$ infectious units per mL; $7.5\times10^{13}$ infectious units per mL; $9\times10^{13}$ infectious units per mL; $1\times10^{14}$ infectious units per mL, $5\times10^{14}$ infectious units per mL or more, but typically not more than $1\times10^{15}$ infectious units per mL.

In preparing the subject LV recombinant retroviral vectors, any host cells for producing LV virions may be employed, including, for example, mammalian cells (e.g. HEK 293T cells). Host cells can also be packaging cells in which the LV gag/pol and Rev genes are stably maintained in the host cell or producer cells in which the LV vector genome is stably maintained and packaged. LV vectors are purified and formulated using standard techniques known in the art.

Pharmaceutical Compositions and Formulations

The present invention includes pharmaceutical compositions and formulations comprising cell populations as described herein and a pharmaceutically-acceptable carrier, diluent or excipient. The subject cell populations can be combined with pharmaceutically-acceptable carriers, diluents and reagents useful in preparing a formulation that is generally safe, non-toxic, and desirable, and includes excipients that are acceptable for primate use. Examples of such excipients, carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, dimethyl sulfoxide (DMSO), fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide. In particular embodiments, the formulations are sterile.

In some embodiments, the cell populations are manufactured in accordance with Current Good Manufacturing Practices. Manufactured in accordance with Current Good Manufacturing Practices means that the formulation prepared for administration is sufficiently safe to permit administration to a human subject under controlling regulations and government authorizations. Generally, the controlling regulations and authorizations will dictate that the formulation meet pre-approved acceptance criteria regarding identity, strength, quality and purity. Acceptance criteria include numerical limits, ranges, or other suitable measures of test results used to determine whether a formulation meets the Current Good Manufacturing Practices. A specification sets forth the analytical procedures that are used to test conformance with the acceptance criteria. Formulations can be assessed in batches. A batch is a specific quantity of a formulation tested to ensure compliance with acceptance criteria.

The formulations can be included in a container, pack, or dispenser, e.g. syringe, e.g. a prefilled syringe, together with instructions for administration.

Where necessary or beneficial, formulations can include a local anesthetic such as lidocaine to ease pain at a site of injection.

Therapeutically effective amounts of cells in formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$. Therapeutically effective amounts of cells within formulations can be less than $10^3$ cells, less than $10^4$ cells, less than $10^5$ cells, less than $10^6$ cells, less than $10^7$ cells, less than $10^8$ cells, less than $10^9$ cells, less than $10^{10}$ cells, less than $10^{11}$ cells, or less than $10^{12}$. Therapeutically effective amounts of cells within formulations can be between $10^3$ cells and $10^{12}$ cells, between $10^4$ cells and $10^{11}$ cells, between $10^5$ cells and $10^{10}$ cells, between $10^8$ cells and $10^{12}$ cells, between $10^9$ cells and $10^{12}$ cells, between $10^8$ cells and $10^{10}$ cells, or between $10^9$ cells and $10^{11}$ cells.

In formulations disclosed herein, cells are generally in a volume of a liter or less, 500 mL or less, 250 mL or less or 100 mL or less. Hence the density of administered cells is typically greater than $10^4$ cells/mL, $10^7$ cells/mL or $10^8$ cells/mL.

The formulations disclosed herein can be prepared for administration by, for example, injection, infusion, perfusion, or lavage. Therapeutically effective amounts to administer can include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$. In particular embodiments, a minimum dose is $2\times10^6$ cells/kg subject body weight. Therapeutically effective amounts to administer can include less than $10^3$ cells, less than $10^4$ cells, less than $10^5$ cells, less than $10^6$ cells, less than $10^7$ cells, less than $10^8$ cells, less than $10^9$ cells, less than $10^{10}$ cells, less than $10^{11}$ cells, or less than $10^{12}$. In particular embodiments, a maximum dose is $2\times10^{12}$ cells/kg subject body weight. Therapeutically effective amounts of cells to administer can be between $10^3$ cells and $10^{12}$ cells, between $10^4$ cells and $10^{11}$ cells, between $10^5$ cells and $10^{10}$ cells, between $10^8$ cells and $10^{12}$ cells, between $10^9$ cells and $10^{12}$ cells, between $10^8$ cells and $10^{10}$ cells, or between $10^9$ cells and $10^{11}$ cells.

In some embodiments, the pharmaceutical composition provided herein comprise a therapeutically effective amount of a cell population as disclosed herein in a mixture with a pharmaceutically acceptable carrier and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol 1 compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C. In an embodiment, the cell population is freshly prepared from an in vivo source. In an embodiment, the cell population is frozen for storage prior to formulation or after formulation into a pharmaceutical composition.

In some embodiments, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. The pH of the buffer in which the pharmaceutical composition comprising the tumor suppressor gene contained in the adenoviral vector delivery system, may be in the range of 6.5 to 7.75, preferably 7 to 7.5, and most preferably 7.2 to 7.4.

All publications mentioned herein are incorporated herein by reference to disclose and describe the methods and/or materials in connection with which the publications are cited. It is understood that the present disclosure supersedes any disclosure of an incorporated publication to the extent there is a contradiction.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Further, the dates of publication provided may be different from the actual publication dates which may need to be independently confirmed.

The disclosure is further described in the following Examples, which do not limit the scope of the disclosure described in the claims.

EXAMPLES

Example 1

Transduction of Hematopoietic Cells with Protamine Sulfate and PGE2

Transduction of hematopoietic cells with retroviral vectors for clinical application remains challenging. In particular, it is unclear from the literature which transduction enhancers or combinations thereof are likely to be most effective or the magnitude of the effect that can be achieved. This Example establishes that the combination of protamine sulfate and PGE2 increase transduction efficiency.

An illustrative protocol for transduction of hematopoietic cells with lentiviral vectors as performed in the examples that follow is provided in FIG. 1, although in various experiments described in the examples, the transduction media included no TE, a single TE, or various combinations of TEs. Pre-stimulation included culturing the cells on plates coated with 2 ug/cm$^2$ RetroNectin™ (RN). The transduction media included the contents of the Pre-stimulation media (X-VIVO™ 20 medium plus 100 ng/mL rhSCF, 100 ng/mL rhTPO, 100 ng/mL rh-FLT3-L, and 20 ng/ml IL-3) and 4 μg/mL protamine sulfate.

Figure 2A:
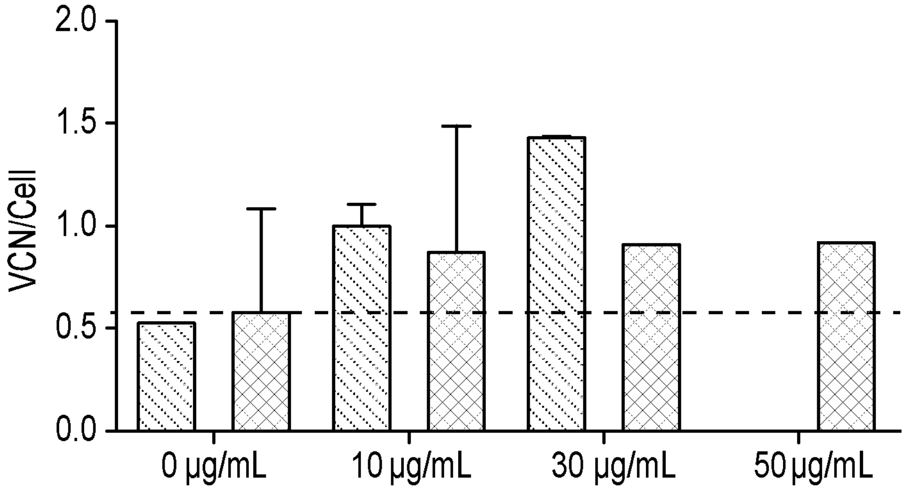
FIGS. 2A and 2B show results for VCN determination for cells in liquid culture transduced in the presence of PGE2. For FIG. 2A, at each concentration shown, the left bar shows results from cells transduced with $2.5\times10^7$ TU/mL and the right bar shows results from cells transduced with $5\times10^7$ TU/mL of lentiviral vector.

In one experiment, hematopoietic cells were transduced with a VSVG-pseudotyped LV expressing a GFP (green fluorescent protein) transgene reporter. Cells were transduced with either 2.5×10$^7$ TU/mL or 5×10$^7$ TU/mL of lentiviral vector in liquid culture in the presence of PGE2 in varying concentrations and assayed for VCN determination after 14 days in liquid culture (FIG. 2A). The results show that increasing concentrations of PGE2 (10 μg/mL, 30 μg/mL, or 50 μg/mL) increase transduction efficiency as measured by vector copy numbers/cell.

Figure 2B:
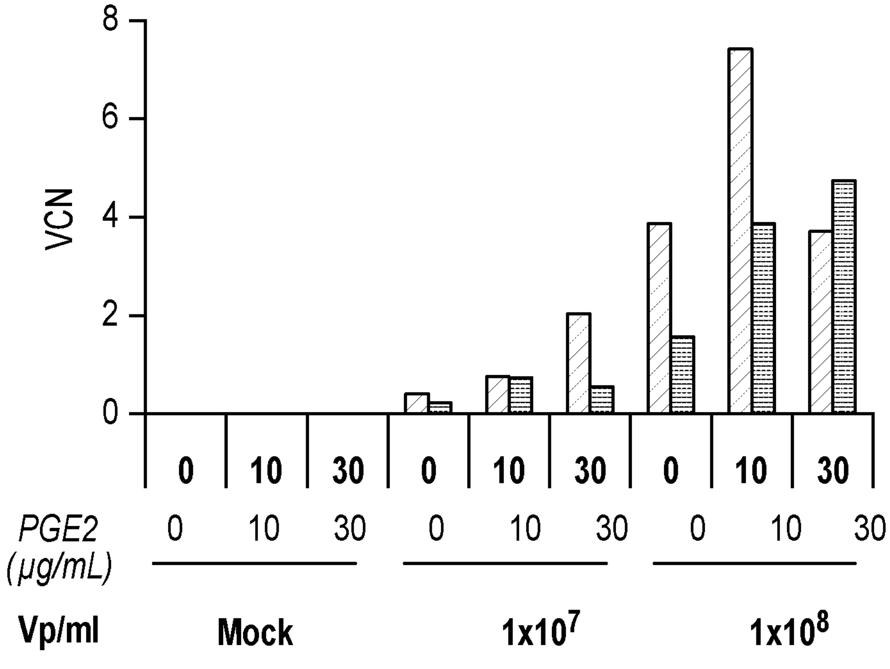
Figure 3A:
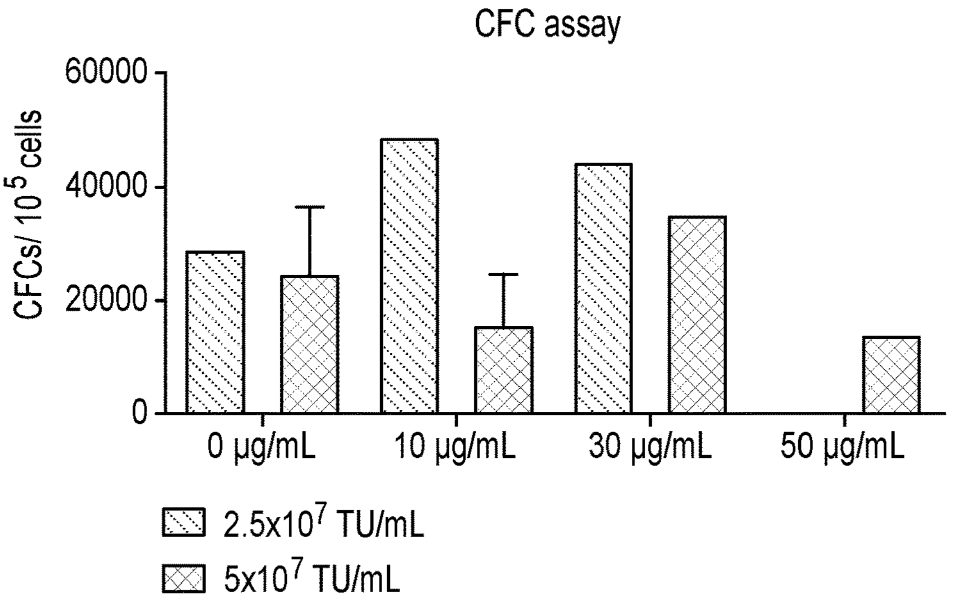
FIGS. 3A-3C show results for CFC assay (FIG. 3A), VCN determination (FIG. 3B), and percent (%) of transduction (FIG. 3C) in the CFC assay for cells transduced in the presence of PGE2.
Figure 3B:
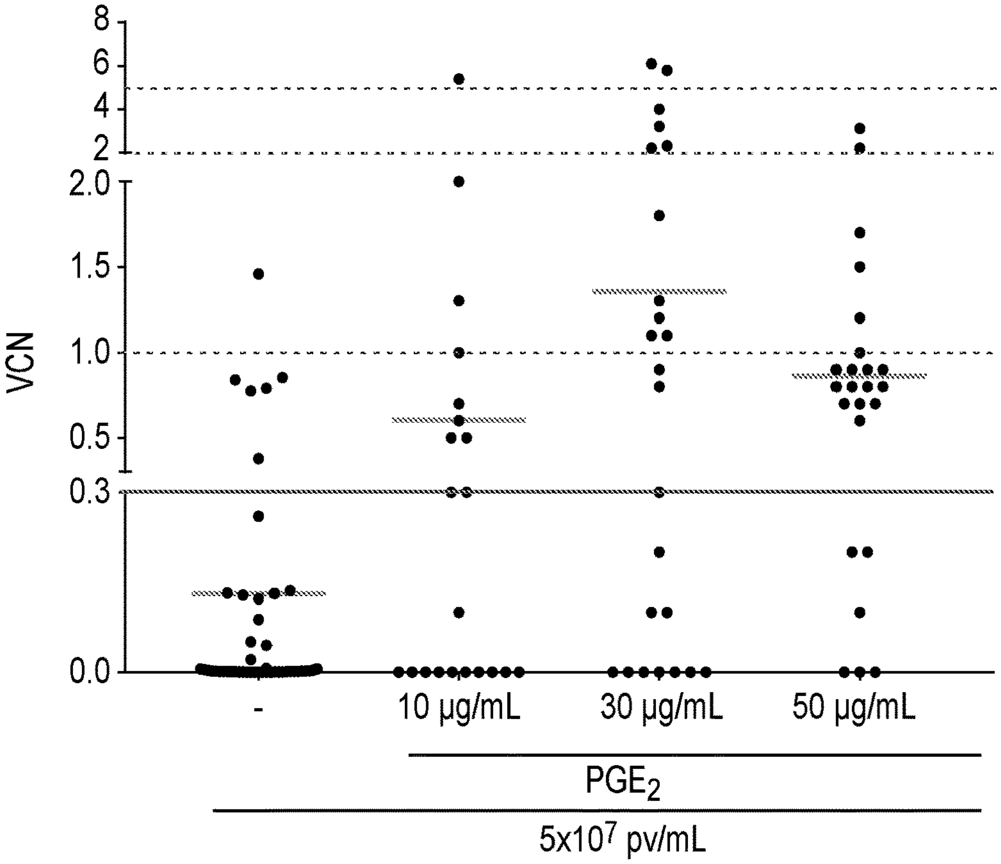
Figure 3C:
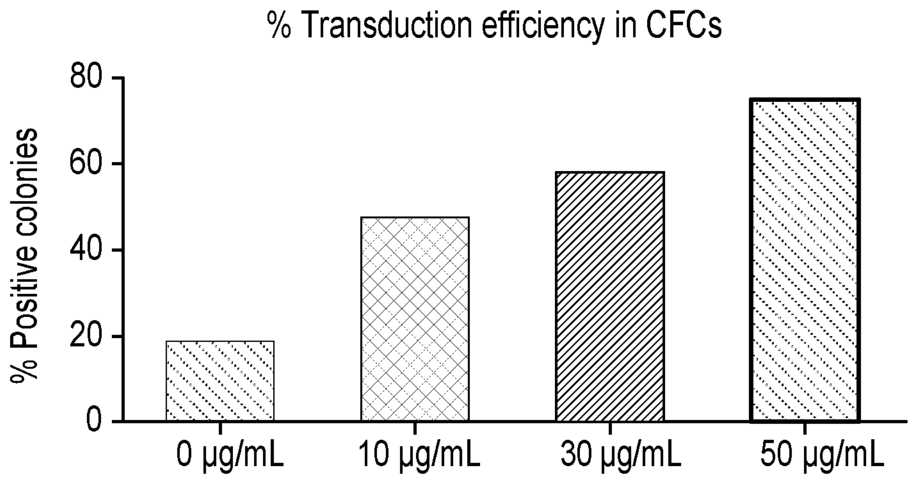

In another experiment, cells were transduced with either 1×10$^7$ TU/mL or 1×10$^8$ TU/mL of lentiviral vector in liquid culture in the presence of PGE2, and assayed for VCN determination after 14 days in liquid culture (FIG. 2B). At both vector concentrations, PGE2 increased transduction efficiency as determined by VCN/cell. A colony forming units (CFUs) assay was performed with transduced cells (FIG. 3A, CFCs=colony-forming cells), and VCN and percent (%) transduction were analyzed in single colonies (FIGS. 3B and 3C). Using the highest tested concentration of PGE2, up to about 75% of cells were transduced (FIG. 3C).

Example 2

Transduction of Hematopoietic Cells with Protamine Sulfate and Poloxamer F108

Figure 4:
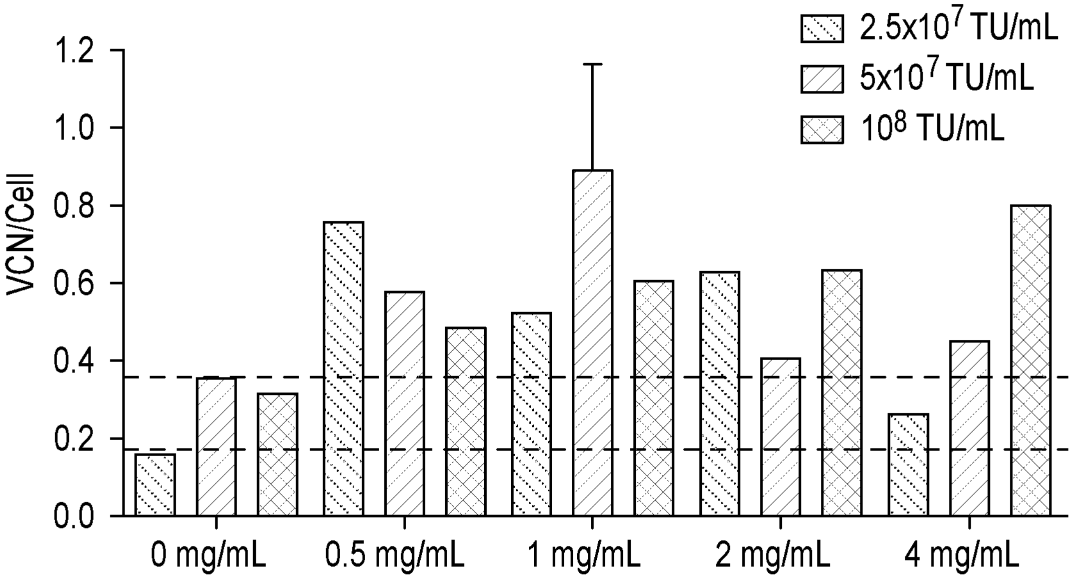
FIG. 4 shows results for VCN determination for cells in liquid culture transduced in the presence of LentiBOOST.
Figure 5A:
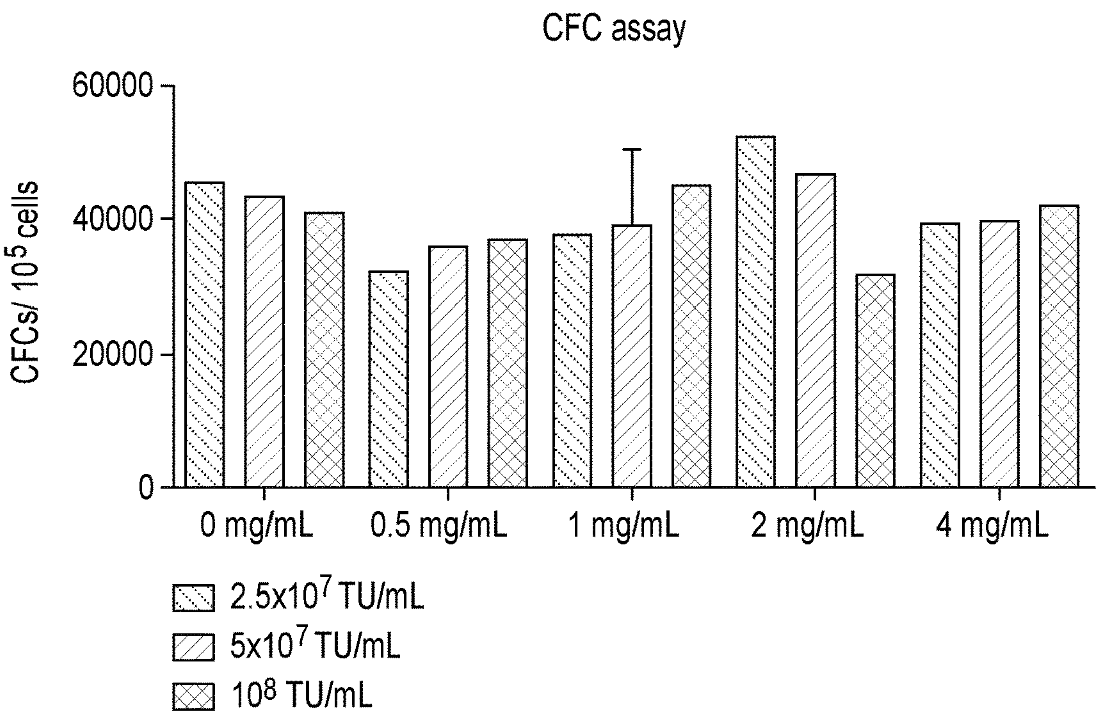
FIGS. 5A-5C show results for VCN determination and percent (%) transduction in the CFC assay for cells transduced using LentiBOOST.
Figure 5B:
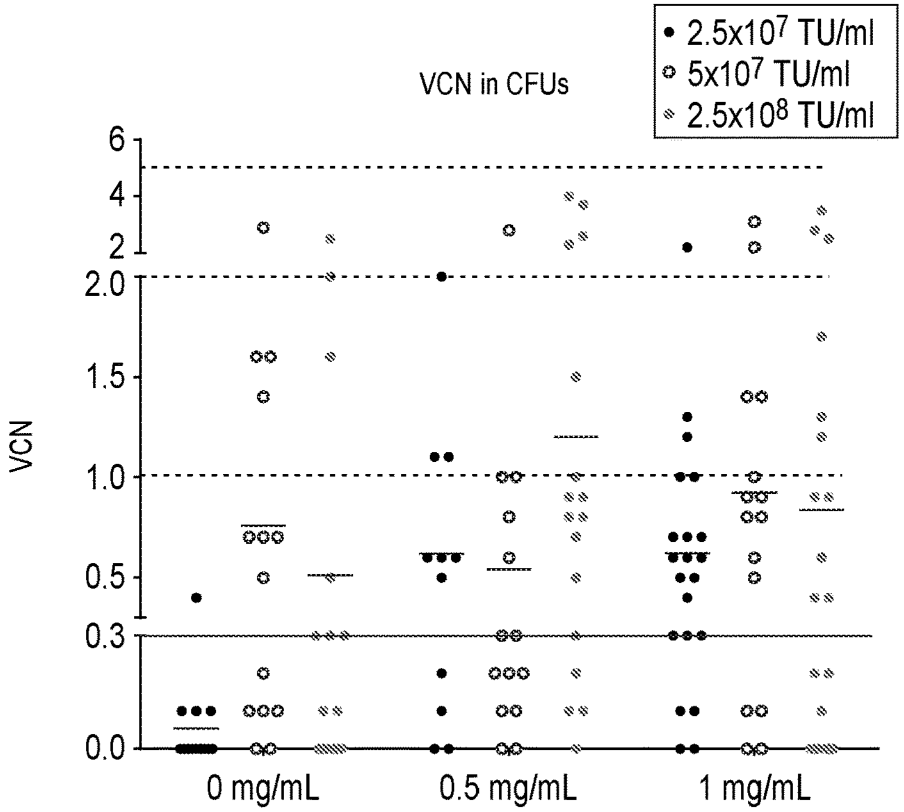
Figure 5C:
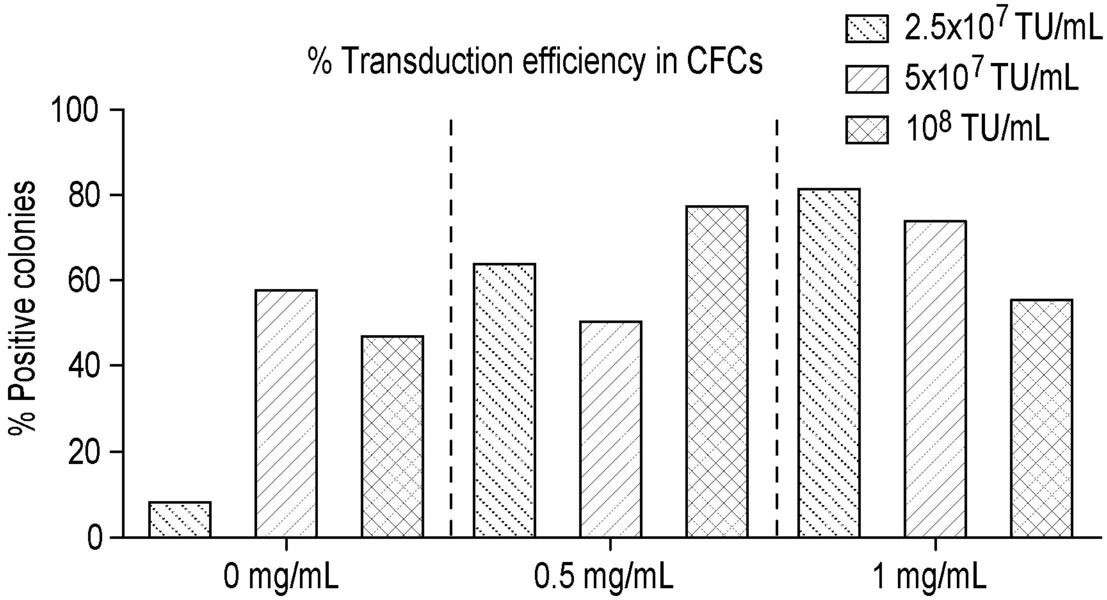

This Example establishes that protamine sulfate and poloxamer F108 (also known as poloxamer 338) increase transduction efficiency. Testing according to the general protocol illustrated in FIG. 1 was performed in liquid culture using poloxamer F108 (LentiBOOST™). Results are shown in FIG. 4 for VCN in liquid culture and FIGS. 5A-5C for analyses of CFUs assay (FIG. 5A) as well as VCN in isolated single CFUs (FIGS. 5B and 5C). At concentrations of 0.5 mg/mL, 1 mg/mL, 2 mg/mL, and 4 mg/mL LentiBOOST™ increased the transduction efficiency of a VSVG-pseudotyped LV expressing a GFP transgene reporter. As with PGE2, using the highest tested concentration of PGE2, up to about 75% of cells could be transduced (FIG. 5C).

Example 3

Transduction of Hematopoietic Cells with Protamine Sulfate, PGE2, and Poloxamer F108

Figure 6:
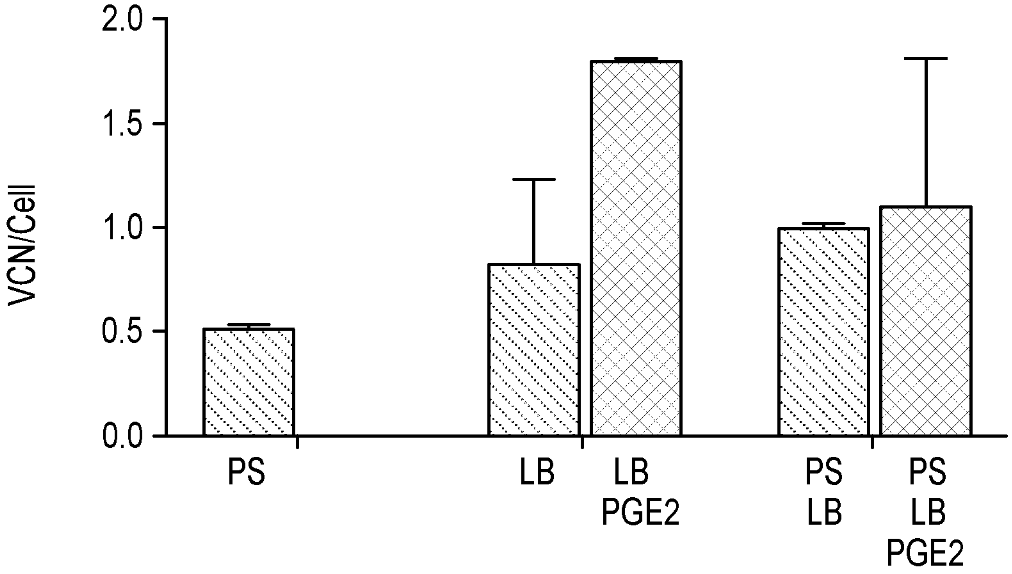
FIG. 6 shows results for VCN determination for cells in liquid culture transduced using one or more of LentiBOOST (LB), PGE2, and Protamine Sulfate (PS).
Figure 7A:
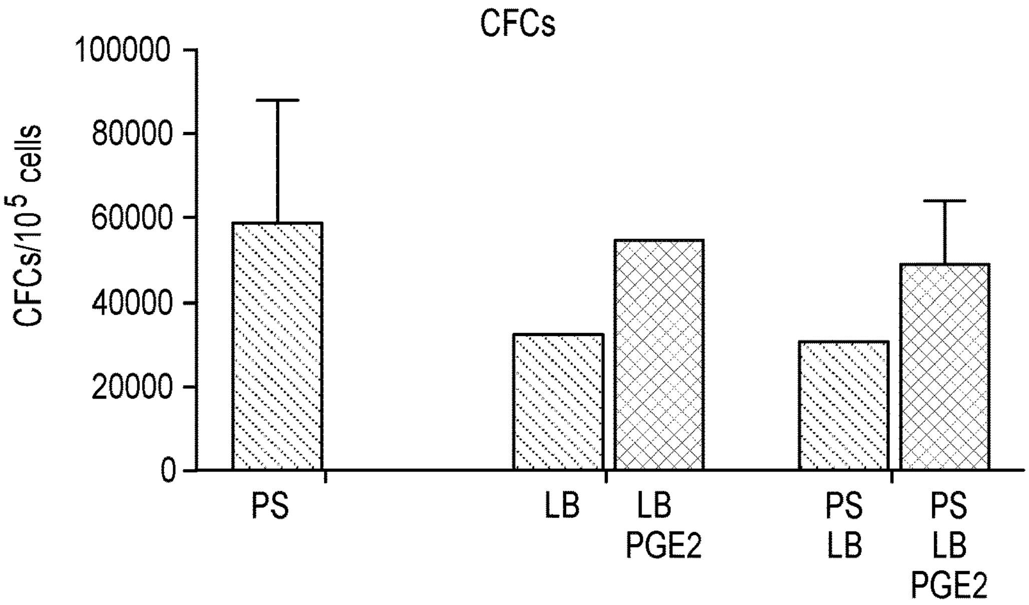
FIGS. 7A-7E show results for CFC assay for cells transduced using one or more of LentiBOOST (LB), PGE2, and Protamine Sulfate (PS) (FIG. 7A), VCN determination (FIG. 7B), and percent (%) of transduction in the CFC assay for cells transduced in the presence of PS alone, or LB, PGE2, and PS (FIG. 7C).
Figure 7B:
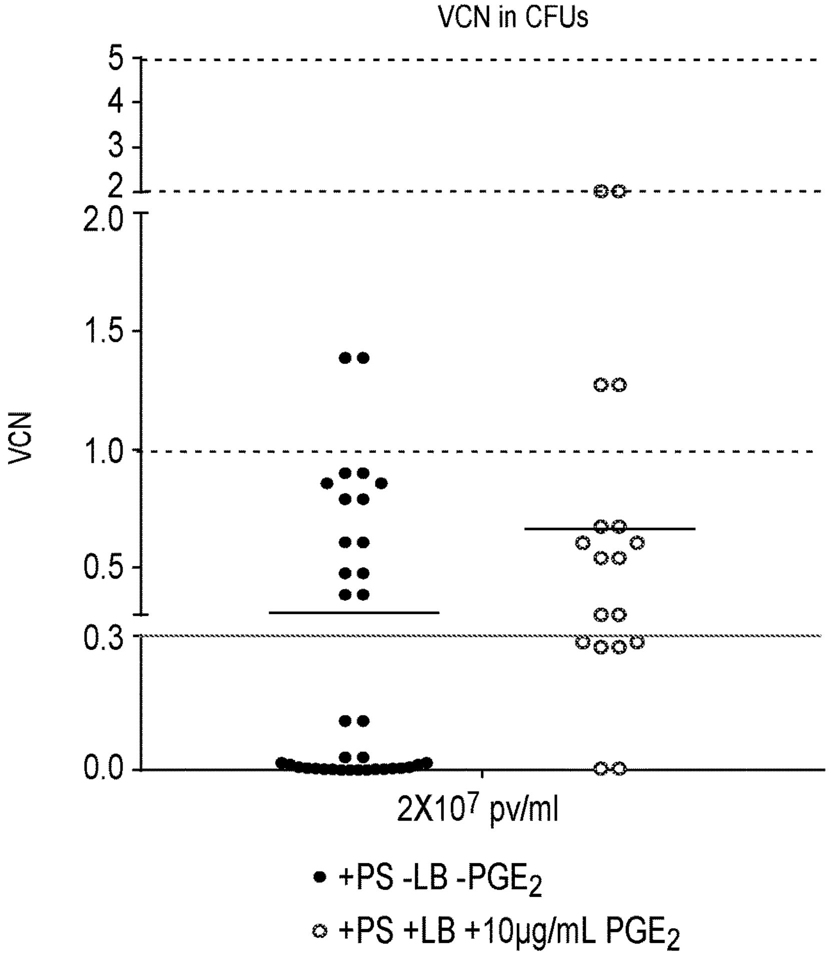
Figure 7C:
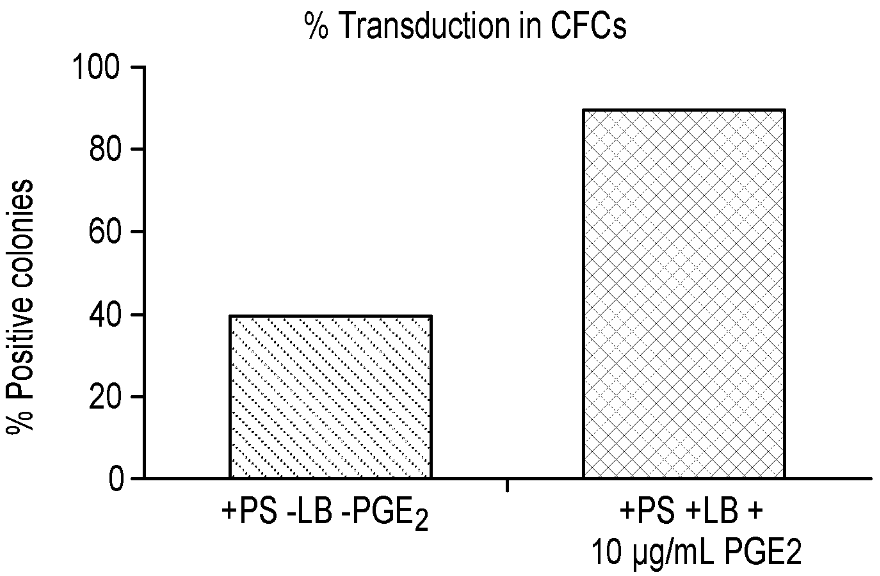
Figure 7D:
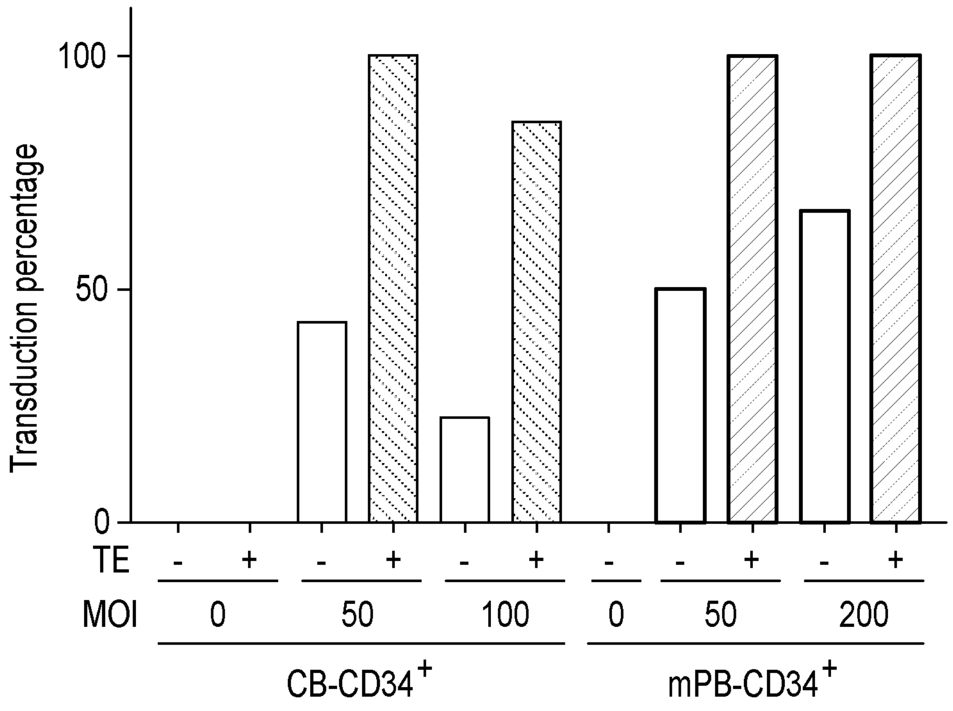
Figure 7E:
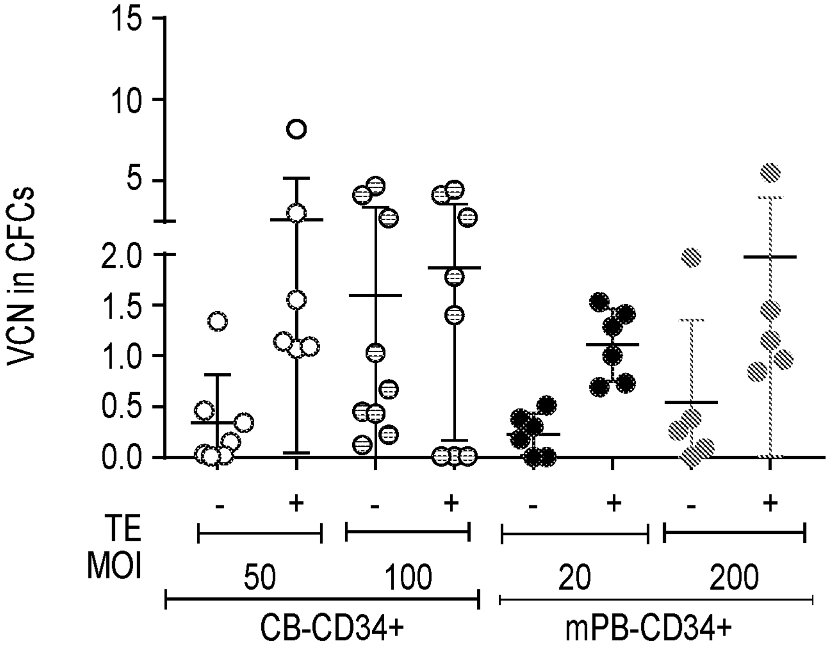

This Example establishes that the combination of protamine sulfate, PGE2, and LentiBOOST™ surprisingly increased the transduction efficiency beyond that observed with either PGE2 or LentiBOOST™ alone. Testing according to the protocol illustrated in FIG. 1 was performed and used to compare protamine sulfate (PS), LentiBOOST™ (LB), LB plus PGE2, PS plus LB, or PS plus LB plus PGE2. LB was used at a concentration of 1 mg/mL, PGE2 was used at a concentration of 10 μg/mL, and PS was used at 4 μg/mL. Results obtained for VCN in transduced cells after 14 days of liquid culture are shown in FIG. 6. FIG. 7A shows CFUs assay with transduced cells derived from CB and mPB. Also, VCN in isolated colonies in the presence of LB plus PGE2 plus PS is shown (FIG. 7B, FIG. 7E), and transduction efficiency is shown (FIG. 7C, FIG. 7D). As shown in FIG. 7C, greater than 80% of cells are transduced with vector under these conditions.

Example 4

Scale-Up and In Vivo Testing of Transduction Enhancer Methods

Figure 8:
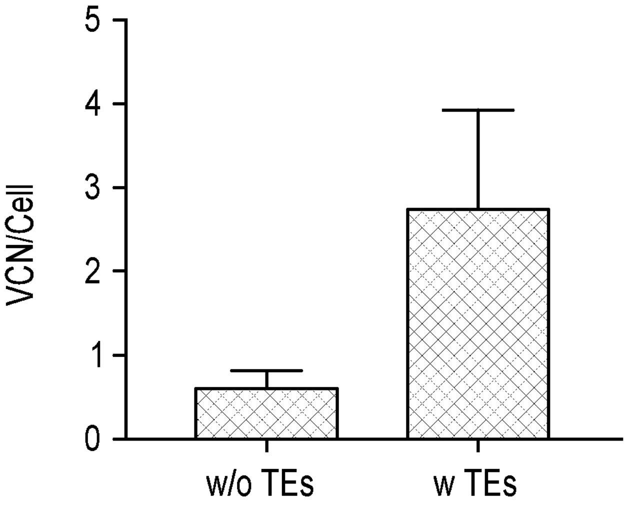
FIG. 8 shows scale up results for transduction with PS alone ("w/o TEs") or with PS and transduction enhancers LB and PGE2 ("w TEs"). VCN assay is shown for cells after 14 days in liquid culture.
Figure 9A:
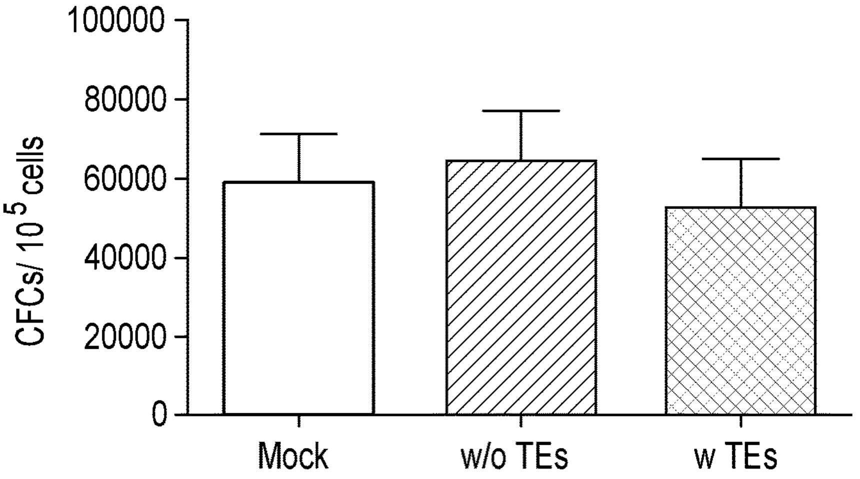
FIGS. 9A-9C show scale up results for transduction with PS alone or PS with transduction enhancers LB and PGE2.
Figure 9B:
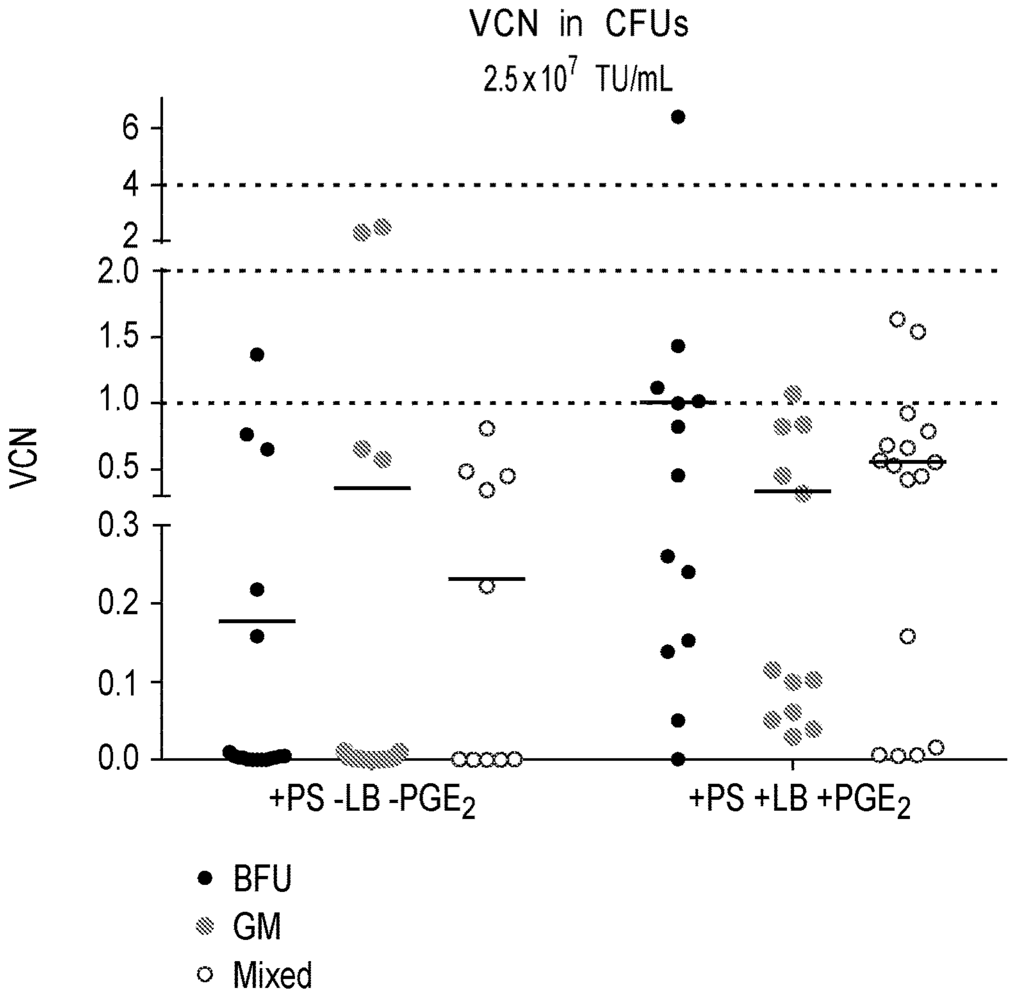
Figure 9C:
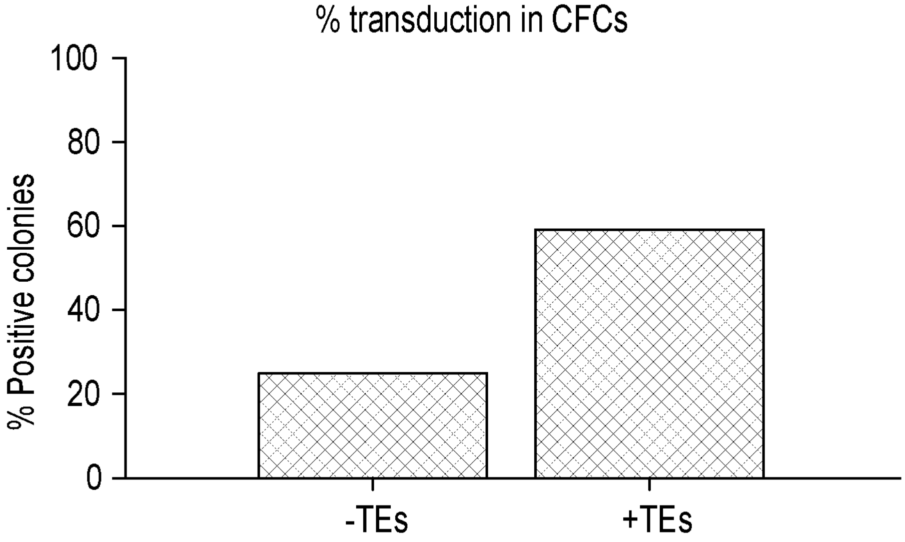
Figure 10A:
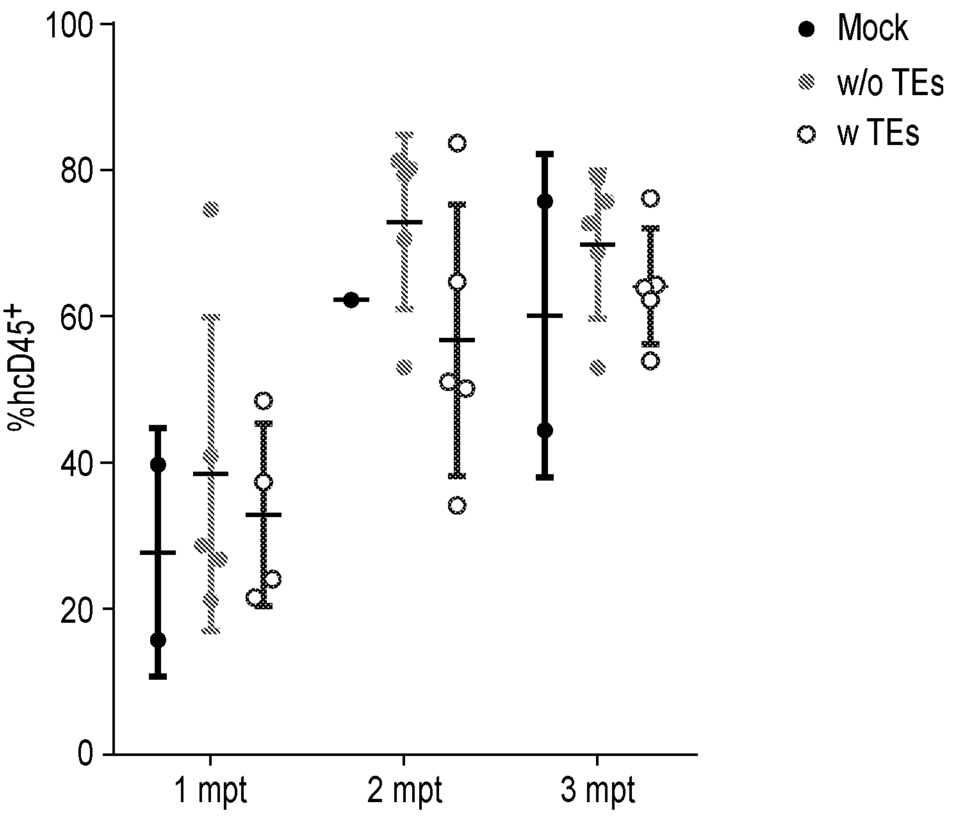
FIGS. 10A and 10B show in vivo results for transduced CD34+ cells with PS alone or PS with transduction enhancers LB and PGE2 transplanted into immunodeficient NSG mice. Percent (%) human CD45-positive ($hCD45^+$) cells (FIG. 10A) and VCN/cell (FIG. 10B) are shown. Result are shown one (1), two (2), or three (3) months post-transplant (mpt).
Figure 10B:
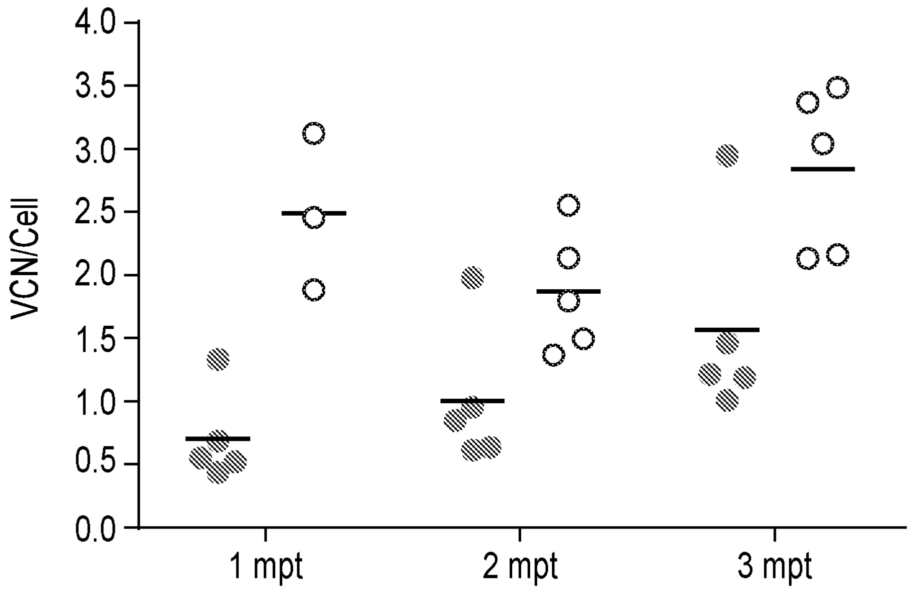

This Example demonstrates that the protocols established in Examples 1-3 can be transferred to a therapeutic vector and scaled to produce sufficient vector for clinical studies, using cord blood as the input. Scale-up of the transduction procedure was performed using CD34-enriched cord blood (CB) cells and a LV produced from pCCL-PGK-FANCAW-82-PRO without transduction enhancers (other than PS, which was used in all experiments) or with transduction enhancers (+TE), specifically LB, PGE2, and PS. LB was used at a concentration of 1 mg/mL, PGE2 was used at a concentration of 10 μg/mL, and PS was used at 4 μg/mL. VCN after 14 days of liquid culture is shown in FIG. 8. Results for CFUs assay (FIG. 9A), VCN in isolated single CFUs (FIG. 9B) as well as transduction efficiency in CFUs (FIG. 9C) are shown in transduced cells in vitro, prior to transplantation in FIGS. 9A-9C. Results are shown for burst forming unit-erythroid (BFU-E) cells, granulocyte-macrophage progenitors CFU-GM), and myeloid progenitors (CFU-GM) in FIG. 9B. FIGS. 10A and 10B show the in vivo results. Cord blood $CD34^+$ cells were transduced in the presence or absence of transduction enhancers (TEs: LB plus PGE2 plus PS), with therapeutic LV overnight at a multiplicity of infection (MOI) of 50. LB was used at a concentration of 1 mg/mL, PGE2 was used at a concentration of 10 μg/mL, and PS was used at 4 μg/mL. Collected transduced cells were then washed and suspended at a density of $1\text{-}2.5\times10^6$ cell/mL. A range of $1.3\text{-}1.6\times10^5$ transduced cells were intravenously transplanted into immune-deficient NSG mice irradiated with 1.5Gy as a xenogenic model of human hematopoiesis. Percentage (%) of human CD45-positive ($hCD45^+$) cells (FIG. 10A) and VCN/cell (FIG. 10B) were assessed one (1), two (2), or three (3) months post-transplant (mpt) in bone marrow cells from transplanted animals.

Example 5

Figure 11:
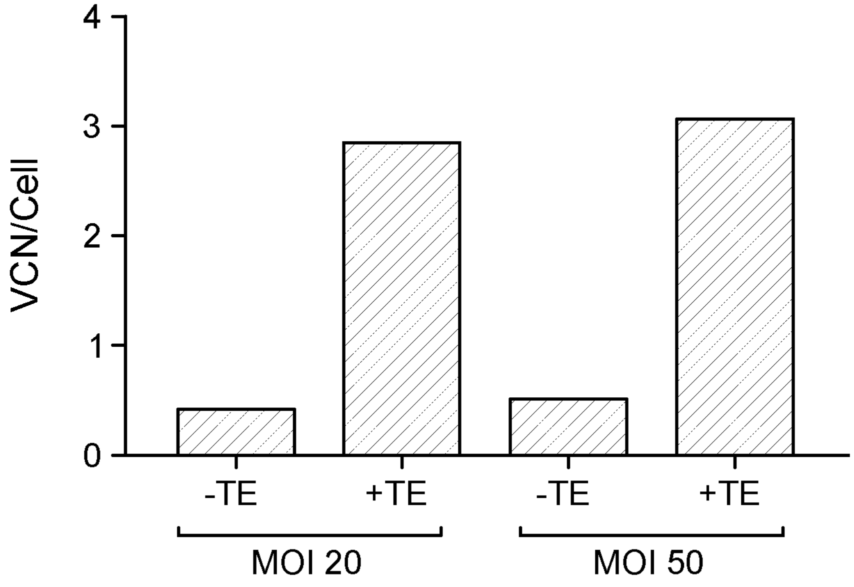
FIG. 11 shows VCN in liquid culture for GMP LV batch with (+TE) or without (−TE) transduction enhancers LB and PGE2 at 20 or 50 MOI.
Figure 12B:
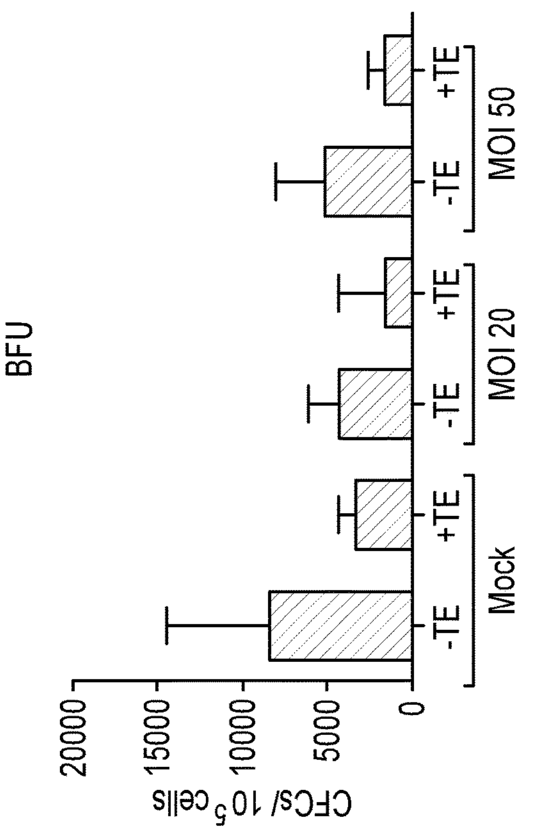
FIGS. 12A-12D show colony forming unit (CFU) for total cells (FIG. 12A), BFU (FIG. 12B), GM (FIG. 12C), and mixed myeloid progenitors (FIG. 12D) for GMP LV batch with (+TE) or without (−TE) transduction enhancers LB and PGE2.
Figure 12A:
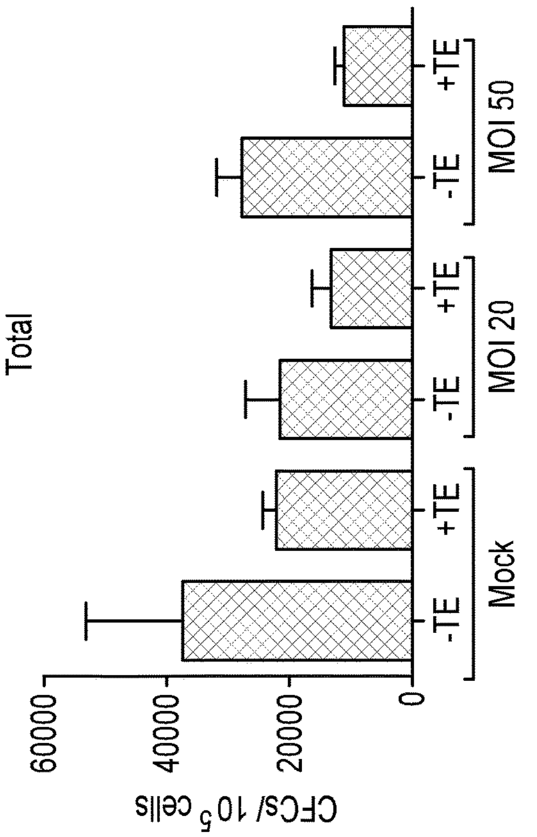
Figure 12D:
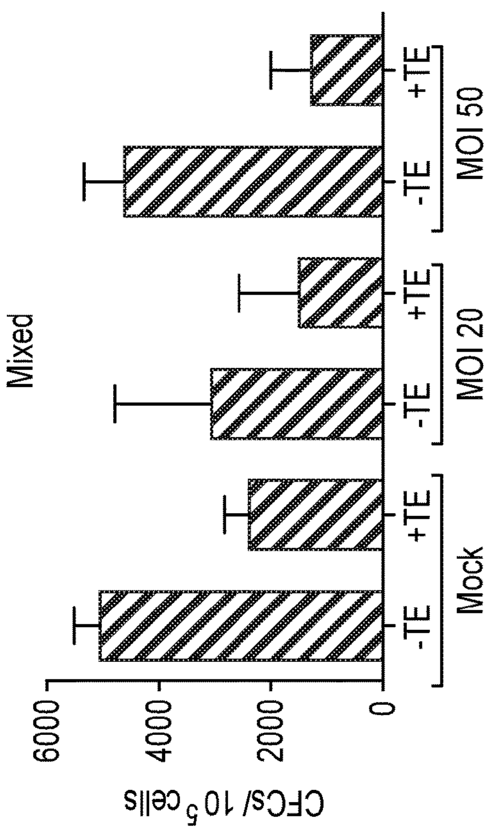
Figure 12C:
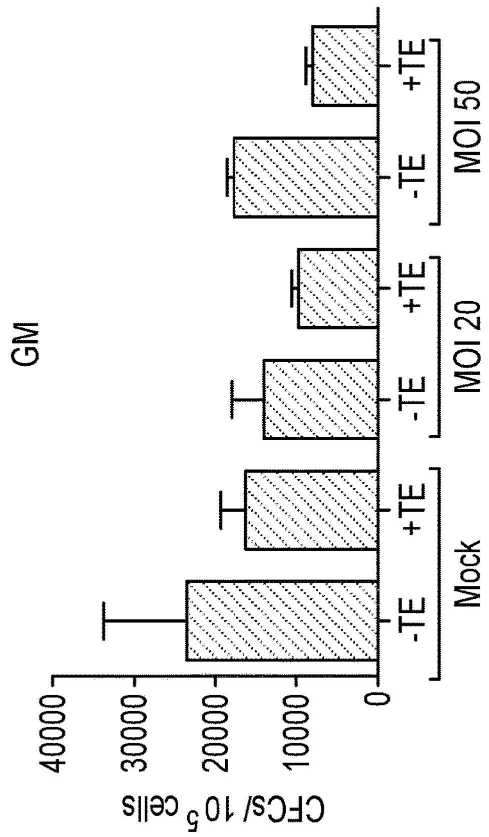
Figure 13A:
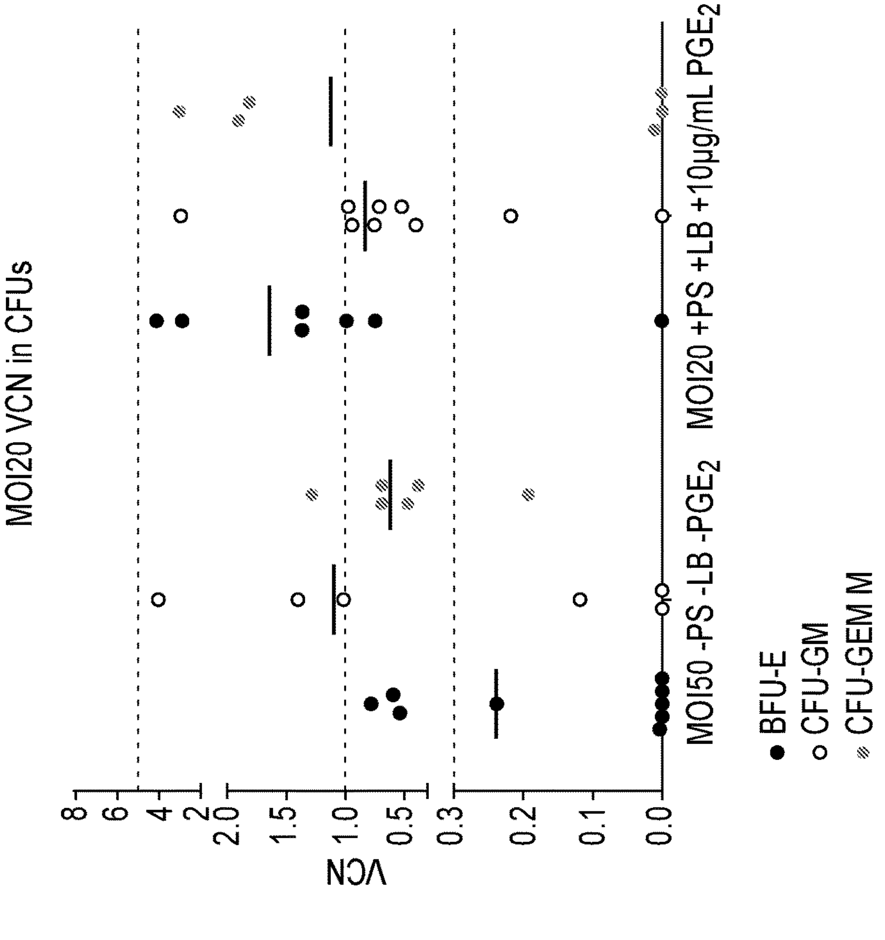
FIGS. 13A and 13B show VCN in CFUs for GMP LV batch with (+TE) or without (−TE) transduction enhancers LB and PGE2 for burst forming unit-erythroid (BFU-E) cells, granulocyte-macrophage progenitors CFU-GM), and myeloid progenitors (CFU-GM) at MOI 20 (FIG. 13A) and MOI 50 (FIG. 13B).
Figure 13B:
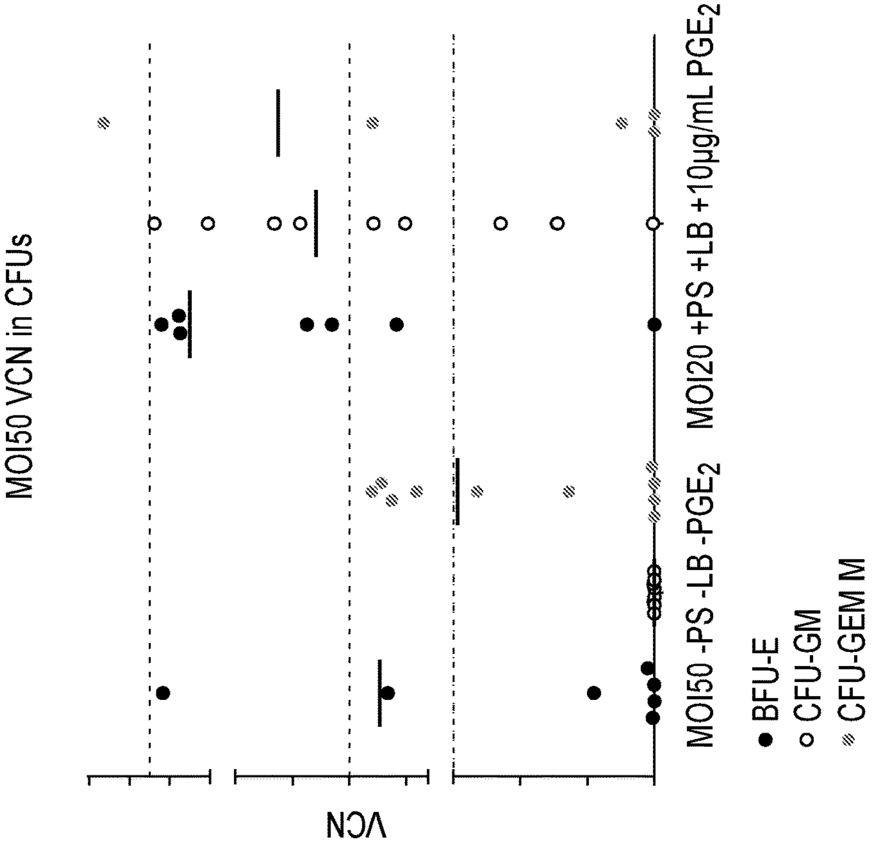
Figure 14A:
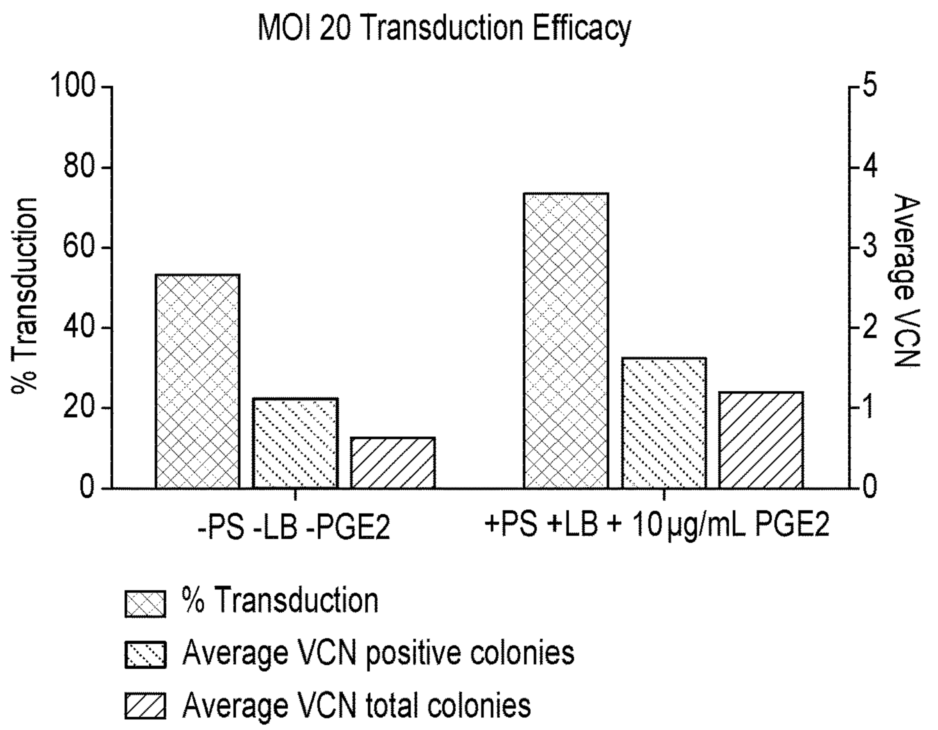
FIGS. 14A and 14B show VCN and transduction efficiency in CFUs with (+TE) or without (−TE) transduction enhancers LB and PGE2 at MOI 20 (FIG. 14A) and MOI 50 (FIG. 14B).
Figure 14B:
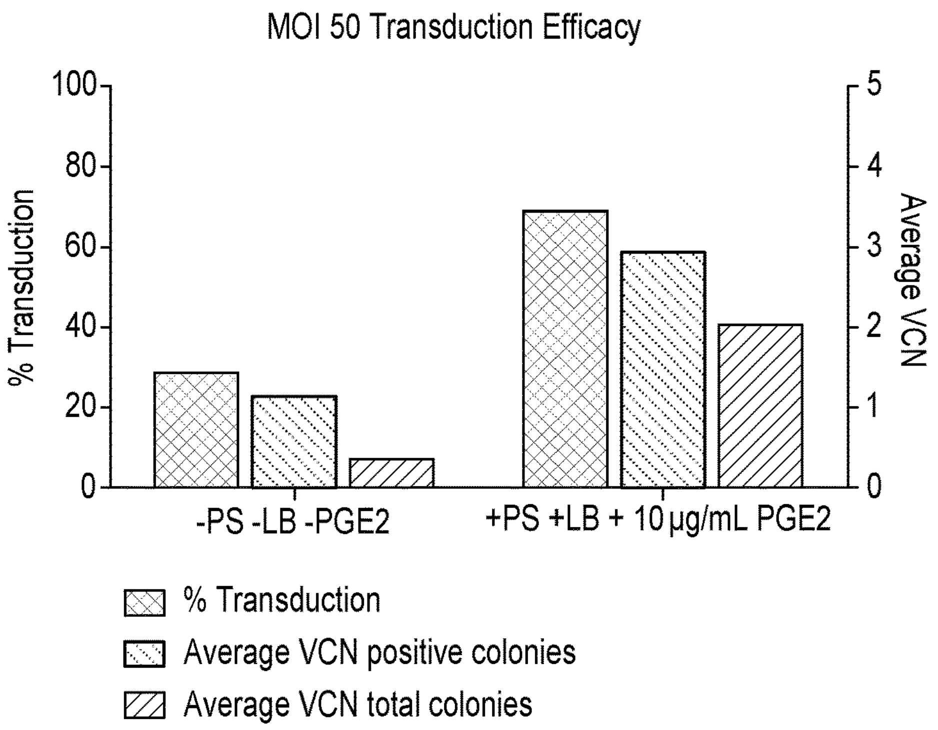

LV Production Under Good Manufacturing Practices (GMP) Conditions and Transduction of MPB This Example demonstrates that the protocols established in Examples 1-4 can be transferred to a therapeutic vector and scaled to produce sufficient vector for clinical studies, using mobilized peripheral blood as the input. A GMP LV production was performed and used in a next set of experiments performed using CD34+ hematopoietic stem cells purified from mobilized peripheral blood (mPB) from a healthy donor. The LV vector was a VSVG-pseudotyped LV expressing the FANCA transgene, which was produced using the pCCL-PGK-FANCAW-82-PRO transfer vector. FIG. 11 shows VCN/cell in transduced cells after 14 days in liquid culture with (+TE) or without (−TE) transduction enhancers PS, LB and PGE2 and at two different MOIs. LB was used at a concentration of 1 mg/mL, PGE2 was used at a concentration of 10 μg/mL, and PS was used at 4 μg/mL. FIGS. 12A-12D show the results of colony forming unit (CFU) assays for total cells, BFU, GM, and mixed myeloid progenitors for GMP003 with (+TE) or without (−TE) transduction enhancers PS, LB and PGE2 at two different MOIs. FIGS. 13A and 13B show VCN in isolated single CFUs for GMP003 with (+TE) or without (−TE) transduction enhancers PS, LB and PGE2 at 20 or 50 MOI. Results are shown for burst forming unit-erythroid (BFU-E) cells, granulocyte-macrophage progenitors CFU-GM), and myeloid progenitors (CFU-GM). FIGS. 14A and 14B show transduction efficiency and VCN in CFUs with (+TE) or without (−TE) transduction enhancers PS, LB and PGE2 for burst forming unit-erythroid (BFU-E) cells, granulocyte-macrophage progenitors (GM), and myeloid progenitors (Mixed).

What is claimed:

1. A method of ex vivo genetic modification of hematopoietic cells comprising pre-stimulating the hematopoietic cells with a recombinant fibronectin fragment, and contacting the hematopoietic cells with a recombinant retroviral vector comprising a sequence encoding a therapeutic protein operably linked to a promoter sequence, Prostaglandin E2 (PGE2) or a derivative thereof, and a poloxamer.

2. The method of claim 1, wherein the recombinant retroviral vector is a recombinant lentiviral vector.

3. The method of claim 1, wherein the hematopoietic cells are CD34-enriched cells.

4. The method of claim 1, wherein the poloxamer is selected from the group consisting of poloxamer 288, poloxamer 335, poloxamer 338, and poloxamer 407.

5. The method of claim 4, wherein the poloxamer is poloxamer 338.

6. The method of claim 1, wherein the PGE2 or derivative thereof is a modified PGE2.

7. The method of claim 6, wherein the PGE2 or derivative thereof is 16,16-dimethyl PGE2 (dmPGE2).

8. The method of claim 1, wherein the PGE2 or derivative thereof is an unmodified PGE2.

9. The method of claim 1, wherein the cells were transduced by contacting the cells with the Prostaglandin E2 (PGE2) or derivative thereof, the poloxamer, the recombinant fibronectin fragment, and protamine sulfate.

10. The method of claim 9, wherein the concentration of the protamine sulfate is 4-10 μg/mL.

11. The method of claim 10, wherein the concentration of the protamine sulfate is about 4 μg/mL.

12. The method of claim 1, wherein the cells were contacted with the transduction enhancers during the same or an overlapping time period.

13. The method of claim 1, wherein the concentration of the PGE2 or derivative thereof is 5-30 μg/mL.

14. The method of claim 13, wherein the concentration of the PGE2 or derivative thereof is about 10 μg/mL.

15. The method of claim 1, wherein the concentration of the poloxamer is 200-1200 μg/mL.

16. The method of claim 15, wherein the concentration of the poloxamer is about 1000 μg/mL.

17. The method of claim 1, wherein the concentration of the recombinant fibronectin fragment is 5-50 ug/mL.

18. The method of claim 17, wherein the concentration of the recombinant fibronectin fragment is 20 ug/mL.

19. The method of claim 1, wherein the hematopoietic cells were obtained from a subject before being contacted ex vivo with the retroviral vector.

20. The method of claim 19, wherein the polynucleotide encodes a therapeutic protein that is mutated or lacking in the subject due to a genetic disease or disorder.

21. The method of claim 20, wherein the therapeutic protein is selected from the group consisting of Red-cell type Pyruvate Kinase (RPK), Integrin beta 2 (ITGB2), Fanconi Anemia complementation group A protein (FANCA), Fanconi Anemia complementation group C protein (FANCC), Fanconi Anemia complementation group G protein (FANCG), and T cell immune regulator 1, ATPase H+ transporting V0 subunit a3 (TCIRG1), chloride voltage-gated channel 7 (CLCN7), tumor necrosis factor (ligand) superfamily, member 11 (TNFSF11), Pleckstrin homology and RUN domain containing M1 (PLEKHM1), tumor necrosis factor (ligand) superfamily, member 11a (TNFRSF11A) and osteopetrosis associated transmembrane protein 1 (OSTM1).

22. The method of claim 21, wherein the disease or disorder is selected from the group consisting of Fanconi Anemia, Leukocyte Adhesion Deficiency Type I, Pyruvate Kinase Deficiency, and Infantile Malignant Osteopetrosis.

23. The method of claim 22, wherein the disease or disorder is Fanconi Anemia, and the therapeutic protein is FANCA, FANCC, or FANCG.

24. The method of claim 22, wherein the disease or disorder is Leukocyte Adhesion Deficiency Type I, and the therapeutic protein is ITGB2.

25. The method of claim 22, wherein the disease or disorder is Pyruvate Kinase Deficiency, and the therapeutic protein is RPK.

26. The method of claim 22, wherein the disease or disorder is Infantile Malignant Osteopetrosis, and the therapeutic protein is TCIRG1.

27. The method of claim 1, wherein the hematopoietic cells are bone-marrow (BM)-derived cells, cord blood (CB)-derived cells, or mobilized peripheral blood (mPB) cells.

* * * * *